US012741001B2

(12) United States Patent
Bernstein et al.

(10) Patent No.: US 12,741,001 B2

(45) Date of Patent: Sep. 22, 2026

(54) COMPOSITIONS AND METHODS FOR PROVIDING HEMATOPOIETIC FUNCTION WITHOUT HLA MATCHING

(71) Applicant: Fred Hutchinson Cancer Research Center, Seattle, WA (US)

(72) Inventors: Irwin D. Bernstein, Seattle, WA (US); Colleen Delaney, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 0 days.

(21) Appl. No.: 16/378,229

(22) Filed: Apr. 8, 2019

(65) Prior Publication Data

US 2019/0298778 A1 Oct. 3, 2019

Related U.S. Application Data

(63) Continuation of application No. 13/640,297, filed as application No. PCT/US2011/031953 on Apr. 11, 2011, now abandoned.

(60) Provisional application No. 61/322,544, filed on Apr. 9, 2010.

(51) Int. Cl.

| | |
|---|---|
| ***A61K 35/51*** | (2015.01) |
| ***A61K 35/50*** | (2015.01) |
| ***C12N 5/0789*** | (2010.01) |
| ***G16H 10/40*** | (2018.01) |
| ***G16H 20/40*** | (2018.01) |

(52) U.S. Cl.

CPC .............. *A61K 35/51* (2013.01); *A61K 35/50* (2013.01); *C12N 5/0647* (2013.01); *G16H 10/40* (2018.01); *G16H 20/40* (2018.01); *C12N 2501/125* (2013.01); *C12N 2501/145* (2013.01); *C12N 2501/2303* (2013.01); *C12N 2501/26* (2013.01); *C12N 2501/42* (2013.01); *Y02A 90/10* (2018.01)

(58) Field of Classification Search

None

See application file for complete search history.

(56) References Cited

U.S. PATENT DOCUMENTS

| | | | |
|---|---|---|---|
| 5,004,681 A | 4/1991 | Boyse et al. | |
| 5,648,464 A | 7/1997 | Artavanis-Tsakonas et al. | |
| 5,780,300 A | 7/1998 | Artavanis-Tsakonas et al. | |
| 5,849,869 A | 12/1998 | Artavanis-Tsakonas et al. | |
| 5,856,441 A | 1/1999 | Artavanis-Tsakonas et al. | |
| 7,147,626 B2 | 12/2006 | Goodman et al. | |
| 7,399,633 B2 | 7/2008 | Bernstein et al. | |
| 2004/0067583 A1 | 4/2004 | Bernstein et al. | |
| 2005/0063958 A1* | 3/2005 | Symonds ................ | A61P 31/18 424/93.21 |
| 2007/0053888 A1 | 3/2007 | Hariri | |
| 2013/0095080 A1 | 4/2013 | Bernstein et al. | |
| 2018/0085406 A1 | 3/2018 | Bernstein et al. | |
| 2019/0298777 A1 | 10/2019 | Bernstein et al. | |

FOREIGN PATENT DOCUMENTS

| | | |
|---|---|---|
| JP | 2005102656 | 4/2005 |
| JP | 2006517975 | 8/2006 |
| JP | 2008517948 | 5/2008 |
| JP | 2008545755 | 12/2008 |
| WO | WO199219734 A1 | 11/1992 |
| WO | WO199312141 A1 | 6/1993 |
| WO | WO199627610 A1 | 9/1996 |
| WO | WO199701571 A1 | 1/1997 |
| WO | WO2003075789 A2 | 9/2003 |
| WO | WO2004071283 A2 | 8/2004 |
| WO | WO2005097190 | 10/2005 |
| WO | WO2006047569 A1 | 4/2006 |
| WO | WO2006130812 A2 | 12/2006 |
| WO | WO2007087453 A2 | 8/2007 |
| WO | WO2007095594 A2 | 8/2007 |
| WO | WO2008070861 A2 | 6/2008 |
| WO | WO2010059401 A2 | 5/2010 |
| WO | WO2011127472 A1 | 10/2011 |
| WO | WO2013086436 A1 | 6/2013 |

OTHER PUBLICATIONS

Office Action Dated Feb. 5, 2019 for Canadian Patent Application No. 2795627, 3 pages.

Delaney, et al., "Notch-Mediated Expansion of Human Cord Blood Progenitor Cells Results in Rapid Myeloid Reconstitution in Vivo Following Myeloablative Cord Blood Transplantation," Blood, (ASH Annu Meet Abst), 2008, 112: Abstract 212.

Office Action Dated Mar. 31, 2020 for Japanese Application No. 2019-051186, 13 pages.

Zhang, et al., "Angiopoietin-like 5 and IGFBP2 stimulate ex vivo expansion of human cord blood hematopoietic stem cells as assayed by NOD/SCID transplantation," Blood, vol. 111, 2008, pp. 3415-3423.

Zhang, et al, "Co-culture of Umbilical Cord Blood CD34p Cells with Human Mesenchymal Stem Cells", Tissue Eng., vol. 12, No. 8, 2006, pp. 2161-2170.

Advani et al., "Umbilical cord blood transplantation for acute myeloid leukemia", Current Opinion in Hematology, 16, 2009, pp. 124-128.

(Continued)

*Primary Examiner* — Nghi V Nguyen

(74) *Attorney, Agent, or Firm* — Christensen O'Connor Johnson Kindness PLLC

(57) ABSTRACT

The present invention relates to methods and compositions for providing hematopoietic function in immunodeficient human patients, by selecting an expanded human umbilical cord blood stem/progenitor cell sample without taking into account the HLA-type of the expanded human cord blood stem/progenitor sample or the HLA-type of the patient; and administering the selected expanded human cord blood stem/progenitor cell sample to the patient. Methods for obtaining the expanded human cord blood stem/progenitor cell samples, banks of frozen expanded human cord blood stem/progenitor cell samples, and methods for producing such banks are also provided herein.

9 Claims, 19 Drawing Sheets

(56) References Cited

OTHER PUBLICATIONS

Alam, et al., "Notch signaling drives IL-22 secretion in CD4+ T cells by stimulating the aryl hydrocarbon receptor," Proc. Natl. Acad. Sci. U.S.A.., vol. 107, 2010, pp. 5946-5948.
Alberts, et al. (ed.), Molecular Biology of the Cell, 2nd ed, "Differentiated Cells and the Maintenance of Tissues," Garland Publishing: New York, Chapter 17, 1989.
Alberts, et al., Molecular Biology of the Cell, 4th ed., Chapter 24, 2002, pp. 1363-1364.
Artavanis-Tsakonas, et al., "Notch signaling," Science, vol. 268, 1995, pp. 225-232.
Artavanis-Tsakonas, et al., "Choosing a cell fate: a view from the Notch locus," Trends Genet., vol. 7, 1991, pp. 403-408.
Artavanis-Tsakonas, et al., "Notch signaling: cell fate control and signal integration in development," Science, vol. 284, 1999, pp. 770-776.
Audet, "Stem cell bioengineering for regenerative medicine", Expert Opin. Bio. Ther., vol. 4, No. 5, 2004, pp. 631-644.
Barker, et al., "Combined effect of total nucleated cell dose and HLA match on transplantation outcome in 1061 cord blood recipients with hematologic malignancies," Blood, vol. 115, No. 9, 2010, pp. 1843-1849.
Barker, et al., "Transplantation of 2 partially HLA-matched umbilical cord blood units to enhance engraftment in adults with hematologic malignancy", Blood, vol. 105, No. 3, 2005, pp. 1343-1347.
Becker, et al., 2008, "Oral Small Molecule Inhibitor of VLA-4 Overcomes Adhesion Mediated Chemotherapy C06 Resistance of Acute Myeloid Leukemia (AML) Blasts in Vitro, without Impairment of Normal Blood Cell Recovery When Combined with Chemotherapy in Vivo," Blood, (ASH Annual Meeting Abstracts], vol. 112, 2008, p. 858.
Boitano, et al., "Aryl hydrocarbon receptor antagonists promote the expansion of human hematopoietic stem cells," Science, vol. 329, 2010, pp. 1345-1348.
Boo, et al., "Cord blood unit access and selection: 2010 and beyond: best practices and emerging trends in cord blood unit selection", Biol. Blood Marrow Transplant, vol. 17, 2011, S46-S51.
Carlesso, et al., "Notch 1-induced delay of human hematopoietic progenitor cell differentiation is associated with altered cell cycle kinetics," Blood, vol. 93, 1999, pp. 838-848.
Clinicaltrials.gov, "A Pilot Study to Evaluate the Co-Infusion of Ex Vivo Expanded Cord Blood Cells With an Unmanipulated Cord Blood Unit in Patients Undergoing Cord Blood Transplant for Hematologic Malignancies," ClinicalTrials.gov, http://clinicaltrials.gov/ct2/show/NCT00343798 (last accessed Aug. 27, 2013).
Croop et al., "Large-scale mobilization and isolation of CD34+ cells from normal donors", Bone Marrow Transplantation, 26, Sep. 2000, pp. 1271-1279.
Dahlberg, et al., "Ex vivo expansion of human hematopoietic stem and progenitor cells," Blood, vol. 117, pp. 6083-6090.
Dallas, et al., "Enhanced T-cell reconstitution by hematopoietic progenitors expanded ex vivo using the Notch ligand Delta1," Blood, vol. 109, 2007, pp. 3579-3587.
Dao, et al., "Adhesion to fibronectin maintains regenerative capacity during ex vivo culture and transduction of human hematopoietic stem and progenitor cells," Blood, vol. 92, No. 12, 1998, pp. 4612-4621.
Dao, et al., "Immunodeficient mice as models of human hematopoietic stem cell engraftment," Curr. Opin. Immunol., vol. 11, 1999, pp. 532-537.
De Lima, et al., "Double Cord Blood Transplantation (CBT) with and without Ex-Vivo Expansion (EXP): A Randomized, Controlled Study," Blood, vol. 112, No. 11, 2008, 6 pages.
De Lima, et al., "Transplantation of ex vivo expanded cord blood cells using the copper chelator tetraethylenepentamine: a phase I/II clinical trial," Bone Marrow Transplant., vol. 41, No. 9, 2008, pp. 771-778.
Declaration of Colleen Delaney, M.D. Under 37 C.F.R. 1.132, as tiled in U.S. Appl. No. 13/640,298 (dated May 30, 2014).
Deftos, et al., "Correlating notch signaling with thymocyte maturation," Immunity, vol. 9, 1998, pp. 777-786.
Delaney, et al., "Notch-Mediated Expansion of Human Cord Blood Progenitor Cells Results in Rapid Myeloid Reconstitution In Vivo Following Myeloablative Cord Blood Transplantation," Blood, vol. 112, No. 11, 6 pages.
Delaney, et al., "Dose-dependent effects of the Notch ligand Delta1 on ex vivo differentiation and in vivo marrow repopulating ability of cord blood cells," Blood, vol. 106, 2005, pp. 2693-2699.
Delaney, et al., "Notch-mediated expansion of human cord blood progenitor cells capable of rapid myeloid reconstitution," Nature Med., vol. 16, No. 2, 2010, pp. 232-236.
Delaney, et al., "The role of HLA in umbilical cord blood transplantation," Best Pract. Res. Clin. Haematology, vol. 23, 2010, pp. 179-187.
Department of Health and Human Services, 2006, Regenerative Medicine, Chapter 2, http://stemcells.nih.gov/info/scireport/2006report.htm (last accessed Aug. 27, 2013).
Department of Health and Human Services, 2009, Hematopoietic Stem Cells, Chapter 5, http://stemcells.nih.gov/info/scireport/chapter5.asp (last accessed Aug. 27, 2013).
Department of Health and Human Services. Oct. 2009, Guidance for Industry: Minimally manipulated, unrelated allogeneic placental/umbilical cord blood intended for hematopoietic reconstitution for specified indications, http://www.fda.gov/downloads/BiologicsBloodVaccines/GuidanceComplianceRegulatoryInformation/Guidances/Blood/UCM187144.pdf (last accessed Mar. 26, 2014 ).
Dick, "Normal and leukemic human stem cells assayed in SCID mice," Seminars in Immunol., vol. 8, 1996, 197-206.
Eapen, et al., "Effect of donor-recipient HLA matching at HLA A, B, C, and DRB1 on outcomes after umbilical cord blood transplantation for leukemia and myelodysplastic syndrome: a retrospective analysis", Lancet Oncol., vol. 12, 2011, pp. 1214-1221.
Eapen, et al., "Impact of allele-level HLA matching on outcomes after myeloablative single unit umbilical cord blood transplantation for hematologic malignancy", Blood, vol. 123, No. 1, 2014, pp. 133-140.
Ende, et al., "Pooled umbilical cord blood as a possible universal donor for marrow reconstitution and use in nuclear accidents", Life Sciences, vol. 69, 2001, pp. 1531-1539.
FHCRC clinical protocol 2044, A Pilot Study to Evaluate the Co-infusion of Ex Vivo Expanded Umbilical Cord Blood Progenitors with an Unmanipulated Cord Blood Graft in Patients Undergoing Umbilical Cord Blood Transplantation for Hematologic Malignancies, http://www.seattlecca.org/clinical-trials/transplant-2044 .cfm, (last accessed Aug. 30, 2013).
Gan, et al., "Differential Maintenance of Primitive Human SCID-Repopulating Cells, Clonogenic Progenitors, and Long-Term Culture-Initiating Cells After Incubation on Human Bone Marrow Stromal Cells," Blood, vol. 90, No. 2, 1997, pp. 641-650.
Gluckman, et al., "Donor selection for unrelated cord blood transplants," Curr. Opin. Immunol., vol. 18, 2006, pp. 565-570.
Go, et al., "Cell proliferation control by Notch signaling in *Drosophila* development," Development, vol. 125, 1998, pp. 2031-2040.
Gorin, "Collection, manipulation and freezing of haemopoietic stem cells," Clinics in Haematology, vol. 15, No. 1, 1986, pp. 19-48.
Gratwohl, "Cord blood meets its match", Lancet Oncol., vol. 12, 2011, pp. 1177-1178.
Greiner, et al., "SCID mouse models of human stem cell engraftment," Stem Cells, vol. 16, 1998, pp. 166-177.
Gutman, et al., "Single-unit dominance after double-unit umbilical cord blood transplantation coincides with a specific CD8+ T-cell response against the non-engrafted unit", Blood, vol. 115, No. 4, 2009, pp. 757-765.
Harris, et al., "Collection, separation and cryopreservation of umbilical cord blood for use in transplantation", Bone Marrow Transplantation, vol. 13, No. 2, 1994, pp. 135-143 Abstract Only.
Harris, "Experience in Autologous and Allogeneic Cord Blood Banking", J. Hematother., vol. 5, 1996, pp. 123-128.
Himburg, et al., "Pleiotrophin regulates the expansion and regeneration of hematopoietic stem cells," Nature Medicine, vol. 1, No. 4, 2010, pp. 475-482.

(56) References Cited

OTHER PUBLICATIONS

Hofmeister, et al., "Ex vivo expansion of umbilical cord blood stem cells for transplantation: growing knowledge from the hematopoietic niche," Bone Marrow Transplant., vol. 39, No. 2007, pp. 11-23.
International Preliminary Report on Patentability dated Oct. 9, 2012 in International Application No. PCT/US2011/031953.
Jehn, et al., "Cutting edge: protective effects of notch-1 on TCR-induced apoptosis," J. Immunol., vol. 162, 1999, pp. 635-638.
Jones, et al., "Stromal expression of Jagged 1 promotes colony formation by fetal hematopoietic progenitor cells," Blood, vol. 92, 1998, pp. 1505-1511.
Extended European Search Report Dated Nov. 13, 2019, for European Patent Application No. 19191594.1 , 11 pages.
Ka Wase, et al., "High-risk HLA allele mismatch combinations responsible for severe acute graft-versus-host disease and implication for its molecular mechanism," Blood, vol. 110, 2007, pp. 2235-2241.
Kai, 1. Hematopoietic Stem Cells, 3. Multiple umbilical cord blood transplantation, Annual Review Ketsueki, Blood, 2008, Japan, pp. 18-26.
Kim, et al., "Co-transplantation of third-party mesenchymal stromal cells can alleviate single-donor predominance and increase engraftment from double cord transplantation", Blood, vol. 103, 2004, pp. 1941-1948.
Kopan and Illagan, "The canonical Notch signaling pathway: unfolding the activation mechanism," Cell, vol. 137, 2009, pp. 216-233.
Kutzberg, "Update on umbilical cord blood transplantation", Curr. Opin. Pediatr., vol. 21, No. 1, 2009, pp. 22-29.
Li, et al., "The human homolog of rat Jagged1 expressed by marrow stroma inhibits differentiation of 32D cells through interaction with Notch1," Immunity, vol. 8, 1998, pp. 43-55.
Lister, et al, "Multiple Unit HLA-Unmatched Sex-Mismatched Umbilical Cord Blood Transplantation for Advanced Hematological Malignancy", Stem Cells and Development, vol. 16, 2007, pp. 177-186.
Majhail, et al., "Double umbilical cord blood transplantation," Curr. Opin. Immunol., vol. 18, 2006, pp. 571-575.
Milano, et al., "Cryopreserved Ex-Vivo Expanded Murine Hematopoietic Progenitors Can Engraft Across MHC Barriers and Improve Survival in a Murine Model of Acute Radiation Syndrome," Blood, vol. 116, No. 21, 2010, p. 626.
Milner, et al., A human homologue of the *Drosophila* developmental gene, Notch, is expressed in CD34+ hematopoietic precursors, Blood, vol. 83, 1994, pp. 2057-2062.
Nauta, et al., "Enhanced engraftment of umbilical cord blood-derived stem cells in NOD/SCID mice by cotransplantation of a second unrelated cord blood unit," Experimental Hematology, vol. 33, 2005, pp. 1249-1256.
Office Action Dated Mar. 27, 2019 for U.S. Appl. No. 13/640,297, 11 pages.
Office Action Dated Mar. 28, 2019 for U.S. Appl. No. 15/809,699, 8 pages.
Office Action Dated Mar. 31, 2015 in Japanese Application No. 2013-504018.
Office Action Dated Oct. 16, 2015 in U.S. Appl. No. 13/640,297, 13 pages.
Extended European Search Report Dated Oct. 25, 2016 for European Application No. 16166225.9, 12 pages.
Office Action dated Nov. 22, 2016 for Japanese Patent Application No. 2013-504018, 8 pages.
Office Action Dated Dec. 11, 2017 for Canadian Application No. 2795627, 4 pages.
Office Action Dated Dec. 26, 2017 for Japanese Patent Application No. 2017-056141, 8 pages.
Office Action Dated Dec. 3, 2013 in U.S. Appl. No. 13/640,298, 15 pages.
Office Action dated Feb. 1, 2018 for European Application No. 16166225.9, 5 pages.
Office Action Dated Feb. 20, 2017 for Canadian U.S. Appl. No. 27/956,274, 4 pages.
Office Action Dated Mar. 31, 2015 in Japanese Application No. 2013-504018, 7 pages.
Office Action Dated Mar. 8, 2016 for Japanese Patent Application No. 2013-504018, 16 pages.
Office Action Dated Aug. 10, 2018 for European Application No. 16166225.9, 4 pages.
Office Action Dated Sep. 28, 2016 for U.S. Appl. No. 13/640,297, 8 pages.
Offner, et al., "Mortality hazard functions as related to neutropenia at different times after marrow transplantation," Blood, vol. 88, 1996, p. 4058.
Ohishi, et al., "Delta-1 enhances marrow and thymus repopulating ability of human CD34(+)CD38(−) cord blood cells," J. Clin. Invest, vol. 110, 2002, pp. 1165-1174.
Ohishi, et al., "Monocytes express high amounts of Notch and undergo cytokine specific apoptosis following interaction with the Notch ligand, Delta-1," Blood, vol. 95, 2000, pp. 2847-2854.
Pui, et al., "Notch1 expression in early lymphopoiesis influences B versus T lineage determination," Immunity, vol. 11, 1999, pp. 299-308.
Radtke, et al., "Deficient T Cell Fate Specification in Mice with an Induced Inactivation of Notch1," Immunity, vol. 10, No. 5, 1999, pp. 547-558.
Reimann, et al., "Advances in adoptive immunotherapy to accelerate T-cellular immune reconstitution after HLA-incompatible hematopoietic stem cell transplantation," Immunotherapy, vol. 2, No. 4, 2010, pp. 481-496.
Robey, et al., "An activated form of Notch influences the choice between CD4 and CDS T cell lineages," Cell, vol. 87, 1996, pp. 483-492.
Rocha, et al., "Improving outcomes of cord blood transplantation: HLA matching, cell dose and other graft-and transplantation-related factors," British J. Haematology, vol. 147, 2009, pp. 262-274.
Rubinstein, et al., "Histocompatibility and Immunogenetics in Cord Blood Transplantation," Biol. Res., vol. 43, 2010, pp. 339-345.
Shpall, "Transplantation of ex vivo expanded cord blood," Biology of Blood and Marrow Transplantation, vol. 11, No. 11, 2005, p. 932.
Shpall, et al., "Transplantation of Ex Vivo Expanded Cord Blood," Biology of Blood an Marrow Transplantation, vol. 8, 2002, pp. 368-376.
Simpson, "Developmental genetics. The Notch connection," Nature, 1995, vol. 375 pp. 736-737.
Simpson, "Introduction: Notch signalling and choice of cell fates in development," Semin. Cell Dev. Biol., vol. 9, 1998, pp. 581-582.
Spitzer, et al., "High-dose combination chemotherapy with autologous bone marrow transplantation in adult solid tumors," Cancer, vol. 45, 1980, pp. 3075-3085.
European Search Report Dated Oct. 22, 2014 in European Application No. 11717379.9.
Search Report and Written Opinion dated Jul. 21, 2011 in International Application No. PCT/US2011/031957.
Thomas, et al., "Allogeneic Marrow Grafting for Hematologic Malignancy Using HL-A Matched Donor-Recipient Sibling Pairs," Blood, vol. 38, No. 3, 1971, 267-287.
Tomita, et al., "The bHLH gene Hes1 is essential for expansion of early T cell precursors," Genes Dev., vol. 13, 1999, pp. 1203-1210.
Van Rood, et al., Reexposure of cord blood to non inherited maternal HLA antigens improves transplant outcome in hematological malignancies, Proc. Natl. Acad. Sci. USA, vol. 106, No. 47, 2009, pp. 19952-19957.
Varnum-Finney, et al., "Combined effects of Notch signaling and cytokines induce a multiple log increase in precursors with lymphoid and myeloid reconstituting ability," Blood, vol. 101, 2003, pp. 1784-1789.
Varnum-Finney, et al., "The Notch ligand, Jagged-1, influences the development of primitive hematopoietic precursor cells," Blood, vol. 91, 1998, pp. 4084-4091.
Wagner, et al., "Transplantation of Umbilical Cord Blood After Myeloablative Therapy: Analysis of Engraftment," Blood, vol. 79, No. 7, 1992, pp. 1874-1881.
Walker, et al., "The Notch/Jagged pathway inhibits proliferation of human hematopoietic progenitors in vitro," Stem Cells, vol. 17, 1999, pp. 162-171.

(56) References Cited

OTHER PUBLICATIONS

Washburn, et al., "Notch activity influences the alphabeta versus gammadelta T cell lineage decision," Cell, vol. 88, 1997, pp. 833-843.

* cited by examiner

FIG. 7

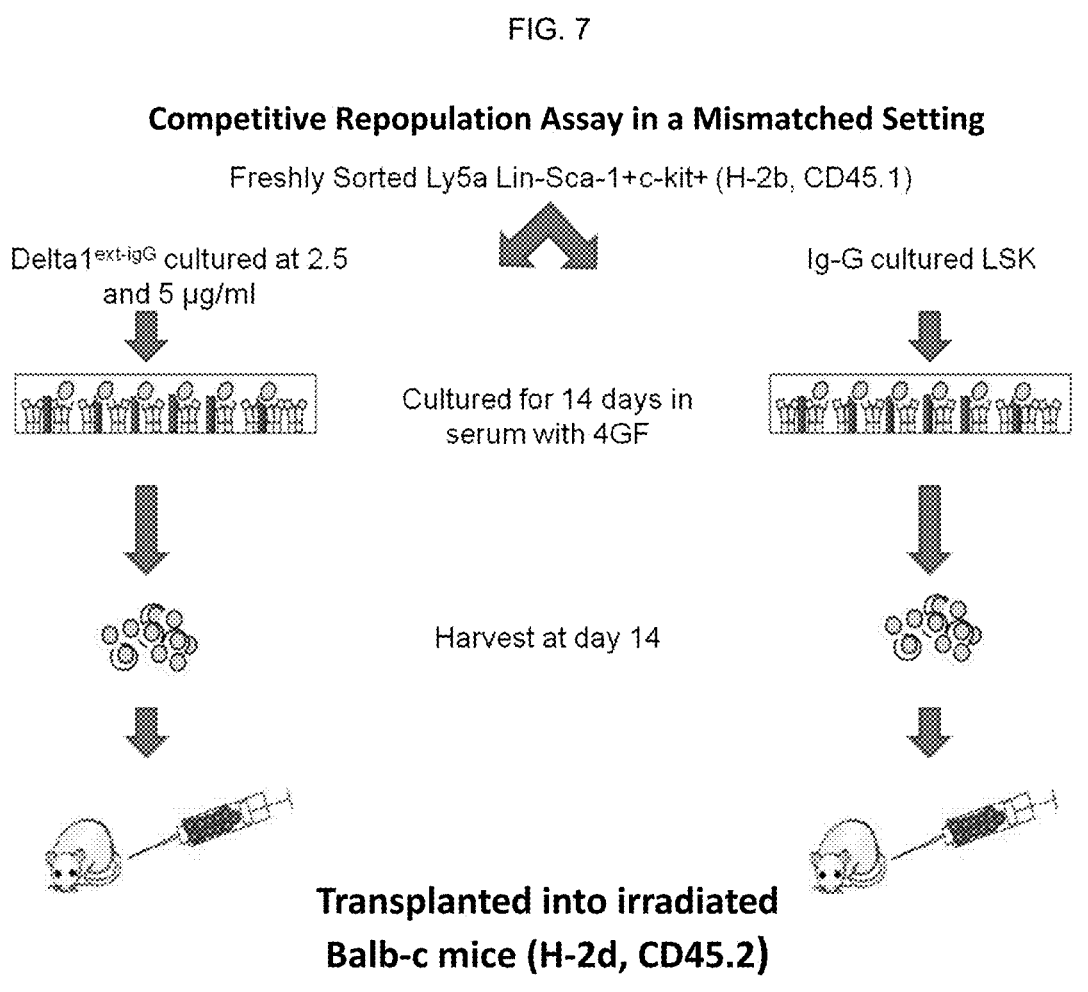

Competitive Repopulation Assay in a Mismatched Setting

Freshly Sorted Ly5a Lin-Sca-1+c-kit+ (H-2b, CD45.1)

Delta1$^{ext-IgG}$ cultured at 2.5 and 5 μg/ml

Ig-G cultured LSK

Cultured for 14 days in serum with 4GF

Harvest at day 14

Transplanted into irradiated Balb-c mice (H-2d, CD45.2)

FIG. 8A

EFFICACY – MURINE MODEL

Initial studies confirming that effective engraftment is achieved when expanded murine progenitors are infused in a mismatched setting after a single dose of radiation

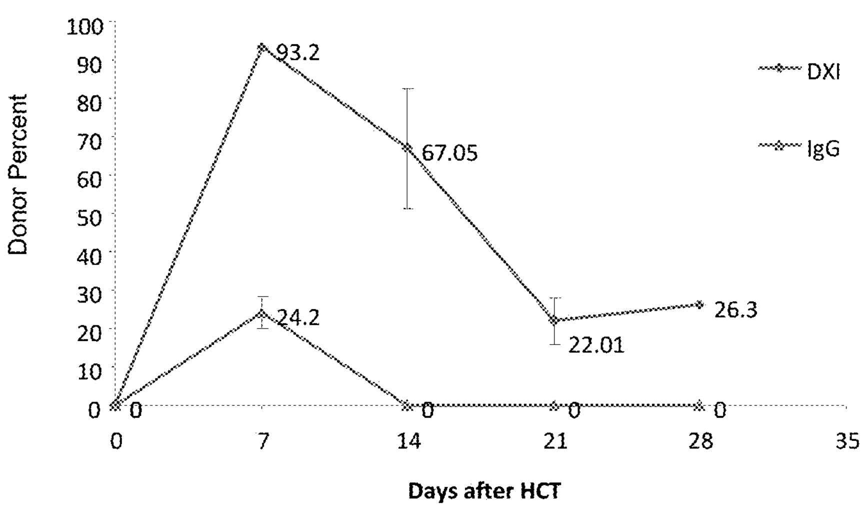

FIG. 8B

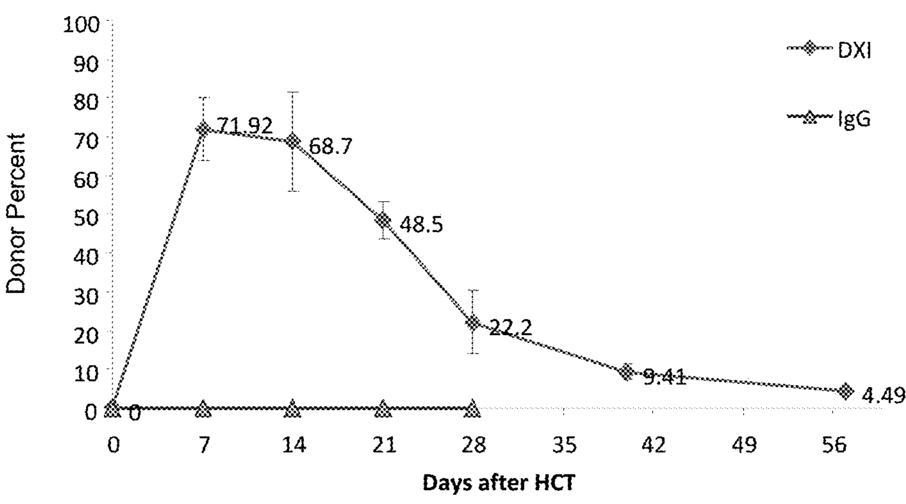

$LD_{100}$ radiation dose was chosen for these experiments to:

- evaluate whether expanded progenitors can prolong survival at a lethal dose of radiation
- to determine the maximum cell dose tolerated leading to improved survival
- to generate survival curves Radioprotection Assay Demonstrates Improved Survival with Infusion of Expanded Cryopreserved Cells

Days post infusion

ENHANCED SURVIVAL AFTER LETHAL RADIATION WITH INCREASING CELL DOSE

Level of Donor Engraftment is Enhanced with Increasing Dose of Radiation

FIG. 15

*Patient/Cells Characteristics*

Patients

| Total N | 9 |
|---|---|
| **Male/Female** | **2/3** |
| **Age (years)** | **55 (40 to 59)** |
| **Weight (kg)** | **87 (64 to 126)** |
| **Disease** | |
| **Relapsed** | **7** |
| **Primary refractory** | **2** |
| **Expanded cells (n=12, data n=10)** | |
| **CD34/kg (infused)** | **$8.8 \times 10^6$ (4.9 to 15.3)** |

Neutrophil recovery (chemo day)

| Patient | ANC >500 |
|---|---|
| Pt 1, cycle 1 | 22 |
| Pt 1, cycle 2 ** | 59 |
| Pt 2, cycle 1 | 18 |
| Pt 2, cycle 2** | 19 |
| Pt 3, cycle 1 | 27 |
| Pt 4, cycle 1 | 19 |
| Pt 4, cycle 2 ** | 18 |
| Pt 5, cycle 1 | 18 |
| Pt 6, cycle 1 | Blast recovery |
| Pt 7, cycle 1 | Blast recovery |
| Pt 8, cycle 1 | Pending |
| Pt 9, cycle 1 | Pending |

FIG. 16

*Expanded cell engraftment (% donor)*
*Day 7 post infusion of product (day 13 chemo)*

| Patient | CD33 | CD14 | CD56 | CD3 | Whole Blood | BM Chim |
|---|---|---|---|---|---|---|
| **Pt 1, Cy 1** | 0 | 0 | 0 | 0 | 0 | 0 |
| **Pt 1, Cy 2*** | 100 | 100 | 0 | 0 | 25 | 11 |
| **Pt 2, Cy 1** | 0 | 0 | 0 | 0 | 0 | 0 |
| **Pt 2, Cy 2**** | 85 | 100 | 0 | 0 | 30 | 3 |
| **Pt 3, Cy 1** | 0 | 0 | 0 | 0 | 0 | 0 |
| **Pt 4, Cy 1** | 0 | 0 | 0 | 0 | 0 | 0 |
| **Pt 5, Cy 1** | n/d | n/d | n/d | n/d | 0 | 0 (60% blasts) |
| **Pt 6, Cy 1** | 0 | 0 | 0 | 0 | 0 | 0 |
| **Pt 7, Cy 1** | 0 | 0 | 0 | 0 | 0 | 80-90% blasts |
| **Pt 8, Cy 1** | 43 | QNS | QNS | 0 | 23 | 22 |
| **Pt 9, Cy 1** | Too early post chemotherapy | | | | | |

*Cycle 2 started day 28 of cycle 1 ** Cycle 2 started day 40 of cycle 1

FIG. 20

| *Day 7 Peripheral BloodDNA Chimerism Analysis* | | | | | |
|---|---|---|---|---|---|
| | | **Patient 1** | **Patient 2** | **Patient 3** | **Patient 4** |
| **CD33** | **Expanded** | **100%** | **100%** | **100%** | **100%** |
| | Unmanipulated 1 | 0% | 0% | 0% | 0% |
| | Unmanipulated 2 | 0% | 0% | 0% | 0% |
| | Host | 0% | 0% | 0% | 0% |
| **CD14** | **Expanded** | **100%** | **97%** | **100%** | **98%** |
| | Unmanipulated 1 | 0% | 3% | 0% | 1% |
| | Unmanipulated 2 | 0% | 0% | 0% | 0% |
| | Host | 0% | 0% | 0% | 1% |
| **CD56** | **Expanded** | **11%** | **5%** | **11%** | **0%** |
| | Unmanipulated 1 | 79% | 60% | 63% | 42% |
| | Unmanipulated 2 | 0% | 35% | 20% | 56% |
| | Host | 11% | 0% | 6% | 2% |
| **CD19** | **Expanded** | QNS | QNS | QNS | QNS |
| | Unmanipulated 1 | | | | |
| | Unmanipulated 2 | | | | |
| | Host | | | | |
| **CD3** | **Expanded** | **0%** | **0%** | **0%** | **0%** |
| | Unmanipulated 1 | 43% | 81% | 83% | 53% |
| | Unmanipulated 2 | 34% | 8% | 1% | 19% |
| | Host | 23% | 11% | 16% | 28% |

COMPOSITIONS AND METHODS FOR PROVIDING HEMATOPOIETIC FUNCTION WITHOUT HLA MATCHING

CROSS-REFERENCE TO RELATED APPLICATIONS

This application is a continuation of U.S. application Ser. No. 13/640,297 filed Dec. 21, 2012, which is a national phase of International Application No. PCT/US2011/031953, filed Apr. 11, 2011, which claims benefit of U.S. Provisional Application No. 61/322,544, filed Apr. 9, 2010, each of which is incorporated by reference herein in its entirety.

STATEMENT OF GOVERNMENT SUPPORT

This invention was made with government support under HL101844 awarded by the National Institutes of Health and HHS010020080064C awarded by the Department of Health and Human Services. The government has certain rights in the invention.

1. FIELD OF THE INVENTION

The present invention relates to methods and compositions for providing hematopoietic function to human patients in need thereof, by selecting an expanded human umbilical cord blood stem/progenitor cell sample without taking into account the HLA-type of the expanded human cord blood stem cell/progenitor sample or the HLA-type of the patient; and administering the selected expanded human cord blood stem/progenitor cell sample to the patient. Methods for obtaining the expanded human cord blood stem/progenitor cell samples, banks of frozen expanded human umbilical cord blood stem/progenitor cell samples, and methods for producing such banks are also provided herein.

2. BACKGROUND OF THE INVENTION

Prolonged pancytopenia is common following intensive chemotherapy regimens, myeloablative and reduced intensity regimens for hematopoietic cell transplantation (HCT), and exposure to acute ionizing radiation. Of particular concern is prolonged neutropenia, which results in a significant risk of infection despite improved antimicrobial therapy and increases morbidity and mortality. Thus, novel therapies that can abrogate prolonged pancytopenia/neutropenia following high dose chemotherapy and/or radiation, and potentially facilitate more rapid hematopoietic recovery, are needed.

Expansion techniques for cord blood stem cells have been described. See, e.g., U.S. Pat. No. 7,399,633 B2 to Bernstein et al., and Delaney et al., 2010, Nature Med. 16(2): 232-236. Delaney et al. reported rapid engraftment after infusion of previously cryopreserved cord blood stem cells which had been selected on the basis of HLA matching, and which had been expanded ex vivo.

International Patent Publication No. WO 2006/047569 A2 discloses methods for expanding myeloid progenitor cells that do not typically differentiate into cells of the lymphoid lineage, and which can be MHC-mismatched with respect to the recipient of the cells.

International Patent Publication No. WO 2007/095594 A2 discloses methods for facilitating engraftment of hematopoietic stem cells by administering myeloid progenitor cells in conjunction with the hematopoietic stem cell graft, for example, where the hematopoietic stem cell graft is suboptimal because it has more than one MHC mismatch with respect to the cells of the recipient patient.

U.S. Pat. No. 5,004,681 to Boyse et al. discloses the use of human cord blood stem cells for hematopoietic reconstitution.

2.1 Human Leukocyte Antigen

The human leukocyte antigen system (HLA) is the name of the major histocompatibility complex (MHC) in humans. The superlocus contains a large number of genes related to immune system function in humans. This group of genes resides on chromosome 6, and encodes cell-surface antigen-presenting proteins and many other genes. The HLA genes are the human versions of the MHC genes that are found in most vertebrates (and thus are the most studied of the MHC genes). The proteins encoded by the HLA genes are also known as antigens, as a result of their historic discovery as factors in organ transplantations. The major HLA antigens are essential elements for immune function. Different classes have different functions.

HLA class I antigens (HLA-A, HLA-B and HLA-C) are transmembrane proteins that are expressed on the surface of almost all the cells of the body (except for red blood cells and the cells of the central nervous system) and present peptides on the cell surface, which peptides are produced from digested proteins that are broken down in the proteasomes.

HLA class II antigens (HLA-DP, HLA-DM, HLA-DOA, HLA-DOB, HLA-DQ, and HLA-DR) present antigens from outside of the cell to T-lymphocytes. These particular antigens stimulate T-helper cells to multiply, and these T-helper cells then stimulate antibody-producing B-cells to produce antibodies to that specific antigen. Self-antigens are suppressed by suppressor T-cells.

HLA class III antigens encode components of the complement system.

HLA antigens have other roles. They are important in disease defense. They may be the cause of organ transplant rejections. They may protect against or fail to protect against (if down regulated by an infection) cancers. They may mediate autoimmune disease, e.g., type I diabetes, coeliac disease). Also, in reproduction, HLA may be related to the individual smell of people and may be involved in mate selection.

Diversity of HLA in human population is one aspect of disease defense, and, as a result, the chance of two unrelated individuals having identical HLA molecules on all loci is very low. Thus, in the prior art, there was a need for HLA typing to determine suitable allele matching to avoid rejection of the donor tissue by the recipient or, in the case of hematopoietic stem cell transplants, to avoid the possibility of the donated hematopoietic cells from attacking the recipient. Most tissue typing is done using serological methods with antibodies specific for identified HLA antigens. DNA-based methods for detecting polymorphisms in the HLA antigen-encoding gene are also used for typing HLA alleles. Currently in the clinical setting for cord blood transplants, HLA typing of the donor tissue and the recipient concerns determining six HLA antigens or alleles, usually two each at the loci HLA-A, HLA-B and HLA-DR, or one each at the loci HLA-A, HLA-B and HLA-C and one each at the loci HAL-DRB1, HLA-DQB1 and HLA-DPB1 (see e.g., Kawase et al., 2007, Blood 110:2235-2241). HLA typing can be done (1) by determining the HLA allele, which is done on the DNA sequence level by determining the allele-specific sequences, and/or (2) by determining the HLA antigen serologically, by way of antibodies specific for the HLA-antigen.

2.2 Hematopoietic Stem Cells

The hematopoietic stem cell is pluripotent and ultimately gives rise to all types of terminally differentiated blood cells. The hematopoietic stem cell can self-renew, or it can differentiate into more committed progenitor cells, which progenitor cells are irreversibly determined to be ancestors of only a few types of blood cell. For instance, the hematopoietic stem cell can differentiate into (i) myeloid progenitor cells, which myeloid progenitor cells ultimately give rise to monocytes and macrophages, neutrophils, basophils, eosinophils, erythrocytes, megakaryocytes/platelets, dendritic cells, or (ii) lymphoid progenitor cells, which lymphoid progenitor cells ultimately give rise to T-cells, B-cells, and lymphocyte-like cells called natural killer cells (NK-cells). Once the stem cell differentiates into a myeloid progenitor cell, its progeny cannot give rise to cells of the lymphoid lineage, and, similarly, lymphoid progenitor cells cannot give rise to cells of the myeloid lineage. For a general discussion of hematopoiesis and hematopoietic stem cell differentiation, see Chapter 17, Differentiated Cells and the Maintenance of Tissues, Alberts et al., 1989, Molecular Biology of the Cell, 2nd Ed., Garland Publishing, New York, NY; Chapter 2 of Regenerative Medicine, Department of Health and Human Services, August 2006 (http://stemcells.nih.gov/info/scireport/2006report.htm), and Chapter 5 of Hematopoietic Stem Cells, 2009, Stem Cell Information, Department of Health and Human Services (http://stemcells.nih.gov/info/scireport/chapter5.asp).

In vitro and in vivo assays have been developed to characterize hematopoietic stem cells, for example, the spleen colony forming (CFU-S) assay and reconstitution assays in immune-deficient mice. Further, presence or absence of cell surface protein markers defined by monoclonal antibody recognition have been used to recognize and isolate hematopoietic stem cells. Such markers include, but are not limited to, Lin, CD34, CD38, CD43, CD45RO, CD45RA, CD59, CD90, CD109, CD117, CD133, CD166, and HLA DR, and combinations thereof. See Chapter 2 of Regenerative Medicine, Department of Health and Human Services, August 2006 (http://stemcells.nih.gov/info/scireport/2006report.htm) and the references cited therein.

2.3 Notch Pathway

Members of the Notch family encode large transmembrane proteins that play central roles in cell-cell interactions and cell-fate decisions during early development in a number of invertebrate systems (Simpson, 1995, Nature 375: 736-7; Artavanis-Tsakonas et al., 1995, Science. 268:225-232; Simpson, 1998, Semin. Cell Dev. Biol. 9:581-2; Go et al., 1998, Development. 125:2031-2040; Artavanis-Tsakonas and Simpson, 1991, Trends Genet. 7:403-408). The Notch receptor is part of a highly conserved pathway that enables a variety of cell types to choose between alternative differentiation pathways based on those taken by immediately neighboring cells. This receptor appears to act through an undefined common step that controls the progression of uncommitted cells toward the differentiated state by inhibiting their competence to adopt one of two alternative fates, thereby allowing the cell either to delay differentiation, or in the presence of the appropriate developmental signal, to commit to differentiate along the non-inhibited pathway.

Genetic and molecular studies have led to the identification of a group of genes which define distinct elements of the Notch signaling pathway. While the identification of these various elements has come exclusively from *Drosophila* using genetic tools as the initial guide, subsequent analyses have led to the identification of homologous proteins in vertebrate species including humans. The molecular relationships between the known Notch pathway elements as well as their subcellular localization are depicted in Artavanis-Tsakonas et al., 1995, Science 268:225-232; Artavanis-Tsakonas et al., 1999, Science 284:770-776; and in Kopan et al., 2009, Cell 137:216-233. Delta and Serrate (or Jagged, the mammalian homolog of Serrate) are extracellular ligands of Notch. The portion of Delta and Serrate ("Serrate" shall be used herein to refer to both *Drosophila* Serrate and its mammalian homolog, Jagged) responsible for binding to Notch is called the DSL domain, which domain is located in the extracellular domain of the protein. Epidermal growth factor-like repeats (ELRs) 11 and 12 in the extracellular domain of Notch are responsible for binding to Delta, Serrate and Jagged. See Artavanis-Tsakonas et al., 1995, Science 268:225-232 and Kopan et al., 2009, Cell 137:216-233.

2.4 Notch Pathway in Hematopoiesis

Evidence of Notch-1 mRNA expression in human $CD34^+$ precursors has led to speculation for a role for Notch signaling in hematopoiesis (Milner et al., 1994, Blood 3:2057-62). This is further supported by the demonstration that Notch-1 and -2 proteins are present in hematopoietic precursors, and, in higher amounts, in T cells, B cells, and monocytes, and by the demonstration of Jagged-1 protein in hematopoietic stroma (Ohishi et al., 2000, Blood 95:2847-2854; Varnum-Finney et al., 1998, Blood 91:4084-91; Li et al., 1998, Immunity 8:43-55).

The clearest evidence for a physiologic role of Notch signaling has come from studies of T cell development which showed that activated Notch-1 inhibited B cell maturation but permitted T cell maturation (Pui et al., 1999, Immunity 11:299-308). In contrast, inactivation of Notch-1 or inhibition of Notch-mediated signaling by knocking out HES-1 inhibited T cell development but permitted B cell maturation (Radtke et al., 1999, Immunity 10: 47-58; Tomita et al., 1999, Genes Dev. 13:1203-10). These opposing effects of Notch-1 on B and T cell development raise the possibility that Notch-1 regulates fate decisions by a common lymphoid progenitor cell.

Other studies in transgenic mice have shown that activated Notch-1 affects the proportion of cells assuming a CD4 vs. CD8 phenotype as well as an $\alpha\beta$ vs. $\gamma\delta$ cell-fate (Robey et al., 1996, Cell 87:483-92; Washburn et al., 1997, Cell 88:833-43). Although this may reflect an effect on fate decisions by a common precursor, more recent studies have suggested that these effects may result from an anti-apoptotic effect of Notch-1 that enables the survival of differentiating T cells that would otherwise die (Deftos et al., 1998, Immunity 9:777-86; Jehn et al., 1999, J Immunol. 162:635-8).

Studies have also shown that the differentiation of isolated hematopoietic precursor cells can be inhibited by ligand-induced Notch signaling. Co-culture of murine marrow precursor cells ($Lin^-$ $Sca\text{-}1^+c\text{-}kit^+$) with 3T3 cells expressing human Jagged-1 led to a 2 to 3 fold increase in the formation of primitive precursor cell populations (Varnum-Finney et al., 1998, Blood 91:4084-4991; Jones et al., 1998, Blood 92:1505-11). Incubation of sorted precursors with beads coated with the purified extracellular domain of human Jagged-1 also led to enhanced generation of precursor cells (Varnum-Finney et al., 1998, Blood 91:4084-91).

In a study of human $CD34^+$ cells, expression of the intracellular domain of Notch-1 or exposure to cells that overexpressed Jagged-2 also led to enhanced generation of precursor cells and prolonged maintenance of CD34 expression (Carlesso et al., 1999, Blood 93:838-48). In another study, the effects of Jagged-1-expressing cells on $CD34^+$ cells were influenced by the cytokines present in the cultures; in the absence of added growth factors, the interaction with cell-bound Jagged-1 led to maintenance of $CD34^+$ cells in a non-proliferating, undifferentiated state, whereas the addition of c-kit ligand led to a 2-fold increase in erythroid colony-forming cells (Walker et al., 1999, Stem Cells 17:162-71).

Varnum-Finney et al., 1993, Blood 101:1784-1789 demonstrated that activation of endogenous Notch receptors in mouse marrow precursor cells by an immobilized Notch ligand revealed profound effects on the growth and differentiation of the precursor cells, and that a multilog increase in the number of precursor cells with short-term lymphoid and myeloid repopulating ability was observed. Delaney et al., 2005, Blood 106:2693-2699 and Ohishi et al., 2002, J. Clin. Invest. 110:1165-1174 demonstrated that incubation of human cord blood progenitors in the presence of an immobilized Notch ligand generated an approximate 100-fold increase in the number of $CD34^+$ cells with enhanced repopulating ability as determined in an immunodeficient mouse model. See also U.S. Pat. No. 7,399,633 B2.

Delaney et al., 2010, Nature Med. 16(2): 232-236 demonstrated that a population of $CD34^+$ cells obtained from a frozen cord blood sample, which population had been cultured in the presence of a Notch ligand (resulting in a greater than 100 fold increase in the number of $CD34^+$ cells), repopulated immunodeficient mice with markedly enhanced kinetics and magnitude, and provided more rapid myeloid engraftment in humans in a clinical phase 1 myeloablative cord blood transplant trial.

Citation or identification of any reference in Section 2 or any other section of this application shall not be construed as an admission that such reference is available as prior art to the present invention.

3. SUMMARY OF THE INVENTION

There exists a need in the art for an "off-the-shelf" product for rapid hematopoietic reconstitution without the need for HLA matching, that could be stockpiled long term after manufacture. The present invention fulfills such a need. The present invention provides methods for providing hematopoietic function to a human patient in need thereof, comprising administering an expanded human cord blood stem cell sample to the patient, wherein said administering is done without matching the HLA-type of the expanded human cord blood stem cell sample to the HLA-type of the patient. The present invention also provides methods for providing hematopoietic function to a human patient in need thereof, comprising: (a) selecting an expanded human cord blood stem cell sample for administration to the patient, wherein said selecting does not take into account the HLA-type of the sample or the HLA-type of the patient; and (b) administering the selected sample to the patient. In a specific embodiment, at least one HLA antigen or allele is different between the expanded human cord blood stem cell sample and the patient, among those antigens or alleles HLA-typed, respectively. In another specific embodiments, the expanded cord blood stem cell sample and the patient are different at two, three, four, five, six or more HLA antigens or alleles, among those antigens or alleles, HLA-typed, respectively. In yet another embodiment, the expanded human cord blood stem cell sample administered to the patient contains at least 75 million viable $CD34^+$ cells, preferably at least 250 million viable $CD34^+$ cells.

In one embodiment, the expanded human cord blood stem cell sample of the present invention has been subjected to an expansion technique that has been shown to result in an at least 50-fold increase in hematopoietic stem cells or hematopoietic stem and progenitor cells in an aliquot of a human cord blood stem cell sample subjected to the expansion technique, relative to an aliquot of the human cord blood stem cell sample prior to being subjected to the expansion technique. The hematopoietic stem cells or the hematopoietic stem and progenitor cells can be positive for one or more of the following cell surface markers expressed in increased levels on hematopoietic stem cells or hematopoietic stem and progenitor cells, relative to other types of hematopoietic cells: CD34, CD43, CD45RO, CD45RA, CD59, CD90, CD109, CD117, CD133, CD166, and HLA DR and/or negative for Lin and/or CD38 cell surface markers. Preferably, the hematopoietic stem cells or hematopoietic stem and progenitor cells are positive for one or more of CD34, CD133 or CD90 cell surface markers. Preferably, the expanded human cord blood stem cell sample of the present invention has been subjected to an expansion technique that has been shown (i) to result in an at least 50-fold increase in $CD34^+$ cells in an aliquot of a human cord blood stem cell sample subjected to the expansion technique, relative to an aliquot of the human cord blood stem cell sample prior to being subjected to the expansion technique; or (ii) to increase the number of SCID repopulating cells in a human cord blood stem cell sample subject to the expansion technique, relative to the human cord blood cell stem cell sample prior to being subject to the expansion technique.

In particular embodiments, the expanded human cord blood stem cell sample is frozen and thawed prior to administering to the patient.

In a specific embodiment, the expanded human cord blood stem cell sample that is administered is a pool of two or more expanded human cord blood stem cell samples, each sample obtained from a different human at birth. Optionally, the HLA-types of at least two samples in the pool are HLA-mismatched, i.e., wherein at least one HLA antigen or allele typed in the samples is different. Optionally, the expanded human cord blood stem cell sample is a pool of two or more human cord blood stem cell samples pooled prior to, or after, expansion, which pool is then expanded according to the invention. In one embodiment, the samples in the pool are all derived from umbilical cord blood and/or placental blood of individuals of the same race, e.g., African-American, Caucasian, Asian, Hispanic, Native-American, Australian Aboriginal, Inuit, Pacific Islander, or are all derived from umbilical cord blood and/or placental blood of individuals of the same ethnicity, e.g., Irish, Italian, Indian, Japanese, Chinese, Russian, etc. Preferably, pooling of the samples is done without regard to the HLA type of the samples.

In yet another embodiment, the method of providing hematopoietic function comprises, prior to said administering, a step of expanding ex vivo isolated human cord blood stem cells, or stem and progenitor cells, obtained from the umbilical cord blood and/or placental blood of one or more humans at birth. Preferably, the expanding step comprises contacting the human cord blood stem cells, or stem and progenitor cells, with an agonist of Notch function. The agonist can be a Delta protein or a Serrate protein, or a fragment of a Delta protein or Serrate protein, which fragment is able to bind a Notch protein.

In a particular embodiment of the present invention, a method for providing hematopoietic function to a human patient in need thereof is provided, which method comprises (a) enriching for hematopoietic stem cells, or hematopoietic stem and progenitor cells, from isolated human cord blood stem cells or stem and progenitor cells obtained from the umbilical cord blood and/or placental blood of one or more humans at birth to produced enriched hematopoietic stem cells or hematopoietic stem and progenitor cells; (b) expanding ex vivo the enriched hematopoietic stem cells or hematopoietic stem and progenitor cells to produce an expanded stem cell sample; and (c) administering the expanded stem cell sample to a human patient in need thereof, wherein said administering is done without matching the HLA type of the expanded cell sample to the HLA-type of the patient. In a preferred embodiment, the expanded cells are $CD34^+$ cells. In another preferred embodiment, the expanded cells are $CD133^+$ cells. In another preferred embodiment, the expanded cells are $CD90^+$ cells. In yet another embodiment, the expanded cells are positive for one or more of the following cell surface markers expressed in increased levels on hematopoietic stem cells or hematopoietic stem and progenitor cells, relative to other types of hematopoietic cells: CD34, CD43, CD45RO, CD45RA, CD59, CD90, CD109, CD117, CD133, CD166, and HLA DR and/or negative for Lin and/or CD38 cell surface markers. Preferably, the expanded cells are positive for one or more of CD34, CD133 or CD90 cell surface markers. This method can further comprise the steps of freezing and thawing the expanded cell sample after step (b) and before step (c). In certain embodiments, the patient suffers from pancytopenia or neutropenia, wherein the pancytopenia or neutropenia is caused by an intensive chemotherapy regimen, a myeloablative regimen for hematopoietic cell transplantation, or exposure to acute ionizing radiation.

In another embodiment, the present invention provides a method of producing a bank of frozen expanded human cord blood stem cells comprising the following steps in the order stated: (a) expanding, ex vivo, isolated human cord blood stem cells, or stem and progenitor cells, obtained from the umbilical cord blood and/or placental blood of one or more humans at birth of said individual to produce an expanded human cord blood stem cell sample; (b) freezing the expanded human cord blood stem cell sample to produce a frozen expanded human cord blood stem cell sample; (c) storing the frozen expanded human cord blood stem cell sample; and (d) repeating steps (a)-(c) at least 50 times to produce a bank of at least 50 stored, frozen, expanded human cord blood stem cell samples. In specific embodiments, steps (a)-(c) are repeated at least 5, 10, 20, 25, 50, 75, 100, 200, 250, 500, 750, 1000, 1500, 2,000, 3,000, 5,000, 7,500, 10,000, 25,000, 50,000 or 100,000 times to produce the corresponding number of stored, frozen, expanded human cord blood stem cell samples. In one embodiment, the method further comprises prior to step (b) pooling one or more expanded human cord blood stem cell samples. In one embodiment, the method further comprises a step of assigning each frozen expanded human cord blood stem cell sample an identifier that distinguishes the frozen expanded human cord blood stem cell sample from other frozen expanded stem cell samples. In another embodiment, the method further comprises a step of storing the identifier in one or more computer databases, wherein said stored identifier is associated with information on the physical location where the frozen expanded human cord blood stem cell sample is stored in said bank. The present invention is also directed to a blood bank comprising at least 50 units of frozen expanded human cord blood stem cell samples. In specific embodiments, the blood bank comprises at least 5, 10, 20, 25, 50, 75, 100, 200, 250, 500, 750, 1000, 1500, 2,000, 3,000, 5,000, 7,500, 10,000, 25,000, 50,000 or 100,000 units of frozen expanded human cord blood stem cells.

In another embodiment of the invention, a computer-implemented method for selecting a frozen expanded human cord blood stem cell sample for use in providing hematopoietic function to a human patient in need thereof is provided, which method comprises (a) selecting an identifier from a plurality of at least 50 identifiers stored in a computer database, each identifier identifying a frozen stored expanded human cord blood stem cell sample derived from the umbilical cord blood and/or placental blood of one or more humans birth, wherein the selecting does not take into account the respective HLA types of the stored frozen expanded human cord blood stem cell samples corresponding to the respective identifiers, wherein the selecting is for administration of the expanded human cord blood stem cell sample identified by said identifier to a human patient in need thereof; and (b) outputting or displaying the selected identifier. In specific embodiments, the identifier is outputted or displayed to a user, an internal or external component of a computer, a remote computer, or to storage on a computer readable medium. In another specific embodiment, the outputting or displaying further outputs or displays information on the physical location of the expanded human cord blood stem cell sample identified by the identifier. In yet another embodiment, the computer-implemented method further comprises implementing robotic retrieval of the identified, frozen, expanded human cord blood stem cell sample.

In another embodiment of the invention, a computer program product is provided for use in conjunction with a computer system, which computer program product comprises a computer readable storage medium and a computer program mechanism embedded therein, the computer program mechanism comprising (a) executable instructions for selecting an identifier from a plurality of at least 50 identifiers stored in a computer database, each identifier identifying a frozen, stored, expanded human cord blood stem cell sample derived from the umbilical cord blood and/or placental blood of one or more humans at birth, wherein the selecting does not take into account the respective HLA types of the frozen, stored, expanded human cord blood stem cell samples corresponding to the respective identifiers, wherein the selecting is for administration of the expanded human cord blood stem cell sample identified by said identifier to a human patient in need thereof; and (b) executable instructions for outputting or displaying the selected identifier. In particular embodiments, the identifier is outputted or displayed to a user, an internal or external component of a computer, a remote computer, or to storage on a computer readable medium.

In yet another embodiment, the present invention provides an apparatus comprising a processor; a memory, coupled to the processor, the memory storing a module, the module comprising (a) executable instructions for selecting an identifier from a plurality of at least 50 identifiers stored in a computer database, each identifier identifying a frozen stored expanded human cord blood stem cell sample derived from the umbilical cord blood and/or placental blood of one or more humans at birth, wherein the selecting does not take into account the respective HLA types of the stored frozen expanded human cord blood stem cell samples corresponding to the respective identifiers, wherein the selecting is for administration of the expanded human cord blood stem cell sample identified by said identifier to a human patient in need thereof; and (b) executable instructions for outputting or displaying the selected identifier. In particular embodiments, the identifier is outputted or displayed to a user, an internal or external component of a computer, a remote computer, or to storage on a computer readable medium.

4. DEFINITIONS

Although any methods and materials similar or equivalent to those described herein can be used in the practice or testing of the present invention, the preferred methods and materials are described. For purposes of the present invention, the following terms are defined below.

As used herein, the term "CB Stem Cells," referred to herein interchangeably as "a CB Stem Cell Sample," refers to a population enriched in hematopoietic stem cells, or enriched in hematopoietic stem and progenitor cells, derived from human umbilical cord blood and/or human placental blood collected at birth. The hematopoietic stem cells, or hematopoietic stem and progenitor cells, can be positive for a specific marker expressed in increased levels on hematopoietic stem cells or hematopoietic stem and progenitor cells, relative to other types of hematopoietic cells. For example, such markers can be, but are not limited to CD34, CD43, CD45RO, CD45RA, CD59, CD90, CD109, CD117, CD133, CD166, HLA DR, or a combination thereof. Also, the hematopoietic stem cells, or hematopoietic stem and progenitor cells, can be negative for an expressed marker, relative to other types of hematopoietic cells. For example, such markers can be, but are not limited to Lin, CD38, or a combination thereof. Preferably, the hematopoietic stem cells, or hematopoietic stem and progenitor cells, are $CD34^+$ cells.

As used herein, "Expanded CB Stem Cells," referred to herein interchangeably as "an Expanded CB Stem Cell Sample," refers to CB Stem Cells that have been subjected to a technique for expanding the cord blood hematopoietic stem cells, or hematopoietic stem and progenitor cells, which technique has been shown to result in (i) an increase in the number of hematopoietic stem cells, or hematopoietic stem and progenitor cells, in an aliquot of the sample thus expanded, or (ii) an increased number of SCID repopulating cells determined by limiting-dilution analysis as shown by enhanced engraftment in NOD/SCID mice infused with an aliquot of the sample thus expanded; relative to that seen with an aliquot of the sample that is not subjected to the expansion technique. In a specific embodiment, the enhanced engraftment in NOD/SCID mice can be detected by detecting an increased percentage of human CD45+ cells in the bone marrow of mice infused with an aliquot of the expanded sample relative to mice infused with an aliquot of the sample prior to expansion, at, e.g., 10 days, 3 weeks or 9 weeks post-infusion (see Delaney et al., 2010, Nature Med. 16(2): 232-236). In a specific embodiment, the expansion technique results in an at least 50-, 75-, 100-, 150-, 200-, 250-, 300-, 350-, 400-, 450-, or 500-fold increase in the number of hematopoietic stem cells or hematopoietic stem and progenitor cells, in an aliquot of the sample expanded, and preferably is a 100-200 fold increase.

5. BRIEF DESCRIPTION OF THE DRAWINGS

FIG. 1 illustrates an exemplary embodiment of a computer system useful for implementing the methods of the present invention.

FIGS. 2*a*-2*b* are graphs showing SCID repopulating frequency with cord blood cells cultured with Delta1$^{ext\text{-}IgG}$ generates a significant increase in the SRC frequency and improved overall engraftment. Sublethally irradiated NOD/SCID mice were transplanted with non-cultured $CD34^+$ cord blood cells or the progeny of $CD34^+$ cells cultured for 17 days on Delta1$^{ext\text{-}IgG}$ or control human IgG1 in 5 independent experiments. Human engraftment (CD45%) was measured at 3 (marrow aspiration from knee joint) and 9 (sacrificed and marrow harvested from bilateral femurs and tibiae) weeks. (FIG. 2*a*) Limiting dilution transplants were carried out as described above to calculate the SRC frequency, shown as the SRC frequency per 106 starting cells. Results are the mean±SEM. *P values shown represent Delta1$^{ext\text{-}IgG}$ cultured cells compared to control cultured or non-cultured cells. (FIG. 2*b*) Human engraftment as measured by total CD45%, lymphoid subset $CD19^+/CD45^+$ cells (black) and myeloid subset of $CD33^+/CD45^+$ double positive cells.

FIG. 3 is a graph showing that rapid early engraftment is dependent upon culture with Delta1$^{ext\text{-}IgG}$. $CD34^+$ cord blood progenitors were cultured with Delta1$^{ext\text{-}IgG}$ and compared to non-cultured cells for NOD/SCID repopulating ability. Human engraftment (CD45%) in the marrow was assessed 10 days and 3 weeks after infusion of the cells. Results shown are the mean CD45%±sem and is representative of one of two experiments where early engraftment was assessed.

FIGS. 4*a*-4*c* show that cryopreservation of ex vivo expanded cord blood progenitors does not impair in vivo repopulating ability. Overall human engraftment as measured by human CD45 in the marrow of recipient mice is shown on the y axis. The solid lines represent the mean level of human engraftment. (FIG. 4*a*) Cells infused immediately post culture compared with harvested cells that were cryopreserved prior to infusion. Results shown are at 4 weeks post infusion. (FIG. 4*b*) Ex vivo expanded and cryopreserved progenitor cells were thawed and infused. The figure represents the combined results of two experiments. (FIG. 4*c*) The expanded progeny derived from expansion of $CD34^+$ progenitors obtained from a single cord blood unit were divided into equal groups and cryopreserved per standard practice. Three methods of thawing prior to infusion were then compared for in vivo repopulating ability: thaw and wash, thaw and dilute (albumin/dextran dilution), thaw and direct infusion.

FIG. 5 shows a comparison of engraftment of Delta1$^{ext\text{-}IgG}$ cultured cells in congenic and allogeneic hematopoietic stem cells transplants (HCTs). LSK cells were cultured on Delta1$^{ext\text{-}IgG}$ for 4 weeks as described in Dallas et al., 2007 Blood 109:3579-3587. In the congenic HCT, lethally irradiated (1000 cGY) C57 (H-2d) mice received 105 C57 whole BM+106 Delta1$^{ext\text{-}IgG}$-cultured cells. In the allogeneic HCT, lethally irradiated (1000 cGy) BALB.c (H-2d) mice received 105 BALB.c whole BM+106 Delta1$^{ext/IgG}$-cultured cells. Blood was analyzed by FACS analysis at 2, 3, 5, and 7 weeks after HCT. N=5-7.

FIG. 6 shows engraftment of Delta1$^{ext\text{-}IgG}$-cultured cells in HLA-mismatched recipients. LSK cells were cultured for 4 weeks as described in Ohisi et al., 2002, J. Clin. Invest. 110:1165-1174 and Dallas et al., 2007 Blood 109:3579-3587. Lethally irradiated BALB.c (H-2d, CD45.2) recipients received 106 Ly5.1 (H-2b, CD45.1) Delta1$^{ext\text{-}IgG}$-cultured LSK cells along with 103 BALB.c (H-2d, CD45.2) LSK cells or 103 Ly5.1 (H-2b, CD45.1) LSK cells+103 BALB.c (H-2d, CD45.2). Mice were sacrificed at day 3 and 7; bone marrow engraftment was determined by FAC analysis (n=5).

FIG. 7 is a schematic drawing of the experimental protocol for expansion of stem and progenitor cells and infusion of the expanded cells into irradiated mice, in order to compare engraftment of the expanded stem and progenitor cells with non-expanded stem and progenitor cells.

FIGS. 8*a*-8*b* graphically show the engraftment of mismatched expanded stem and progenitor cells as detected in bone marrow and in peripheral blood of lethally irradiated mice.

FIGS. 9*a*-9*b* show the overall survival of mice exposed to 7.5 Gy or 8 Gy of radiation after infusion with expanded stem and progenitor cells that were previously cryopreserved, as compared to a control saline group.

FIG. 10 depicts the overall survival of mice irradiated at 8.5 Gy after infusion of expanded stem and progenitor cells (cultured with a Delta derivative) as compared to infusion of non-expanded cord blood stem and progenitor cells (IgG cultured).

FIGS. 11*a*-11*b* show that donor engraftment of expanded murine stem and progenitor cells (DXI) is enhanced with an increasing dose of radiation.

FIG. 12 shows clinical grade culture of cord blood progenitors with Delta1$^{ext-IgG}$ results in significant in vitro expansion of $CD34^+$ cells and more rapid neutrophil recovery in a myeloablative double CBT setting. $CD34^+$ cord blood progenitor cells were enriched and placed into culture with Delta1$^{ext-IgG}$. The individual and median times (solid line) to absolute neutrophil counts (ANC) of ≥500/μl for patients receiving double unit cord blood transplants with two non-manipulated units ("conventional") versus with one ex vivo expanded unit and one non-manipulated unit ("expanded") is presented.

FIG. 15 is a chart setting forth the characteristics of the patients treated, and infused cell count and neutrophil recovery time.

FIG. 16 is a chart depicting expanded cord blood stem and progenitor cell engraftment expressed as a percentage of donor cells at day 7 post-infusion of the expanded cord blood stem and progenitor cell sample.

FIG. 20 is a chart depicting the results of a peripheral blood cell DNA chimerism analysis at day 7 post-infusion (QNS, quantity not sufficient).

6. DETAILED DESCRIPTION OF THE INVENTION

Figure 1:
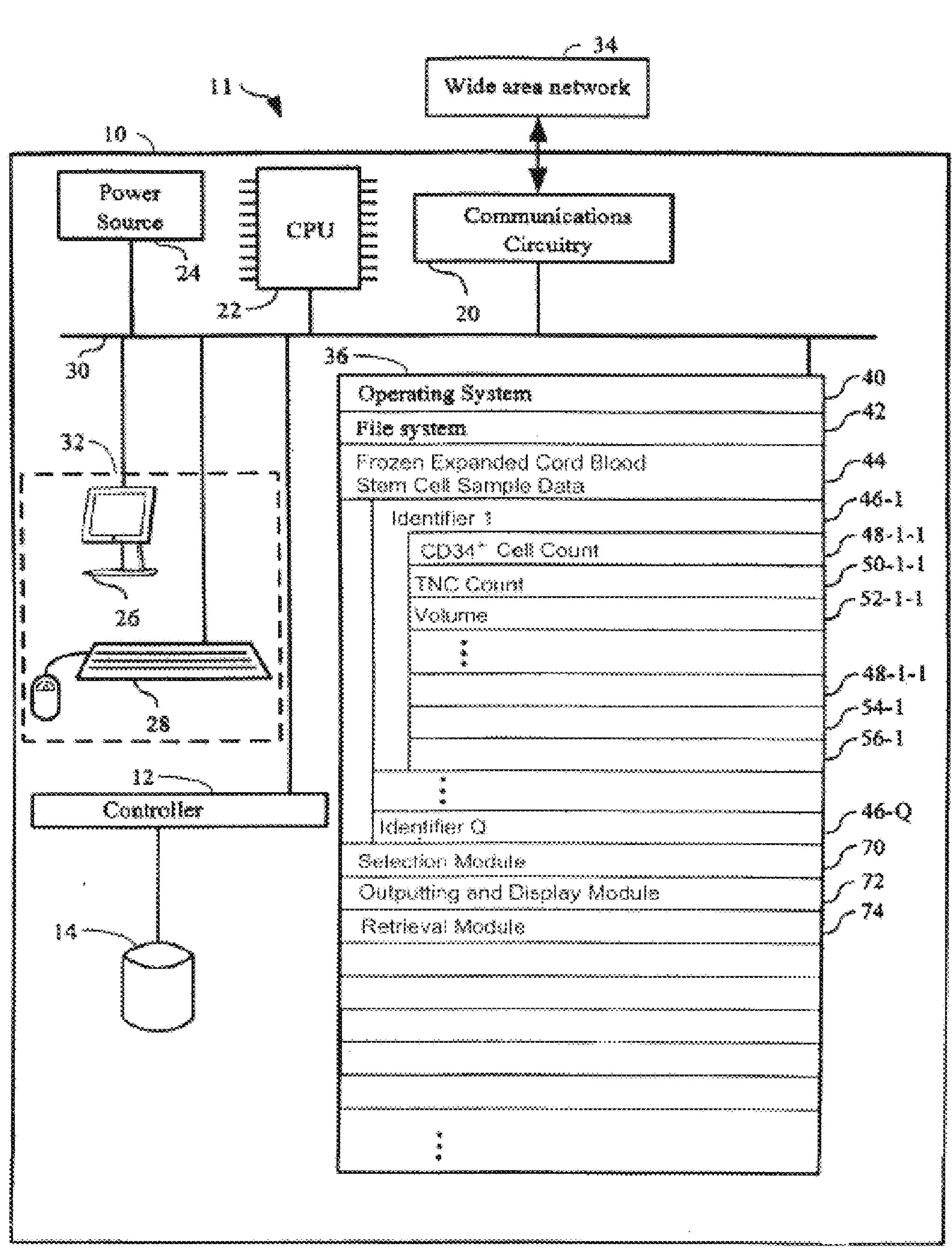

The present invention provides a method for providing hematopoietic function to a human patient in need thereof by administering an expanded human cord blood stem cell sample to the patient, wherein said administering is done without matching the HLA-type of the expanded human cord blood stem cell sample to the HLA type of the patient. By "without matching the HLA-type," what is meant is that no steps are taken to have any of the HLA antigens or alleles match between the patient and the sample. In one embodiment, the expanded human cord blood stem cells can differentiate into cells of the myeloid lineage. In another embodiment, the expanded human cord blood stem cell can differentiate into cells of the lymphoid lineage. The selection of the Expanded CB Stem Cells to be administered to the patient is done without taking into account whether the patient to whom the Expanded CB Stem Cells will be administered matches or mismatches the Expanded CB Stem Cells at any of the HLA antigens or alleles.

The ideal therapeutic product for treatment of chemotherapy or radiation induced pancytopenia is one that, when infused, would give rise to rapid hematopoietic reconstitution, especially of granulocytes, and also facilitate autologous recovery of hematopoiesis. Moreover, in order to be delivered in an expedited fashion, it is essential that the therapeutic product be developed as on "off-the-shelf" product that could be stockpiled long term after generation (manufacture). Hypothetically, while marrow or mobilized peripheral blood stem cells could provide a transient population of blood cells that could be infused to help mitigate pancytopenia that results from high dose chemotherapy/radiation, these would require HLA-matching for use, and procurement of these cells would not be easy or amenable to stockpiling. Similarly, the collection and use of granulocytes for transfusion as treatment for infection occurring in the setting of prolonged neutropenia is not promising. Current evidence indicates relatively little or no effect of granulocyte transfusions, possibly due to a limited lifespan (hours) of the cells infused and absence of in vivo generation of additional cells (not a renewable source of cells).

Prior to the present invention, it was not appreciated that Expanded CB Stem Cells could provide hematopoietic benefit to a human patient irrespective of HLA matching, since it was believed that the host immune response against the graft would destroy the potential therapeutic benefit. The present invention takes advantage of the prompt hematopoietic benefit provided by the Expanded CB Stem Cells to provide a benefit to a human patient even if the Expanded CB Stem Cells and the patient are HLA mismatched. While not being bound by any mechanism, it is believed that the Expanded CB Stem Cells can provide therapeutic benefit in a mismatch setting because the rapidity of engraftment provided by these cells allows for a beneficial effect on hematopoietic function before GVHD can develop and obviate such effect. Also, the increased hematopoietic cell numbers (including stem and progenitor cells) provided by the expansion methods described herein are believed to overcome, at least temporarily, host resistance to foreign cells. Additionally, other cell types generated in the expanded population, such as dendritic cell or natural killer (NK) cell precursors, is believed to prevent rejection of the infused cells by the host. Thus, provision of hematopoietic function can be achieved even in a mismatched setting, and administration to a patient can be therapeutic regardless of whether the patient and the expanded cord blood stem cell sample are HLA-matched.

Frequent infections are a common complication of induction chemotherapy and salvage regimens used in the treatment of hematopoietic malignancies, and in fact are a leading cause of treatment failure. The chemotherapeutic agents also can be profoundly immunosuppressive and/or highly myelosuppressive, which can lead to periods of prolonged neutropenia. Infusion of the Expanded CB Stem Cells of the invention can provide a therapeutic benefit in overcoming these challenges by abrogating neutropenia, preventing infectious complications, and facilitating host hematopoietic recovery post-chemotherapy.

Moreover, since according to the present invention, matching of HLA-type is not necessary for therapeutic use of the Expanded CB Stem Cells, it is now practical to store frozen Expanded CB Stem Cells, since the present invention teaches that useful amounts can practically be stored. In the prior art, since it was expected that HLA matching to the recipient would generally be necessary to find a useful sample of Expanded CB Stem Cells for therapeutic use, an unattainably large number of different Expanded CB Stem Cell samples had to be stored to make it feasible generally to find a match for a patient, the large numbers making it impractical to store expanded samples, due to the even larger amount of storage space needed to store expanded units. In contrast, and in accordance with the present invention, no HLA matching is required, and thus, the generation of a "bank" of CB Stem Cells which have been expanded and then cryopreserved, useful for the general human population to use in stem cell transplantation, is feasible, since any Expanded CB Stem Cell sample in the bank could feasibly be used with any recipient in a therapeutic method of the invention.

6.1 Collecting Cord Blood

Human umbilical cord blood and/or human placental blood are sources of the CB Stem Cells according to the present invention. Such blood can be obtained by any method known in the art. The use of cord or placental blood as a source of Stem Cells provides numerous advantages, including that the cord and placental blood can be obtained easily and without trauma to the donor. See, e.g., U.S. Pat. No. 5,004,681 for a discussion of collecting cord and placental blood at the birth of a human. In one embodiment, cord blood collection is performed by the method disclosed in U.S. Pat. No. 7,147,626 B2 to Goodman et al. Collections should be made under sterile conditions. Immediately upon collection, cord or placental blood should be mixed with an anticoagulant. Such an anticoagulant can be any known in the art, including but not limited to CPD (citrate-phosphate-dextrose), ACD (acid citrate-dextrose), Alsever's solution (Alsever et al., 1941, N. Y. St. J. Med. 41:126), De Gowin's Solution (De Gowin, et al., 1940, J. Am. Med. Ass. 114:850), Edglugate-Mg (Smith, et al., 1959, J. Thorac. Cardiovasc. Surg. 38:573), Rous-Turner Solution (Rous and Turner, 1916, J. Exp. Med. 23:219), other glucose mixtures, heparin, ethyl biscoumacetate, etc. See, generally, Hum, 1968, Storage of Blood, Academic Press, New York, pp. 26-160). In one embodiment, ACD can be used.

The cord blood can preferably be obtained by direct drainage from the cord and/or by needle aspiration from the delivered placenta at the root and at distended veins. See, generally, U.S. Pat. No. 5,004,681. Preferably, the collected human cord blood and/or placental blood is free of contamination.

In certain embodiments, the following tests on the collected blood sample can be performed either routinely, or where clinically indicated:

(i) Bacterial culture: To ensure the absence of microbial contamination, established assays can be performed, such as routine hospital cultures for bacteria under aerobic and anaerobic conditions.

(ii) Diagnostic screening for pathogenic microorganisms: To ensure the absence of specific pathogenic microorganisms, various diagnostic tests can be employed. Diagnostic screening for any of the numerous pathogens transmissible through blood can be done by standard procedures. As one example, the collected blood sample (or a maternal blood sample) can be subjected to diagnostic screening for the presence of Human Immunodeficiency Virus-1 or 2 (HIV-1 or HIV-2). Any of numerous assay systems can be used, based on the detection of virions, viral-encoded proteins, HIV-specific nucleic acids, antibodies to HIV proteins, etc. The collected blood can also be tested for other infectious diseases, including but not limited to human T-Cell lymphotropic virus I and II (HTLV-I and HTLV-II), Hepatitis B, Hepatitis C, Cytomegalovirus, Syphilis, West Nile Virus.

Preferably, prior to collection of the cord blood, maternal health history is determined in order to identify risks that the cord blood cells might pose in transmitting genetic or infectious diseases, such as cancer, leukemia, immune disorders, neurological disorders, hepatitis or AIDS. The collected cord blood samples can undergo testing for one or more of cell viability, HLA typing, ABO/Rh typing, $CD34^+$ cell count, and total nucleated cell count.

6.2 Enrichment of Cord Blood Stem Cells

Once the umbilical cord blood and/or placental blood is collected from a single human at birth, the blood is processed to produce an enriched hematopoietic stem cell population, or enriched hematopoietic stem and progenitor cell population, forming a population of CB Stem Cells. The hematopoietic stem cells, or hematopoietic stem and progenitor cells, can be positive for a specific marker expressed in increased levels on the hematopoietic stem cells or hematopoietic stem and progenitor cells, relative to other types of hematopoietic cells. For example, such markers can be, but are not limited to, CD34, CD43, CD45RO, CD45RA, CD59, CD90, CD109, CD117, CD133, CD166, HLA DR, or a combination thereof. The hematopoietic stem cells, or hematopoietic stem and progenitor cells, also can be negative for a specific marker, relative to other types of hematopoietic cells. For example, such markers can be, but are not limited to, Lin, CD38, or a combination thereof. Preferably, the hematopoietic stem cells, or hematopoietic stem and progenitor cells, are $CD34^+$ cells. Preferably, the CB Stem Cell population is enriched in $CD34^+$ stem cells or $CD34^+$ stem and progenitor cells (and, thus, T cell depleted). Enrichment thus refers to a process wherein the percentage of hematopoietic stem cells, or hematopoietic stem and progenitor cells in the sample is increased (relative to the percentage in the sample before the enrichment procedure). Purification is one example of enrichment. In certain embodiments, the increase in the number of $CD34^+$ cells (or other suitable antigen-positive cells) as a percentage of cells in the enriched sample, relative to the sample prior to the enrichment procedure, is at least 25-, 50-, 75-, 100-, 150-, 200-, 250-, 300-, 350-fold, and preferably is 100-200 fold. In a preferred embodiment, the $CD34^+$ cells are enriched using a monoclonal antibody to CD34, which antibody is conjugated to a magnetic bead, and a magnetic cell separation device to separate out the $CD34^+$ cells.

In a preferred embodiment, prior to processing for enrichment, the collected cord and/or placental blood is fresh and has not been previously cryopreserved.

Any technique known in the art for cell separation/selection can be used to carry out the enrichment for hematopoietic stem cells, or hematopoietic stem and progenitor cells. For example, methods which rely on differential expression of cell surface markers can be used. For example, cells expressing the cell surface marker CD34 can be positively selected using a monoclonal antibody to CD34, such that cells expressing CD34 are retained, and cells not expressing CD34 are not retained. Moreover, the separation techniques employed should maximize the viability of the cell to be selected. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., plate, or other convenient technique. Techniques providing accurate separation/selection include fluorescence activated cell sorters, which can have varying degrees of sophistication, e.g., a plurality of color channels, low angle and obtuse light scattering detecting channels, impedance channels, etc.

The antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

In a preferred embodiment of the present invention, a fresh cord blood unit is processed to select for, i.e., enrich for, $CD34^+$ cells using anti-CD34 antibodies directly or indirectly conjugated to magnetic particles in connection with a magnetic cell separator, for example, the CliniMACS® Cell Separation System (Miltenyi Biotec, Bergisch Gladbach, Germany), which employs nano-sized superparamagnetic particles composed of iron oxide and dextran coupled to specific monoclonal antibodies. The CliniMACS® Cell Separator is a closed sterile system, outfitted with a single-use disposable tubing set. The disposable set can be used for and discarded after processing a single unit of collected cord and/or placental blood to enrich for $CD34^+$ cells. Similarly, $CD133^+$ cells can be enriched using anti-CD133 antibodies. In a specific embodiment, $CD34^+CD90^+$ cells are enriched for. Similarly, cells expressing CD43, CD45RO, CD45RA, CD59, CD90, CD109, CD117, CD166, HLA DR, or a combination of the foregoing, can be enriched for using antibodies against the antigen.

In one embodiment, one or more umbilical cord blood and/or placental blood samples can be pooled prior to enriching for the hematopoietic stem cells, or hematopoietic stem and progenitor cells. In another embodiment, individual CB Stem Cell samples can be pooled after enriching for the hematopoietic stem cells, or hematopoietic stem and progenitor cells. In specific embodiments, the number of umbilical cord blood and/or placental blood samples, or CB Stem Cell samples, that are pooled is 2, 3, 4, 5, 6, 7, 8, 9, 10, 15, 20, 25, 30, 35, or 40, or at least any of the foregoing numbers, preferably 20, or no more than 20 or 25, umbilical cord blood and/or placental blood samples, or CB Stem Cell samples, respectively. Preferably, the umbilical cord blood and/or placental blood samples or CB Stem Cell samples are pooled without regard to the HLA type of the hematopoietic stem or hematopoietic stem and progenitor cells. In certain embodiments, the samples in the pool are derived from the umbilical cord blood and/or placental blood of individuals of the same race, e.g., African-American, Caucasian, Asian, Hispanic, Native-American, Australian Aboriginal, Inuit, Pacific Islander, or derived from umbilical cord blood and/or placental blood of individuals of the same ethnicity, e.g., Irish, Italian, Indian, Japanese, Chinese, Russian, etc.

Optionally, prior to enrichment for hematopoietic stem cells or hematopoietic stem and progenitor cells, the red blood cells and white blood cells of the cord blood can be separated. Once the separation of the red blood cells and the white blood cells has taken place, the red blood cell fraction can be discarded, and the white blood cell fraction can be processed in the magnetic cell separator as above. Separation of the white and red blood cell fractions can be performed by any method known in the art, including centrifugation techniques. Other separation methods that can be used include the use of commercially available products FICOLL™ or FICOLL-PAQUE™ or PERCOLL™ (GE Healthcare, Piscataway, New Jersey). FICOLL-PAQUE™ is normally placed at the bottom of a conical tube, and the whole blood is layered above. After being centrifuged, the following layers will be visible in the conical tube, from top to bottom: plasma and other constituents, a layer of mononuclear cells called buffy coat containing the peripheral blood mononuclear cells (white blood cells), FICOLL-PAQUE™ and erythrocytes and granulocytes, which should be present in pellet form. This separation technique allows easy harvest of the peripheral blood mononuclear cells.

Optionally, prior to $CD34^+$ cell selection, an aliquot of the fresh cord blood unit can be checked for total nucleated cell count and/or $CD34^+$ content. In a specific embodiment, after the $CD34^+$ cell selection, both $CD34^+$ ("CB Stem Cells") and $CD34^-$ cell fractions are recovered. Optionally, DNA can be extracted from a sample of the $CD34^-$ cell fraction for initial HLA typing and future chimerism studies, even though HLA matching to the patient is not done according to the methods of the present invention. The $CD34^+$ enriched stem cell fraction ("CB Stem Cells") can be subsequently processed prior to expansion, for example, the Stem Cells can be suspended in an appropriate cell culture medium for transport or storage. In a preferred embodiment, the cell culture medium consists of STEMSPAN™ Serum Free Expansion Medium (StemCell Technologies, Vancouver, British Columbia) supplemented with 10 ng/ml recombinant human Interleukin-3 (rhIL-3), 50 ng/ml recombinant human Interleukin-6 (rhIL-6), 50 ng/ml recombinant human Thrombopoietin (rhTPO), 50 ng/ml recombinant human Flt-3 Ligand (rhFlt-3L), 50 ng/ml and recombinant human stem cell factor (rhSCF).

In a specific embodiment, the umbilical cord blood and/or placental blood sample are red cell depleted, and the number of $CD34^+$ cells in the red cell depleted fraction is calculated. Preferably, the umbilical cord blood and/or placental blood samples containing more than 3.5 million $CD34^+$ cells are enriched by the enrichment methods described above.

6.3 Methods of Cord Blood Stem Cell Expansion

After the CB Stem Cells have been isolated from human cord blood and/or human placental blood collected from one or more humans at birth according to the enrichment methods described above or other methods known in the art, the CB Stem Cells are expanded in order to increase the number of hematopoietic stem cells or hematopoietic stem and progenitor cells, e.g., $CD34^+$ cells. Any method known in the art for expanding the number of CB Stem Cells that gives rise to Expanded CB Stem Cell can be used. Preferably, the CB Stem Cells are cultured under cell growth conditions (e.g., promoting mitosis) such that the CB Stem Cells grow and divide (proliferate) to obtain a population of Expanded CB Stem Cells. In one embodiment, individual populations of CB Stem Cells each derived from the umbilical cord blood and/or placental blood of a single human at birth can be pooled, without regard to the HLA type of the CB Stem Cells, prior to or after the expansion technique. In another embodiment, the sample that is expanded is not a pool of samples. Preferably, the technique used for expansion is one that has been shown to (i) result in an increase in the number of hematopoietic stem cells, or hematopoietic stem and progenitor cells, e.g., $CD34^+$ cells, in the expanded sample relative to the unexpanded CB Stem Cell sample, or (ii) results in an increased number of SCID repopulating cells in the expanded sample determined by limiting-dilution analysis as shown by enhanced engraftment in NOD/SCID mice infused with the expanded sample, relative to that seen with the unexpanded sample, where the unexpanded sample and expanded sample are from different aliquots of the same sample, wherein the expanded sample but not the unexpanded sample is subjected to the expansion technique. In certain embodiments, the technique results in a 50-, 75-, 100-, 150-, 200-, 250-, 300-, 350-, 400-, 450-, or 500-fold increase, preferably a 100-200 fold increase in the number of hematopoietic stem cells or hematopoietic stem and progenitor cells in the expanded sample, relative to the unexpanded CB Stem Cell sample. The hematopoietic stem cells or hematopoietic stem and progenitor cells can be positive for one or more of CD34, CD43, CD45RO, CD45RA, CD59, CD90, CD109, CD117, CD133, CD166, and HLA DR and/or negative for Lin and/or CD38. In a specific embodiment, the enhanced engraftment can be detected by detecting an increased percentage of human $CD45^+$ cells in the bone marrow of mice infused with an aliquot of the expanded sample relative to mice infused with an aliquot of the unexpanded sample at, e.g., 10 days, 3 weeks or 9 weeks post-infusion (see Delaney et al., 2010, Nature Med. 16(2): 232-236).

Such expansion techniques include, but are not limited to those described in U.S. Pat. No. 7,399,633 B2; Delaney et al., 2010, Nature Med. 16(2): 232-236; Zhang et al., 2008, Blood 111:3415-3423; and Himburg et al., 2010, Nature Medicine doi:10.1038/nm.2119 (advanced online publication), as well as those described below.

In one embodiment of the invention, the CB Stem Cells are cultured with growth factors, and are exposed to cell growth conditions (e.g., promoting mitosis) such that the Stem Cells proliferate to obtain an Expanded CB Stem Cell population according to the present invention. In a preferred embodiment of the invention, the CB Stem Cells are cultured with an amount of an agonist of Notch function effective to inhibit differentiation, and are exposed to cell growth conditions (e.g., promoting mitosis) such that the CB Stem Cells proliferate to obtain an Expanded CB Stem Cell population according to the present invention. In a more preferred embodiment, the CB Stem Cells are cultured with an amount of an agonist of Notch function effective to inhibit differentiation and in the presence of growth factors, and are exposed to cell growth conditions (e.g., promoting mitosis) such that the CB Stem Cells proliferate to obtain an Expanded CB Stem Cell population according to the present invention. The Expanded CB Stem Cell population so obtained can be frozen and stored for later use, for example, to provide hematopoietic function to an immunodeficient human patient. Optionally, the Notch pathway agonist is inactivated or removed from the Expanded CB Stem Cell population prior to transplantation into the patient (e.g., by separation, dilution).

In specific embodiments, the CB Stem Cells are cultured for 2, 3, 4, 5, 6, 7, 8, 9, 10, 11, 12, 13, 14, 15, 16, 17, 18, 19, 20, 21, 22, 23, 24, or 25 days or more; or, preferably, the CB Stem Cells are cultured for at least 10 days.

An exemplary culture condition for expanding the CB Stem Cells include is set forth in Section 7.1 infra, and comprises culturing the Stem Cells for 17-21 days in the presence of fibronectin fragments and the extracellular domain of a Delta protein fused to the Fc domain of human IgG ($Delta1^{ext\text{-}IgG}$) in serum free medium supplemented with the following human growth factors: stem cell factor, Flt-3 receptor ligand, thrombopoietin, interleukin-6 and interleukin-3. Preferably, the foregoing growth factors are present at the following concentrations: 50-300 ng/ml stem cell factor, 50-300 ng/ml Flt-3 receptor ligand, 50-100 ng/ml thrombopoietin, 50-100 ng/ml interleukin-6 and 10 ng/ml interleukin-3. In more specific embodiments, 300 ng/ml stem cell factor, 300 ng/ml of Flt-3 receptor ligand, 100 ng/ml thrombopoietin, 100 ng/ml interleukin-6 and 10 ng/ml interleukin-3, or 50 ng/ml stem cell factor, 50 ng/ml of Flt-3 receptor ligand, 50 ng/ml thrombopoietin, 50 ng/ml interleukin-6 and 10 ng/ml interleukin-3 are used. Preferably, the $Delta1^{ext\text{-}IgG}$ is immobilized on the surface of the cell culture dishes. In a specific embodiment, the cell culture dishes are coated overnight at 4° C. (or for a minimum of 2 hours at 37° C.) with 2.5 μg/ml $Delta1^{ext\text{-}IgG}$ and 5 μg/ml RetroNectin® (a recombinant human fibronectin fragment) in phosphate buffered saline, before adding the CB Stem Cells.

Other exemplary culture condition for expanding the CB Stem Cells of the invention comprises are set forth in Zhang et al., 2008, Blood 111:3415-3423. In a specific embodiment, the CB Stem Cells can be cultured in serum free medium supplemented with heparin, stem cell factor, thrombopoietin, insulin-like growth factor-2 (IGF-2), fibroblast growth factor-1 (FGF-1), and Angptl3 or Angptl5. In a specific embodiment, the medium is supplemented with 10 μg/ml heparin, 10 ng/ml stem cell factor, 20 ng/ml thrombopoietin, 20 ng/ml IGF-2, and 10 ng/ml FGF-1, and 100 ng/ml Angptl3 or Angptl5 and the cells are cultured for 19-23 days. In another specific embodiment, the CB Stem Cells can be expanded by culturing the CB Stem Cells in serum free medium supplemented with 10 μg/ml heparin, 10 ng/ml stem cell factor, 20 ng/ml thrombopoietin, 10 ng/ml FGF-1, and 100 ng/ml Angptl5 for 11-19 days. In another specific embodiment, the CB Stem Cells can be expanded by culturing the CB Stem Cells in serum free medium supplemented with 50 ng/ml stem cell factor, 10 ng/ml thrombopoietin, 50 ng/ml Flt-3 receptor ligand, and 100 ng/ml insulin-like growth factor binding protein-2 (IGFBP2) or 500 ng/ml Angptl5 for 10 days. In yet another embodiment, the CB Stem Cells can be expanded by culturing the CB Stem Cells in serum free medium supplemented with 10 μg/ml heparin, 10 ng/ml stem cell factor, 20 ng/ml thrombopoietin, 10 ng/ml FGF-1, 500 ng/ml Angptl5, and 500 ng/ml IGFBP2 for 11 days. See Zhang et al., 2008, Blood 111:3415-3423.

Another exemplary culture condition for expanding the CB Stem Cells of the invention is set forth in Himburg et al., 2010, Nature Medicine doi:10.1038/nm.2119 (advanced online publication). In a specific embodiment, the CB Stem Cells can be cultured in liquid suspension culture supplemented with thrombopoietin, stem cell factor, Flt-3 receptor ligand, and pleiotrophin. In a specific embodiment, the liquid suspension culture is supplemented with 20 ng/ml thrombopoietin, 125 ng/ml stem cell factor, 50 ng/ml Flt-3 receptor ligand, and 10, 100, 500, or 1000 ng/ml pleiotrophin and the CB Stem Cells are cultured for 7 days.

In a preferred embodiment of the invention, after expansion of the CB Stem Cells, the total number of cells and viable $CD34^+$ cells are determined to measure the potency of the sample to provide hematopoietic function. Numerous clinical studies have shown that the total nucleated cell dose and the $CD34^+$ cell dose in stem cell grafts are highly correlated with neutrophil and platelet engraftment as well as the incidence of graft failure and early transplant-related complications (primarily lethal infections) following stem cell transplantation. For example, at day 5-8 post culture initiation during expansion, a sample can be taken for determination of the total viable nucleated cell count. In addition, the total number of $CD34^+$ cells can be determined by multi-parameter flow cytometry, and, thus, the percentage of $CD34^+$ cells in the sample. Preferably, cultures that have not resulted in at least a 10-fold increase in the absolute number of $CD34^+$ cells at this time are discontinued. Similarly, prior to cryopreservation or after thawing, an aliquot of the Expanded CB Stem Cell sample can be taken for determination of total nucleated cells and percentage of viable $CD34^+$ cells in order to calculate the total viable $CD34^+$ cell number in the Expanded CB Stem Cell sample. In a preferred embodiment, those Expanded CB Stem Cell samples containing less than 75 million $CD34^+$ viable cells can be discarded.

In a specific embodiment, total viable $CD34^+$ (or other antigen-positive) cell numbers can be considered the potency assay for release of the final product for therapeutic use. Viability can be determined by any method known in the art, for example, by trypan blue exclusion or 7-AAD exclusion. Preferably, the total nucleated cell count (TNC) and other data are used to calculate the potency of the product. The percentage of viable $CD34^+$ cells can be assessed by flow cytometry and use of a stain that is excluded by viable cells. The percentage of viable $CD34^+$ cells=the number of $CD34^+$ cells that exclude 7-AAD (or other appropriate stain) in an aliquot of the sample divided by the TNC (both viable and non-viable) of the aliquot. Viable $CD34^+$ cells in the sample can be calculated as follows: Viable $CD34^+$ cells=TNC of sample x % viable $CD34^+$ cells in the sample. The proportional increase during enrichment or expansion in viable $CD34^+$ cells can be calculated as follows: Total Viable $CD34^+$ cells Post-culture/Total Viable $CD34^+$ cells Pre-culture. As will be apparent, antigens other than or in addition to CD34 can be used.

6.3.1 Notch Agonists

In a preferred embodiment of the present invention, the CB Stem Cells are expanded by culturing the cells in the presence of an agonist of Notch function and one of more growth factors or cytokines for a given period of time. Culturing the CB Stem Cells can take place under any suitable culture medium/conditions known in the art (see, e.g., Freshney Culture of Animal Cells, Wiley-Liss, Inc., New York, NY (1994)). The time in culture is for a time sufficient to produce an Expanded CB Stem Cell population, as defined herein. For example, the CB Stem Cells can be cultured in a serum-free medium in the presence of an agonist of Notch function and one or more growth factors or cytokines for 2, 3, 4, 5, 6, 7, 8, 9, 10, 11, 12, 13, 14, 15, 16, 17, 18, 19, 20, 21, 22, 23, 24, or 25 days; or, preferably, for at least 10 days. Optionally, at any point during the culturing period, the culture medium can be replaced with fresh medium or fresh medium can be added.

A Notch agonist is an agent that promotes, i.e., causes or increases, activation of Notch pathway function. As used herein, "Notch pathway function" shall mean a function mediated by the Notch signaling (signal transduction) pathway, including but not limited to nuclear translocation of the intracellular domain of Notch, nuclear translocation of RBP-Jκ or its *Drosophila* homolog Suppressor of Hairless; activation of bHLH genes of the Enhancer of Split complex, e.g., Mastermind; activation of the HES-1 gene or the KBF2 (also called CBF1) gene; inhibition of *Drosophila* neuroblast segregation; and binding of Notch to Delta, Jagged/Serrate, Fringe, Deltex or RBP-Jκ/Suppressor of Hairless, or homologs or analogs thereof. See generally the review article by Kopan et al., 2009, Cell 137:216-233 for a discussion of the Notch signal transduction pathway and its effects upon activation; see also Jarriault et al., 1998, Mol. Cell. Biol. 18:7423-7431.

Notch activation is carried out by exposing a cell to a Notch agonist. The agonist of Notch can be but is not limited to a soluble molecule, a molecule that is recombinantly expressed on a cell-surface, a molecule on a cell monolayer to which the precursor cells are exposed, or a molecule immobilized on a solid phase. Exemplary Notch agonists are the extracellular binding ligands Delta and Serrate which bind to the extracellular domain of Notch and activate Notch signal transduction, or a fragment of Delta or Serrate that binds to the extracellular domain of Notch and activates Notch signal transduction. Nucleic acid and amino acid sequences of Delta and Serrate have been isolated from several species, including human, are known in the art, and are disclosed in International Patent Publication Nos. WO 93/12141, WO 96/27610, WO 97/01571, Gray et al., 1999, Am. J. Path. 154:785-794. In a preferred mode of the embodiment, the Notch agonist is an immobilized fragment of a Delta or Serrate protein consisting of the extracellular domain of the protein fused to a myc epitope tag ($Delta^{ext-myc}$ or $Serrate^{ext-myc}$, respectively) or an immobilized fragment of a Delta or Serrate protein consisting of the extracellular domain of the protein fused to the Fc portion of IgG ($Delta^{ext-IgG}$ or $Serrate^{ext-IgG}$, respectively). Notch agonists of the present invention include but are not limited to Notch proteins and analogs and derivatives (including fragments) thereof; proteins that are other elements of the Notch pathway and analogs and derivatives (including fragments) thereof; antibodies thereto and fragments or other derivatives of such antibodies containing the binding region thereof; nucleic acids encoding the proteins and derivatives or analogs; as well as proteins and derivatives and analogs thereof which bind to or otherwise interact with Notch proteins or other proteins in the Notch pathway such that Notch pathway activity is promoted. Such agonists include but are not limited to Notch proteins and derivatives thereof comprising the intracellular domain, Notch nucleic acids encoding the foregoing, and proteins comprising the Notch-interacting domain of Notch ligands (e.g., the extracellular domain of Delta or Serrate). Other agonists include but are not limited to RBPJκ/Suppressor of Hairless or Deltex. Fringe can be used to enhance Notch activity, for example in conjunction with Delta protein. These proteins, fragments and derivatives thereof can be recombinantly expressed and isolated or can be chemically synthesized.

In another specific embodiment, the Notch agonist is a cell which recombinantly expresses a protein or fragment or derivative thereof, which agonizes Notch. The cell expresses the Notch agonist in such a manner that it is made available to the CB Stem Cells in which Notch signal transduction is to be activated, e.g., it is secreted, expressed on the cell surface, etc.

In yet another specific embodiment, the agonist of Notch is a peptidomimetic or peptide analog or organic molecule that binds to a member of the Notch signaling pathway. Such an agonist can be identified by binding assays selected from those known in the art, for example the cell aggregation assays described in Rebay et al., 1991, Cell 67:687-699 and in International Patent Publication No. WO 92/19734.

In a preferred embodiment the agonist is a protein consisting of at least a fragment of a protein encoded by a Notch-interacting gene which mediates binding to a Notch protein or a fragment of Notch, which fragment of Notch contains the region of Notch responsible for binding to the agonist protein, e.g., epidermal growth factor-like repeats 11 and 12 of Notch. Notch interacting genes, as used herein, shall mean the genes Notch, Delta, Serrate, RBPJκ, Suppressor of Hairless and Deltex, as well as other members of the Delta/Serrate family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in *Drosophila*). Exemplary fragments of Notch-binding proteins containing the region responsible for binding to Notch are described in U.S. Pat. Nos. 5,648,464; 5,849,869; and 5,856,441.

The Notch agonists utilized by the methods of the invention can be obtained commercially, produced by recombinant expression, or chemically synthesized.

In a specific embodiment, exposure of the cells to a Notch agonist is not done by incubation with other cells recombinantly expressing a Notch ligand on the cell surface (although in other embodiments, this method can be used), but rather is by exposure to a cell-free Notch ligand, e.g., incubation with a cell-free ligand of Notch, which ligand is immobilized on the surface of a solid phase, e.g., immobilized on the surface of a tissue culture dish.

In specific embodiments, Notch activity is promoted by the binding of Notch ligands (e.g., Delta, Serrate) to the extracellular portion of the Notch receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate molecules, comprising the extracellular domains of the proteins or Notch-binding portions thereof, that have been immobilized on a solid surface, such as a tissue culture plate, are particularly preferred Notch pathway agonists. Such soluble proteins can be immobilized on a solid surface by an antibody or interacting protein, for example an antibody directed to an epitope tag with which Delta or Serrate is expressed as a fusion protein (e.g., a myc epitope tag, which is recognized by the antibody 9E10) or a protein which interacts with an epitope tag with which Delta or Serrate is expressed as a fusion protein (e.g., an immunoglobulin epitope tag, which is bound by Protein A).

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins.

U.S. Pat. No. 5,780,300 further discloses classes of Notch agonist molecules (and methods of their identification) which can be used to activate the Notch pathway in the practice of the present invention, for example molecules that trigger the dissociation of the Notch ankyrin repeats with RBP-Jκ, thereby promoting the translocation of RBP-Jκ from the cytoplasm to the nucleus.

6.3.2 Growth Factors/Cytokines

In a preferred embodiment of the present invention, the CB Stem Cells are expanded by culturing the cells in the presence of an agonist of Notch function, discussed supra, and one of more growth factors or cytokines for a given period of time. Alternatively, the CB Stem Cells are expanded by culturing the cells in the presence of one of more growth factors or cytokines for a given period of time. Wherein expansion of the CB Stem Cells without differentiation is to be achieved, the CB Stem Cells of the invention are cultured in the presence of growth factors that support growth but not differentiation. The growth factor can be any type of molecule, such as a protein or a chemical compound, that promotes cellular proliferation and/or survival.

Exposing the CB Stem Cells to one or more growth factors can be done prior to, concurrently with, or following exposure of the cells to a Notch agonist.

In specific exemplary embodiments, the growth factors present in the expansion medium include one or more of the following growth factors: stem cell factor (SCF), also known as the c-kit ligand or mast cell growth factor, Flt-3 ligand (Flt-3L), interleukin-6 (IL-6), interleukin-3 (IL-3), interleukin-11 (IL-11) and thrombopoietin (TPO), granulocyte-macrophage colony stimulating factor (GM-CSF), granulocyte colony stimulating factor (G-CSF), angiopoietin-like proteins (Angptls) (Angptl2, Angptl3, Angptl5, Angptl7, and Mfap4), insulin growth factor-2 (IFG-2), fibroblast growth factor-1 (FGF-1). The amount of SCF, Flt-3L, IL-6, or TPO can be in the range of 10-1000 ng/ml, more preferably about 50-500 ng/ml, most preferably about 100-300 ng/ml. In certain specific embodiments, the amount of SCF, Flt-3L, IL-6, or TPO is 100, 125, 150, 175, 200, 225, 250, 275, 300, 325, 350, 375, 400, 425 or 450 ng/ml. The amount of 11-3, IL-11, G-CSF, or GM-CSF can be in the range of 2-100 ng/ml, more preferably about 5-50 ng/ml, more preferably about 7.5-25 ng/ml, most preferably about 10-15 ng/ml. In certain specific embodiments, the amount of IL-3, IL-11, G-CSF, or GM-CSF is 5, 6, 7, 8, 9, 10, 12.5, or 15 ng/ml.

In a preferred embodiment for expanding CB Stem Cells, the cells are cultured in a tissue culture dish onto which an extracellular matrix protein is bound. In a preferred mode of the embodiment, the extracellular matrix protein is fibronectin (FN), or a fragment thereof. Such a fragment can be but is not limited to CH-296 (Dao et al., 1998, Blood 92(12): 4612-21) or RetroNectin® (a recombinant human fibronectin fragment) (Clontech Laboratories, Inc., Madison, WI).

In a specific embodiment for expanding CB Stem Cells of the present invention, the cells are cultured on a plastic tissue culture dish containing immobilized Delta ligand, e.g., the extracellular domain of Delta, and fibronectin in the presence of 100 ng/ml of each of SCF and TPO, and 10 ng/ml GM-CSF. In another specific embodiment for expanding CB Stem Cells, the cells are cultured on a plastic tissue culture dish containing immobilized Delta ligand and fibronectin in the presence of 100 ng/ml of each of SCF, Flt-3L, TPO and IL-6 and 10 ng/ml of IL-3. In another specific embodiment for expanding Stem Cells of the present invention, the cells are cultured on a plastic tissue culture dish containing immobilized Delta ligand and fibronectin in the presence of 100 ng/ml of each of SCF and Flt-3L and 10 mg/ml of each of G-CSF and GM-CSF. In another specific embodiment for expanding CB Stem Cells, the cells are cultured on a plastic tissue culture dish containing immobilized Delta ligand and fibronectin in the presence of 100 ng/ml of each of SCF, Flt-3L and TPO and 10 mg/ml of GM-CSF. In yet another specific embodiment for expanding CB Stem Cells, the cells are cultured on a plastic tissue culture dish containing immobilized Delta ligand and fibronectin in the presence of 300 ng/ml of each of SCF and Flt-3L, 100 ng/ml of each of TPO and IL-6, and 10 mg/ml of IL-3. In another embodiment for expanding CB Stem Cells, the cells are cultured on a plastic tissue culture dish containing immobilized Delta ligand and fibronectin in the presence of 100 ng/ml of each of SCF, Flt-3L, and TPO and 10 mg/ml of each of G-CSF and GM-CSF. In alternative embodiments to the foregoing culture conditions, fibronectin is excluded from the tissue culture dishes or is replaced by another extracellular matrix protein. See also U.S. Pat. No. 7,399,633 B2 to Bernstein et al. for additional exemplary culture conditions for CB Stem Cell expansion.

The growth factors utilized by the methods of the invention can be obtained commercially, produced by recombinant expression, or chemically synthesized. For example, Flt-3L (human), IGF-1 (human), IL-6 (human and mouse), IL-11 (human), SCF (human), TPO (human and murine) can be purchased from Sigma (St. Louis, Mo.). IL-6 (human and murine), IL-7 (human and murine), and SCF (human) can be purchased from Life Technologies, Inc. (Rockville, Md.).

In other embodiments, the growth factors are produced by recombinant expression or by chemical peptide synthesis (e.g. by a peptide synthesizer). Growth factor nucleic acid and peptide sequences are generally available from GenBank.

Preferably, but not necessarily, the growth factor(s) used to expand the CB Stem Cells in the presence of a Notch agonist by the methods of the invention is derived from the same species as the CB Stem Cells.

The amount or concentration of growth factors suitable for expanding the CB Stem Cells of the present invention will depend on the activity of the growth factor preparation, and the species correspondence between the growth factors and the CB Stem Cells, etc. Generally, when the growth factor(s) and the CB Stem Cells are of the same species, the total amount of growth factor in the culture medium ranges from 1 ng/ml to 5 μg/ml, more preferably from 5 ng/ml to 1 μg/ml, and most preferably from about 10 ng/ml to 200 ng/ml. In one embodiment, the CB Stem Cells are expanded by exposing the CB Stem Cells to a Notch agonist and 100 ng/ml of SCF. In another embodiment, the CB Stem Cells are expanded by exposing the CB Stem Cells to a Notch agonist and 100 ng/ml of each of Flt-3L, IL-6 and SCF and 10 ng/ml of IL-11.

6.4 Cryopreservation and Thawing 6.4.1 Cryopreservation

Once the Expanded CB Stem Cell population is obtained after expanding CB Stem Cells from cord blood, the Expanded CB Stem Cell population can be cryopreserved. In one embodiment, an Expanded CB Stem Cell population can be divided and frozen in one or more bags (or units). In another embodiment, two or more Expanded CB Stem Cell populations can be pooled, divided into separate aliquots, and each aliquot is frozen. In a preferred embodiment, a maximum of approximately 4 billion nucleated cells is frozen in a single bag. In a preferred embodiment, the Expanded CB Stem Cells are fresh, i.e., they have not been previously frozen prior to expansion or cryopreservation. The terms "frozen/freezing" and "cryopreserved/cryopreserving" are used interchangeably in the present application. Cryopreservation can be by any method in known in the art that freezes cells in viable form. The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroy the cell. For a discussion, see Mazur, P., 1977, Cryobiology 14:251-272.

These injurious effects can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO. After addition of DMSO, cells should be kept at 0° C. until freezing, since DMSO concentrations of about 1% are toxic at temperatures above 4° C.

A controlled slow cooling rate can be critical. Different cryoprotective agents (Rapatz et al., 1968, Cryobiology 5(1):18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1):17-32; and Mazur, 1970, Science 168:939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1° to 3° C./minute from 0° C. to −80° C. In a preferred embodiment, this cooling rate can be used for the neonatal cells of the invention. The container holding the cells must be stable at cryogenic temperatures and allow for rapid heat transfer for effective control of both freezing and thawing. Sealed plastic vials (e.g., Nunc, Wheaton cryules) or glass ampules can be used for multiple small amounts (1-2 ml), while larger volumes (100-200 ml) can be frozen in polyolefin bags (e.g., Delmed) held between metal plates for better heat transfer during cooling. Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred embodiment, DMSO-treated cells are precooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1° to 3° C./minute. After at least two hours, the specimens have reached a temperature of −80° C. and can be placed directly into liquid nitrogen (−196° C.) for permanent storage.

After thorough freezing, the Expanded CB Stem Cells can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Suitable racking systems are commercially available and can be used for cataloguing, storage, and retrieval of individual specimens.

Considerations and procedures for the manipulation, cryopreservation, and long-term storage of the hematopoietic stem cells, particularly from bone marrow or peripheral blood, are largely applicable to the Expanded CB Stem Cells of the invention. Such a discussion can be found, for example, in the following references, incorporated by reference herein: Gorin, 1986, Clinics In Haematology 15(1): 19-48; Bone-Marrow Conservation, Culture and Transplantation, Proceedings of a Panel, Moscow, Jul. 22-26, 1968, International Atomic Energy Agency, Vienna, pp. 107-186.

Other methods of cryopreservation of viable cells, or modifications thereof, are available and envisioned for use (e.g., cold metal-mirror techniques; Livesey and Linner, 1987, Nature 327:255; Linner et al., 1986, J. Histochem. Cytochem. 34(9):1123-1135; see also U.S. Pat. No. 4,199,022 by Senkan et al., U.S. Pat. No. 3,753,357 by Schwartz, U.S. Pat. No. 4,559,298 by Fahy).

6.4.2 Thawing

Frozen cells are preferably thawed quickly (e.g., in a water bath maintained at 37°-41° C.) and chilled immediately upon thawing. In a specific embodiment, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In an embodiment of the invention, the Expanded CB Stem Cell sample as thawed, or a portion thereof, can be infused for providing hematopoietic function in a human patient in need thereof. Several procedures, relating to processing of the thawed cells are available, and can be employed if deemed desirable.

It may be desirable to treat the cells in order to prevent cellular clumping upon thawing. To prevent clumping, various procedures can be used, including but not limited to, the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc.

The cryoprotective agent, if toxic in humans, should be removed prior to therapeutic use of the thawed Expanded CB Stem Cells. In an embodiment employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, 1977, Biochemical Methods in Cell Culture and Virology, Dowden, Hutchinson & Ross, Stroudsburg, Pa., pp. 18-19; 1964, Methods in Medical Research, Eisen et al., eds., Vol. 10, Year Book Medical Publishers, Inc., Chicago, pp. 39-47) can be done to confirm cell survival. The percentage of viable antigen (e.g., CD34) positive cells in a sample can be determined by calculating the number of antigen positive cells that exclude 7-AAD (or other suitable dye excluded by viable cells) in an aliquot of the sample, divided by the total number of nucleated cells (TNC) (both viable and non-viable) in the aliquot of the sample. The number of viable antigen positive cells in the sample can be then determined by multiplying the percentage of viable antigen positive cells by TNC of the sample.

Prior to cryopreservation and/or after thawing, the total number of nucleated cells, or in a specific embodiment, the total number of CD34+ or CD133+ cells can be determined. For example, total nucleated cell count can be performed by using a hemocytometer and exclusion of trypan blue dye. Specimens that are of high cellularity can be diluted to a concentration range appropriate for manual counting. Final cell counts for products are corrected for any dilution factors. Total nucleated cell count=viable nucleated cells per mL×volume of product in mL. The number of CD34+ or CD133+ positive cells in the sample can be determined, e.g., by the use of flow cytometry using anti-CD34 or anti-CD133 monoclonal antibodies conjugated to a fluorochrome.

Optionally, the Expanded CB Stem Cell sample can undergo HLA typing either prior to cryopreservation and/or after cryopreservation and thawing. HLA typing can be performed using serological methods with antibodies specific for identified HLA antigens, or using DNA-based methods for detecting polymorphisms in the HLA antigen-encoding genes for typing HLA alleles. In a specific embodiment, HLA typing can be performed at intermediate resolution using a sequence specific oligonucleotide probe method for HLA-A and HLA-B or at high resolution using a sequence based typing method (allele typing) for HLA-DRB1.

In certain embodiments, the identity and purity of the starting umbilical cord blood and/or placental blood, the CB Stem Cells, and the Expanded CB Stem Cells prior to cryopreservation, or the Expanded CB Stem Cells after thawing can be subjected to multi-parameter flow cytometric immunophenotyping, which provides the percentage of viable antigen positive cells present in a sample. Each sample can be tested for one or more of the following cell phenotypes using a panel of monoclonal antibodies directly conjugated to fluorochromes:

1. $CD34^+$ HPC
2. T cells ($CD3^+$, including both $CD4^+$ and $CD8^+$ subsets)
3. B cells ($CD19^+$ or $CD20^+$)
4. NK cells ($CD56^+$)
5. Monocytes ($CD14^+$)
6. Myelomonocytes ($CD15^+$)
7. Megakaryocytes ($CD41^+$)
8. Dendritic Cells (lineage negative/HLA-DRbright and CD123bright, or lineage negative/HLA-DRbright and CD11cbright).

6.5 Genetically Engineered Stem Cells

In a preferred embodiment, the Expanded CB Stem Cells administered to the patient are non-recombinant. However, in a different embodiment, the CB Stem Cells prior to expansion or the Expanded CB Stem Cells can be genetically engineered to produce gene products beneficial upon transplantation of the genetically engineered cells to a subject. Such gene products include but are not limited to anti-inflammatory factors, e.g., anti-TNF, anti-IL-1, anti-IL-2, etc. The CB Stem Cells can be genetically engineered for use in gene therapy to adjust the level of gene activity in a subject to assist or improve the results of transplantation or to treat a disease caused by, for example, a deficiency in the recombinant gene. The CB Stem Cells are made recombinant by the introduction of a recombinant nucleic acid into the CB Stem Cells or into the Expanded CB Stem Cells.

In its broadest sense, gene therapy refers to therapy performed by the administration of a nucleic acid to a subject. The nucleic acid, either directly or indirectly via its encoded protein, mediates a therapeutic effect in the subject. The present invention provides methods of gene therapy wherein a nucleic acid encoding a protein of therapeutic value (preferably to humans) is introduced into the CB Stem Cells, before or after expansion, such that the nucleic acid is expressible by the Stem Cells and/or their progeny, followed by administration of the recombinant Expanded CB Stem Cells to a subject.

The recombinant CB Stem Cells of the present invention can be used in any of the methods for gene therapy available in the art. Thus, the nucleic acid introduced into the cells may encode any desired protein, e.g., a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Gardlik et al., 2005, Med. Sci. Monit. 11:RA110-121; Lundstrom, 1999, J. Recept. Signal Transduct. Res. 19:673-686; Robbins and Ghivizzani, 1998, Pharmacol. Ther. 80:35-47; Pelegrin et al., 1998, Hum. Gene Ther. 9:2165-2175; Harvey and Caskey, 1998, Curr. Opin. Chem. Biol. 2:512-518; Guntaka and Swamynathan, 1998, Indian J. Exp. Biol. 36:539-535; Desnick and Schuchman, 1998, Acta Paediatr. Jpn. 40:191-203; Vos, 1998, Curr. Opin. Genet. Dev. 8:351-359; Tarahovsky and Ivanitsky, 1998, Biochemistry (Mosc) 63:607-618; Morishita et al., 1998, Circ. Res. 2:1023-1028; Vile et al., 1998, Mol. Med. Today 4:84-92; Branch and Klotman, 1998, Exp. Nephrol. 6:78-83; Ascenzioni et al., 1997, Cancer Lett. 118:135-142; Chan and Glazer, 1997, J. Mol. Med. 75:267-282. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant CB Stem Cells are used in gene therapy, a gene whose expression is desired in a subject is introduced into the CB Stem Cells such that it is expressible by the cells and/or their progeny, and the recombinant cells are then administered in vivo for therapeutic effect.

Recombinant Expanded CB Stem Cells can be used in any appropriate method of gene therapy, as would be recognized by those in the art upon considering this disclosure. The resulting action of recombinant cell populations administered to a subject can, for example, lead to the activation or inhibition of a pre-selected gene in the subject, thus leading to improvement of the diseased condition afflicting the subject.

In this embodiment, the desired gene is introduced into the CB Stem Cell or its progeny prior to administration in vivo of the resulting recombinant cell. Such introduction can be carried out by any method known in the art, including but not limited to transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject.

More detail about retroviral vectors can be found in Boesen et al., 1994, Biotherapy 6:291-302, Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are also of use in gene therapy. See Kozarsky and Wilson, 1993, Current Opinion in Genetics and Development 3:499-503, Rosenfeld et al., 1991, Science 252:431-434; Rosenfeld et al., 1992, Cell 68:143-155; and Mastrangeli et al., 1993, J. Clin. Invest. 91:225-234.

It has been proposed that adeno-associated virus (AAV) be used in gene therapy (Walsh et al., 1993, Proc. Soc. Exp. Biol. Med. 204:289-300). It has also been proposed that alphaviruses be used in gene therapy (Lundstrom, 1999, J. Recept. Signal Transduct. Res. 19:673-686).

Other methods of gene delivery in gene therapy include the use of mammalian artificial chromosomes (Vos, 1998, Curr. Op. Genet. Dev. 8:351-359); liposomes (Tarahovsky and Ivanitsky, 1998, Biochemistry (Mosc) 63:607-618);

ribozymes (Branch and Klotman, 1998, Exp. Nephrol. 6:78-83); and triplex DNA (Chan and Glazer, 1997, J. Mol. Med. 75:267-282).

A desired gene can be introduced intracellularly and incorporated within CB Stem Cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, the desired gene recombinantly expressed in the CB Stem Cells or their progeny after expansion to be introduced for purposes of gene therapy comprises an inducible promoter operably linked to the coding region, such that expression of the recombinant gene is controllable by controlling the presence or absence of the appropriate inducer of transcription.

6.6 Selection of Expanded Cord Blood Cells

In accordance with the present invention, an Expanded CB Stem Cell sample is selected for administration to a human patient in need thereof in order to provide hematopoietic function to the patient, which selection is without regard to matching the HLA type of the sample to the HLA type of the patient, i.e., the selection does not take into account the HLA type of the sample or the HLA type of the patient. Thus, the Expanded CB Stem Cell sample may have the same HLA type as the patient or the HLA type of the Expanded CB Stem Cell sample may differ from the HLA type of the patient at 1, 2, 3, 4, 5, 6 or more of the typed HLA antigens and/or alleles. In another embodiment, the HLA type of the Expanded CB Stem Cell sample may differ from the HLA type of the patient at all of the HLA antigens and/or alleles typed.

In one embodiment of the invention, a method for providing hematopoietic function to a human patient in need thereof is provided, which method comprises (a) selecting an expanded human cord blood stem cell sample for administration to the patient, wherein said selecting does not take into account the HLA-type of the sample or the HLA-type of the patient; and (b) administering the selected sample to the patient. In a preferred embodiment, the selecting is from a plurality of different samples (e.g., at least 100, 200, 250, 500, 750, 1000, 1500, 2,000, 3,000, 5,000, 7,500, 10,000, 25,000, 50,000 or 100,000 different expanded cord blood stem cell samples), preferably stored frozen in a bank. In a specific embodiment, at least the foregoing numbers of samples in the plurality are not pooled samples. In a specific embodiment, the plurality of samples does not contain pooled samples. In a different specific embodiment, the plurality of different samples comprises at least 5, 10, 20, 25, 50, 75, 100, 500, or 1000 pooled samples.

Optional parameters for consideration in the selection of an Expanded CB Stem Cell sample for use in a method of treatment according to the present invention include, but are not limited to one or more of total nucleated cell count, total $CD34^+$ (or other suitable antigen) cell count, age of sample, age of patient, race or ethnic background of donor, weight of the patient, type of disease to be treated and its level of severity in a particular patient, presence of $CD3^+$ cells in the Expanded CB Stem Cell sample, panel reactive antibody result of the patient, etc. For example, in a specific embodiment, an Expanded CB Stem Cell sample can be rejected, and thus not selected for use in a method of treatment if there are more than 500,000 $CD3^+$ cells per kilogram (patient weight) in the sample.

In a specific embodiment, the selecting can be computer-implemented, whereby the selection software can take into account any one or more of the foregoing information characterizing the sample, e.g., by filtering out (rejecting) samples that do not meet certain criteria, e.g., that do not contain threshold amounts of $CD34^+$ cells (e.g., at least 75 million $CD34^+$ cells, preferably, at least 100 million, 150 million, 200 million, 250 million, 300 million, 350 million, most preferably at least 250 million), and/or that contain more than a threshold amount of $CD3^+$ cells (e.g., more than 500,000 $CD3^+$ per kilogram patient weight). In a specific embodiment, samples left after filtering are selected, for example, by choosing the sample stored for the longest period, or at random, or based on any characteristic useful to the skilled practitioner.

The selection of the sample can be carried out by a suitably programmed computer by selecting an appropriate identifier for the frozen, Expanded CB Stem Cell sample, from among a plurality of identifiers stored in a computer database, each identifying a different frozen, Expanded CB Stem Cell sample. Each identifier is preferably associated with the information for its corresponding sample as described above (one or more of total nucleated cell count, total $CD34^+$ cell count, etc.), so that the software can take into account the information as described above in the selection process.

6.7 Therapeutic Methods

The Expanded CB Stem Cell populations, whether recombinantly expressing a desired gene or not, can be administered into a human patient in need thereof for hematopoietic function for the treatment of disease or injury or for gene therapy by any method known in the art which is appropriate for the Expanded CB Stem Cells and the transplant site. Preferably, the Expanded CB Stem Cells are transplanted (infused) intravenously. In one embodiment, the Expanded CB Stem Cells differentiate into cells of the myeloid lineage in the patient. In another embodiment, the Expanded CB Stem Cells differentiate into cells of the lymphoid lineage in the patient. Administration of the Expanded CB Stem Cells is without regard to whether the patient matches or mismatches the Expanded CB Stem Cells at HLA antigens and/or alleles. HLA-mismatched cells do not match at one or two or more of the human HLA antigens and/or alleles that are typed. In one embodiment, at least one HLA antigen or allele is found to be different between the expanded human cord blood stem cell sample and the recipient patient among those HLA antigens or alleles typed. The present invention provides a method for providing hematopoietic function to a human patient in need thereof by administering an expanded human cord blood stem cell sample to the patient, wherein said administering is done without matching the HLA-type of the expanded human cord blood stem cell sample to the patient.

In specific embodiments, the Expanded CB Stem Cells are not administered to the patient within 12 hours of administration of a myeloid progenitor cell population as defined in International Patent Publication Nos. WO 2006/047569 A2 and/or WO 2007/095594 A2. In other specific embodiments, the Expanded CB Stem Cells are not administered to the patient within 18 or 24 or 36 or 48 or 72 or 96 hours or within 7, 10, 14, 21, 30 days of administration of such a myeloid progenitor cell population to the patient.

In a specific embodiment, the Expanded CB Stem Cell sample that is administered to the patient is not a pooled sample, i.e., it is derived from the umbilical cord blood and/or placental blood of one individual.

In a specific embodiment, the methods of the invention described herein, involving administration of Expanded CB Stem Cell samples, further comprise administering one or more umbilical cord blood/placental blood samples (hereinafter called "Grafts" or "cord blood transplants"). Such Grafts are umbilical cord blood and/or placental blood samples from humans that are whole blood samples, except that red blood cells have been removed from the whole blood samples, but which samples have not been further fractionated and have not been expanded. In a specific embodiment, the Grafts have been cryopreserved and are thawed prior to administration. In a specific embodiment, at least 4 of the HLA antigens or alleles of the Grafts are typed. In a preferred embodiment, 6 HLA antigens or alleles (e.g., each of the 2 HLA-A, HLA-B and HLA-DR alleles) are typed. In a preferred embodiment, the one or more Grafts administered to the patient match the patient at at least 4 out of 6 HLA antigens or alleles. In contrast to embodiments where the Graft is selected to match or partially match the patient at typed HLA antigens or alleles, the Expanded CB Stem Cell sample is administered without matching the HLA-type of the Expanded CB Stem Cell sample to the HLA-type of the patient. In a specific embodiment, the Graft is also administered without matching the HLA-type of the Graft with the HLA-type of the patient. The Grafts can be administered concurrently with, sequentially with respect to, before, or after the Expanded CB Stem Cell sample is administered to the patient. In a specific embodiment, the Expanded CB Stem Cell sample that is administered to the patient is administered within 1, 2, 3, 4, 5, 6, 7, 8, 9 or 10 days of administering the one or more Grafts. In a specific embodiment, the Expanded CB Stem Cell sample is administered before administering the one or more Grafts. In another specific embodiment, the Expanded CB Stem Cell sample is administered after administering the one or more Grafts. In a specific embodiment, the Expanded CB Stem Cell sample is administered 1 to 24 hours, 2 to 12 hours, 3 to 8 hours, or 3 to 5 hours before or after administering the one or more Grafts. In other specific embodiments, the Expanded CB Stem Cell sample is administered about 1, 2, 3, 4, 5, 6, 7, 8, 9, 10, 11, 12, 18, or 24 hours before or after administering the one or more Grafts. In a preferred embodiment, the Expanded CB Stem Cell sample is administered about 4 hours after administering the one or more Grafts. In a specific embodiment, a single Graft is administered that is derived from the cord and/or placental blood of a single human individual. In a specific embodiment, two Grafts are administered, each derived from the cord and/or placental blood of a different human individual. In another specific embodiment, a single Graft is administered that is a combination of cord and/or placental blood derived from two or more different human individuals. In the foregoing embodiments, the Expanded CB Stem Cell sample is intended to provide temporary hematopoietic benefit to the patient, while the Graft is intended to provide long-term engraftment.

Other suitable methods of administration of the Expanded CB Stem Cells are encompassed by the present invention. The Expanded CB Stem Cell populations can be administered by any convenient route, for example by infusion or bolus injection, and may be administered together with other biologically active agents. Administration can be systemic or local.

The titer of Expanded CB Stem Cells administered which will be effective in the treatment of a particular disorder or condition will depend on the nature of the disorder or condition, and can be determined by standard clinical techniques. In addition, in vitro and in vivo assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. In specific embodiments, suitable dosages of Expanded CB Stem Cells for administration are generally about at least $5\times10^6$, $10^7$, $5\times10^7$, $75\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ $CD34^+$ cells per kilogram patient weight, and most preferably about $10^7$ to about $10^{12}$ $CD34^+$ cells per kilogram patient weight, and can be administered to a patient once, twice, three or more times with intervals as often as needed. In a specific embodiment, a single Expanded Stem Cell sample provides one or more doses for a single patient. In one specific embodiment, a single Expanded Stem Cell sample provides four doses for a single patient.

The patient is a human patient, preferably an immunodeficient human patient.

In a specific embodiment, the Expanded CB Stem Cell population administered to a human patient in need thereof can be a pool of at least two individual Expanded CB Stem Cell samples, each sample derived from the umbilical cord blood and/or placental blood of a single human. For example, an aliquot of a frozen, thawed, expanded sample that is a pool of samples (i.e., a pooled sample) can be administered. In one embodiment, the individual Expanded CB Stem Cell samples in the pool can have different HLA types. For example, where the mixture contains three individual samples, each sample can differ from the others by at least one or more of the typed HLA antigens or alleles, e.g., by at least one of the commonly typed HLA antigens or alleles. In one embodiment, the individual samples in the pool are all derived from umbilical cord blood and/or placental blood of individuals of the same race, e.g., African-American, Caucasian, Asian, Hispanic, Native-American, Australian Aboriginal, Inuit, Pacific Islander, or are all derived from umbilical cord blood and/or placental blood of individuals of the same ethnicity, e.g., Irish, Italian, Indian, Japanese, Chinese, Russian, etc. In an alternative embodiment, the administered sample is not a pool of samples.

6.8 Pharmaceutical Compositions

The invention provides methods of treatment by administration to a patient of a pharmaceutical (therapeutic) composition comprising a therapeutically effective amount of recombinant or non-recombinant Expanded CB Stem Cells produced by the methods of the present invention as described herein above, wherein administration is done without matching the HLA-type of the Expanded CB Stem Cells to the patient. Preferably, a myeloid progenitor cell population is not administered to the patient within 12 hours of the administering of the expanded human cord blood stem cell sample, wherein a majority of the cells in the myeloid progenitor cell population do not produce lymphoid cells in cell culture. In other embodiments, a myeloid progenitor cell population is not administered to the patient within 18, 20, 24, 36, 48, 72 hours or within 1 week of the administering of the expanded human cord blood stem cell sample, wherein a majority of the cells in the myeloid progenitor cell population do not produce lymphoid cells in cell culture. In a specific embodiment, a majority of the cells in the myeloid cell population express the cell surface marker CD33 and/or do not express the cell surface marker CD45RA.

The present invention provides pharmaceutical compositions. Such compositions comprise a therapeutically effective amount of Expanded CB Stem Cells, and a pharmaceutically acceptable carrier or excipient. Such a carrier can be but is not limited to saline, buffered saline, dextrose, water, glycerol, ethanol, and combinations thereof. The carrier and composition preferably are sterile. The formulation should suit the mode of administration. The pharmaceutical composition is acceptable for therapeutic use in humans. The composition, if desired, can also contain pH buffering agents.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

The invention also provides a pharmaceutical pack or kit comprising one or more containers filled with one or more of the Stem Cell or Expanded CB Stem Cell populations produced by the methods of the invention and/or reagents to prepare said cells, or with reagents for the genetic manipulation of the cells.

In a preferred embodiment, a kit of the invention comprises in one or more containers one or more purified growth factors that promote proliferation but not differentiation of a precursor cell and a purified Notch agonist, which growth factors and Notch agonist are together effective to expand Stem Cells exposed to them in culture. Optionally, cell culture medium is also provided.

Optionally associated with such container(s) can be a notice in the form prescribed by a governmental agency regulating the manufacture, use or sale of pharmaceuticals or biological products, which notice reflects approval by the agency of manufacture, use or sale for human administration.

6.9 Therapeutic Uses of the Expanded CB Stem Cells

The Expanded CB Stem Cells of the present invention can be used to provide hematopoietic function to a patient in need thereof, preferably a human patient, without matching the HLA-type of the expanded human cord blood stem cell sample to the patient. The Expanded CB Stem Cells that are administered to a patient in need thereof can be derived from the umbilical cord blood and/or placental blood of a single human at birth, or can be derived from the umbilical cord blood and/or placental blood of more than 1 human at birth (pool of samples), as described above. In one embodiment, administration of Expanded CB Stem Cells of the invention is for the treatment of immunodeficiency. In a preferred embodiment, administration of Expanded CB Stem Cells of the invention is for the treatment of pancytopenia or for the treatment of neutropenia. The immunodeficiency in the patient, for example, pancytopenia or neutropenia, can be the result of an intensive chemotherapy regimen, myeloablative regimen for hematopoietic cell transplantation (HCT), or exposure to acute ionizing radiation. Exemplary chemotherapeutics that can cause prolonged pancytopenia or prolonged neutropenia include, but are not limited to alkylating agents such as cisplatin, carboplatin, and oxaliplatin, mechlorethamine, cyclophosphamide, chlorambucil, and ifosfamide. Other chemotherapeutic agents that can cause prolonged pancytopenia or prolonged neutropenia include azathioprine, mercaptopurine, vinca alkaloids, e.g., vincristine, vinblastine, vinorelbine, vindesine, and taxanes. In particular, a chemotherapy regimen that can cause prolonged pancytopenia or prolonged neutropenia is the administration of clofarabine and Ara-C.

In one embodiment, the patient is in an acquired or induced aplastic state.

The immunodeficiency in the patient also can be caused by exposure to acute ionizing radiation following a nuclear attack, e.g., detonation of a "dirty" bomb in a densely populated area, or by exposure to ionizing radiation due to radiation leakage at a nuclear power plant, or exposure to a source of ionizing radiation, raw uranium ore.

Transplantation of Expanded CB Stem Cells of the invention can be used in the treatment or prevention of hematopoietic disorders and diseases. In one embodiment, the Expanded CB Stem Cells are used to treat or prevent a hematopoietic disorder or disease characterized by a failure or dysfunction of normal blood cell production and cell maturation. In another embodiment, the Expanded CB Stem Cells are used to treat or prevent a hematopoietic disorder or disease resulting from a hematopoietic malignancy. In yet another embodiment, the Expanded CB Stem Cells are used to treat or prevent a hematopoietic disorder or disease resulting from immunosuppression, particularly immunosuppression in subjects with malignant, solid tumors. In yet another embodiment, the Expanded CB Stem Cells are used to treat or prevent an autoimmune disease affecting the hematopoietic system. In yet another embodiment, the Expanded CB Stem Cells are used to treat or prevent a genetic or congenital hematopoietic disorder or disease.

Examples of particular hematopoietic diseases and disorders which can be treated by the Expanded CB Stem Cells of the invention include but are not limited to those listed in Table I, infra.

TABLE I

| DISEASES OR DISORDERS WHICH CAN BE TREATED BY ADMINISTERING EXPANDED CB STEM CELLS OF THE INVENTION |
|---|
| I. Diseases Resulting from a Failure or Dysfunction of Normal Blood Cell Production and Maturation |
| hyperproliferative stem cell disorders |
| aplastic anemia |
| pancytopenia |
| agranulocytosis |
| thrombocytopenia |
| red cell aplasia |
| Blackfan-Diamond syndrome due to drugs, radiation, or infection |
| Idiopathic |
| II. Hematopoietic malignancies |
| acute lymphoblastic (lymphocytic) leukemia |
| chronic lymphocytic leukemia |
| acute myelogenous leukemia |
| chronic myelogenous leukemia |
| acute malignant myelosclerosis |
| multiple myeloma |
| polycythemia vera |
| agnogenic myelometaplasia |
| Waldenstrom's macroglobulinemia |
| Hodgkin's lymphoma |
| non-Hodgkin's lymphoma |
| III. Immunosuppression in patients with malignant, solid tumors |
| malignant melanoma |
| carcinoma of the stomach |
| ovarian carcinoma |
| breast carcinoma |
| small cell lung carcinoma |
| retinoblastoma |
| testicular carcinoma |
| glioblastoma |
| rhabdomyosarcoma |
| neuroblastoma |
| Ewing's sarcoma |
| lymphoma |
| IV. Autoimmune diseases |
| rheumatoid arthritis |
| diabetes type I |
| chronic hepatitis |
| multiple sclerosis |
| systemic lupus erythematosus |

TABLE I-continued

| DISEASES OR DISORDERS WHICH CAN BE TREATED BY ADMINISTERING EXPANDED CB STEM CELLS OF THE INVENTION |
|---|
| V. Genetic (congenital) disorders |
| anemias |
| familial aplastic |
| Fanconi's syndrome |
| Bloom's syndrome |
| pure red cell aplasia (PRCA) |
| dyskeratosis congenital |
| Blackfan-Diamond syndrome |
| congenital dyserythropoietic syndromes I-IV |
| Chwachmann-Diamond syndrome |
| dihydrofolate reductase deficiencies |
| formamino transferase deficiency |
| Lesch-Nyhan syndrome |
| congenital spherocytosis |
| congenital elliptocytosis |
| congenital stomatocytosis |
| congenital Rh null disease |
| paroxysmal nocturnal hemoglobinuria |
| G6PD (glucose-6-phosphate dehydrogenase) variants 1, 2, 3 |
| pyruvate kinase deficiency |
| congenital erythropoietin sensitivity deficiency |
| sickle cell disease and trait |
| thalassemia alpha, beta, gamma |
| met-hemoglobinemia |
| congenital disorders of immunity |
| severe combined immunodeficiency disease (SCID) |
| bare lymphocyte syndrome |
| ionophore-responsive combined immunodeficiency |
| combined immunodeficiency with a capping abnormality |
| nucleoside phosphorylase deficiency |
| granulocyte actin deficiency |
| infantile agranulocytosis |
| Gaucher's disease |
| adenosine deaminase deficiency |
| Kostmann's syndrome |
| reticular dysgenesis |
| congenital leukocyte dysfunction syndromes |
| VI. Others |
| osteopetrosis |
| myelosclerosis |
| acquired hemolytic anemias |
| acquired immunodeficiencies |
| infectious disorders causing primary or secondary immunodeficiencies |
| bacterial infections (e.g., Brucellosis, Listerosis, tuberculosis, leprosy) |
| parasitic infections (e.g., malaria, Leishmaniasis) |
| fungal infections |
| disorders involving disproportions in lymphoid cell sets and impaired immune functions due to aging |
| phagocyte disorders |
| Kostmann's agranulocytosis |
| chronic granulomatous disease |
| Chediak-Higachi syndrome |
| neutrophil actin deficiency |
| neutrophil membrane GP-180 deficiency |
| metabolic storage diseases |
| mucopolysaccharidoses |
| mucolipidoses |
| miscellaneous disorders involving immune mechanisms |
| Wiskott-Aldrich Syndrome |
| $\alpha$1-antitrypsin deficiency |

In one embodiment, the Expanded CB Stem Cells are administered to a patient with a hematopoietic deficiency. Hematopoietic deficiencies whose treatment with the Expanded CB Stem Cells of the invention is encompassed by the methods of the invention include but are not limited to decreased levels of either myeloid, erythroid, lymphoid, or megakaryocyte cells of the hematopoietic system or combinations thereof, including those listed in Table I.

Among conditions susceptible to treatment with the Expanded CB Stem Cells of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage.

Expanded CB Stem Cells also can be used in the treatment or prevention of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome, myelofibrosis, thrombocytopenia. Severe thrombocytopenia may result from genetic defects such as Fanconi's Anemia, Wiscott-Aldrich, or May-Hegglin syndromes and from chemotherapy and/or radiation therapy or cancer. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Thrombocytopenia may also result from marrow invasion by carcinoma, lymphoma, leukemia or fibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenytoin or carbamazepine, antithyroids such as propylthiouracil and methimazole and diuretics. Transplantation of the Expanded CB Stem Cells can be used in preventing or treating the bone marrow suppression or hematopoietic deficiencies which often occur in subjects treated with these drugs.

Hematopoietic deficiencies may also occur as a result of viral, microbial or parasitic infections and as a result of treatment for renal disease or renal failure, e.g., dialysis. Transplantation of Expanded CB Stem Cell populations may be useful in treating such hematopoietic deficiency.

Various immunodeficiencies, e.g., in T and/or B lymphocytes, or immune disorders, e.g., rheumatoid arthritis, may also be beneficially affected by treatment with the Expanded CB Stem Cells. Immunodeficiencies may be the result of viral infections (including but not limited to HIVI, HIVII, HTLVI, HTLVII, HTLVIII), severe exposure to radiation, cancer therapy or the result of other medical treatment.

6.10 Banks of Frozen, Expanded Cord Blood Stem Cells

Since according to the present invention, matching of HLA-type is not necessary for therapeutic use of the Expanded CB Stem Cells, it is now practical to store frozen Expanded CB Stem Cells since the present invention teaches that useful amounts can practically be stored. In the prior art, since it was expected that HLA matching to the recipient would generally be necessary to find a useful sample of Expanded CB Stem Cells for therapeutic use, an unattainably large number of different Expanded CB Stem Cell samples had to be stored to make it feasible generally to find a match for a patient, the large numbers making it impractical to store expanded samples, due to the even larger amount of storage space needed to store expanded units. In contrast, and in accordance with the present invention, no HLA matching is required, and thus, the generation of a "bank" of CB Stem Cells which have been expanded and then cryopreserved, useful for the general human population to use in stem cell transplantation, is feasible, since any Expanded CB Stem Cell sample in the bank could feasibly be used with any recipient in a therapeutic method of the invention.

Once the Expanded CB Stem Cells are obtained and cryopreserved, the cryopreserved samples can be stored in a bank (a repository for the collection of samples). The bank can consist of one or more physical locations. Thus, the present invention is also directed to a collection of frozen Expanded CB Stem Cell samples in a bank. The collection can comprise at least 50, 100, 200, 250, 300, 400, 500, 600, 700, 750, 800, 1,000, 2,000, 3,000, 5,000, 7,500, 10,000, 25,000, 50,000 or 100,000 samples of Expanded CB Stem Cells, each sample derived from the umbilical cord blood and/or placental cord blood of a human at birth. In another embodiment, the bank comprises frozen mixtures of two or more different Expanded CB Stem Cell samples, each different sample derived from the umbilical cord blood and/or placental cord blood of a different human at birth, e.g., pooled as described above. The Expanded CB Stem Cell samples are stored at a temperature no warmer than −20° C., preferably at −80° C. In a preferred embodiment, samples can be cryogenically stored in liquid nitrogen (−196° C.) or its vapor (−165° C.).

In certain embodiments, individual samples of Expanded CB Stem Cells can be mixed prior to cryopreservation. In another embodiment, the mixture contains Expanded CB Stem Cells of at least 2, at least 3, at least 4, at least 5 or at least 6 or more different HLA types.

In a preferred embodiment, all or most of the samples of Expanded CB Stem Cells present in the bank have greater than 75 million viable $CD34^+$ cells, as determined prior to cryopreservation.

6.11 Apparatus, Computer and Computer Program Product Implementations

The selection of appropriate frozen Expanded CB Stem Cell populations for administration to a patient without regard to the HLA types of the Expanded CB Stem Cells or the patient can be implemented by use of a computer program product that comprises a computer program mechanism embedded in a computer readable storage medium. Some embodiments of the present invention provide a computer system or a computer program product that encodes or has instructions for performing selecting and outputting an identifier and optionally robotic retrieval of a frozen stored Expanded CB Stem Cell sample. The identifier distinguishes one frozen, Expanded CB Stem Cell sample from other frozen, Expanded CB Stem Cell samples that are stored in a bank of frozen Expanded CB Stem Cell samples as described above, and thus the identifier is unique to each sample. Preferably, the collection of identifiers is stored in one or more computer databases, wherein each identifier is preferably associated with information on the physical location of the Expanded CB Stem Cell sample associated with the identifier, and/or with information on one or more other characteristics of the sample, including but not limited to, total hematopoietic stem cell or hematopoietic stem and progenitor cell count (e.g., total $CD34^+$ cell count) of the sample, total nucleated cell count of the sample, percentage hematopoietic stem cell or hematopoietic stem and progenitor cells (e.g., percentage of $CD34^+$ cells), volume of the sample, sex of the donor, date of freezing of the sample, HLA type of the sample, as described in Section 6.6. Thus, one or more databases store data on each frozen, Expanded CB Stem Cell sample. The database stores one or more of the following characteristics of the stored, frozen, Expanded CB Stem Cell sample, including but not limited to, total $CD34^+$ cell count of the sample, total nucleated cell count of the sample, volume of the sample, sex of the donor, race or ethnicity of the donor, date of freezing of the sample, HLA type of the sample.

Executable instructions for carrying out the selecting and outputting of identifiers, and/or robotic retrieval of the sample can be stored on a CD-ROM, DVD, magnetic disk storage product, or any other computer readable data or program storage product. Such methods can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. Such methods encoded in the computer program product can also be distributed electronically, via the Internet or otherwise, by transmission of a computer data signal (in which the software modules are embedded) either digitally or on a carrier wave.

Some embodiments of the present invention provide a computer program product that contains any or all of the program modules shown in FIG. 1. These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

FIG. 1 illustrates a system 11 that is operated in accordance with one embodiment of the present invention. System 11 comprises at least one computer 10. Computer 10 comprises standard components including a central processing unit 22, memory 36, non-volatile storage 14 accessed via controller 12 for storage of programs and data, user input/output device 32, a network interface 20 for coupling computer 10 to other computers via a communication network (e.g., wide area network 34), power source 24, and one or more busses 30 that interconnect these components. User input/output device 32 comprises one or more user input/output components such as a mouse, display 26, and keyboard 28.

Memory 36 comprises a number of modules and data structures that are used in accordance with the present invention. It will be appreciated that, at any one time during operation of the system, a portion of the modules and/or data structures stored in memory 36 can be stored in random access memory while another portion of the modules and/or data structures can be stored in non-volatile storage 14. In a typical embodiment, memory 36 comprises an operating system 40. Operating system 40 comprises procedures for handling various basic system services and for performing hardware dependent tasks. Memory 36 further comprises a file system 42 for file management. In some embodiments, file system 42 is a component of operating system 40.

Memory 36 further discloses a number of modules including a selecting module 70 for selecting an identifier from a plurality of (preferably of at least 50, 100, 200, 250, 500, 750, 1000, 1500, 2,000, 3,000, 5,000, 7,500, 10,000, 25,000, 50,000 or 100,000) identifiers stored in a computer database, each identifier identifying a frozen, stored expanded human cord blood stem cell sample derived from the umbilical cord blood and/or placental blood of a different human individual at birth, wherein the selecting does not take into account the respective HLA types of the stored frozen expanded human cord blood stem cell samples corresponding to the respective identifiers, an outputting or displaying module 72 for outputting or displaying the identifier and optionally associated information to a user, an internal or external component of a computer, a remote computer, or to storage on a computer readable medium, and an optional retrieval module 74 for robotically retrieving the identified frozen expanded cord blood stem cell sample. The selection module can carry out computer-implemented selecting as described in Section 6.6 above. It will be appreciated that one or more of these modules can be run on computer 10 or any other computer that is addressable by computer 10. Thus, the present invention encompasses systems 11 that have more than one computer, with each such computer optionally storing some or all of Expanded CB Stem Cell sample data 44 and performing any or all of the methods disclosed herein. In some embodiments, system 11 is a cluster of computers.

In one embodiment of the invention, a computer-implemented method for selecting a frozen expanded human cord blood stem cell sample for use in providing hematopoietic function to an immunodeficient human patient is provided, which method comprises the following steps performed by a suitably programmed computer: (a) selecting an identifier from a plurality of at least 50, 100, 200, 250, 300, 400, 500, 600, 700, 750, 800, 1,000, 2,000, 3,000, 5,000, 7,500, 10,000, 25,000, 50,000 or 100,000 identifiers stored in a computer database, each identifier identifying a frozen stored expanded human cord blood stem cell sample derived from the umbilical cord blood and/or placental blood of a different human individual at birth, wherein the selecting does not take into account the respective HLA types of the stored frozen expanded human cord blood stem cell samples corresponding to the respective identifiers, wherein the selecting is for administration of the expanded human cord blood stem cell sample identified by said identifier to an immunodeficient human patient; and (b) outputting or displaying the selected identifier. In particular embodiments, the identifier is outputted or displayed to a user, an internal or external component of a computer, a remote computer, or to storage on a computer readable medium. The outputting or displaying can also output or display information on the physical location of the expanded human cord blood stem cell sample identified by the identifier. In a specific embodiment, the method further comprises implementing robotic retrieval of the identified frozen, expanded human cord blood stem cell sample. The selecting can be as described in Section 6.6.

In another embodiment of the invention, a computer program product is provided for use in conjunction with a computer system, which computer program product comprises a computer readable storage medium and a computer program mechanism embedded therein, the computer program comprising (a) executable instructions for selecting an identifier from a plurality of at least 50, 100, 200, 250, 300, 400, 500, 600, 700, 750, 800, 1,000, 2,000, 3,000, 5,000, 7,500, 10,000, 25,000, 50,000 or 100,000 identifiers stored in a computer database, each identifier identifying a frozen stored expanded human cord blood stem cell sample derived from the umbilical cord blood and/or placental blood of a different human individual at birth, wherein the selecting does not take into account the respective HLA types of the stored frozen expanded human cord blood stem cell samples corresponding to the respective identifiers, wherein the selecting is for administration of the expanded human cord blood stem cell sample identified by said identifier to an immunodeficient human patient; and (b) executable instructions for outputting or displaying the selected identifier. In particular embodiments, the identifier is outputted or displayed to a user, an internal or external component of a computer, a remote computer, or to storage on a computer readable medium. In a specific embodiment, the computer program product further comprises executable instructions for implementing robotic retrieval of the identified frozen, expanded human cord blood stem cell sample. The selecting can be as described in Section 6.6 above.

In yet another embodiment, the present invention provides an apparatus comprising a processor; a memory, coupled to the processor, the memory storing a module, the module comprising (a) executable instructions for selecting an identifier from a plurality of at least 50, 100, 200, 250, 300, 400, 500, 600, 700, 750, 800, 1,000, 2,000, 3,000, 5,000, 7,500, 10,000, 25,000, 50,000 or 100,000 identifiers stored in a computer database, each identifier identifying a frozen stored expanded human cord blood stem cell sample derived from the umbilical cord blood and/or placental blood of a different human individual at birth, wherein the selecting does not take into account the respective HLA types of the stored frozen expanded human cord blood stem cell samples corresponding to the respective identifiers, wherein the selecting is for administration of the expanded human cord blood stem cell sample identified by said identifier to an immunodeficient human patient; and (b) executable instructions for outputting or displaying the selected identifier. In particular embodiments, the identifier is outputted or displayed to a user, an internal or external component of a computer, a remote computer, or to storage on a computer readable medium. In a specific embodiment, the apparatus further comprises executable instructions for implementing robotic retrieval of the identified frozen, expanded human cord blood stem cell sample. The selecting can be as described in Section 6.6.

Alternative embodiments for implementing the methods and producing the Stem Cell and Expanded CB Stem Cell populations of the present invention will be apparent to one of skill in the art and are intended to be comprehended within the accompanying claims. The experimental examples in Sections 7-10, infra, are offered by way of illustration and not by way of limitation.

7. EXAMPLE: ENRICHMENT AND EXPANSION OF CD34$^+$ CELLS

This data presented herein supports the usefulness of CD34$^+$ cord blood stem cells which have been expanded ex vivo with an agonist of Notch function as an off-the-shelf, non-HLA matched product to provide rapid but transient myeloid engraftment and to potentially facilitate autologous hematopoietic recovery in immunodeficient patients. In the prior art, it was not feasible to perform ex vivo expansion in advance as the need for HLA-matching required an unattainable number of pre-expanded units in order for an individual patient to find a suitably matched unit. In contrast, where no, or limited, HLA-matching, is required for the expanded stem cell product, generation of a "bank" of pre-expanded and then cryopreserved cells is possible, and the products would be available for immediate use.

7.1 CD34$^+$/CD38$^-$ Versus CD34$^+$

Growth characteristics and generation of SCID repopulating cells (SRC) starting from CD34$^+$ or CD34$^+$CD38$^-$ human cord blood progenitor cell populations were compared. Enriched CD34$^+$CD38$^-$ cord blood progenitors cells were used as the starting cell population for Notch-mediated expansion as described in Delaney et al., 2005, Blood 106:1784-1789. Cells were cultured for 17-21 days in the presence of fibronectin fragments and immobilized engineered Notch ligand (Delta1$^{ext\text{-}IgG}$) or control human IgG in serum free conditions supplemented with cytokines (SCF 300 ng/ml, Flt3L 300 ng/ml, TPO 100 ng/ml, IL-6 10 ng/ml, and IL-3 10 ng/ml, denoted as "5GF"). Delta1$^{ext\text{-}IgG}$ consists of the extracellular domain of Delta1 fused to the Fc domain of human IgG1. No significant difference was observed in absolute numbers of CD34$^+$ cells generated, with a CD34$^+$ cell fold expansion of 138±64 and 163±64, (mean±sem, p=0.1612, data not shown) for the CD34$^+$ versus the CD34$^+$ CD38$^-$ starting cell population, respectively. Assessment of in vivo NOD/SCID repopulating ability at 3, 6 and 10 weeks post infusion did, however, reveal enhanced human engraftment in the marrow of recipient mice when a CD34$^+$ starting cell population was used as compared to a CD34$^+$CD38$^-$ starting cell population (mean CD45% in CD34$^+$ versus CD34$^+$CD38$^-$ starting cell populations cultured in the presence of Delta1$^{ext\text{-}IgG}$: 3 weeks; 6.7% versus 1.6%, p=0.02 and 10 weeks: 1.0% vs 0.2%, p=0.1). It was further determined that the 5GF combination was superior to use of combinations utilizing fewer cytokines with respect to both in vitro generation of CD34$^+$ cells and SRC frequency as determined by limiting dilution analysis (data not shown).

7.2 Culture of Cord Blood Progenitor Cells with Delta1$^{ext\text{-}IgG}$ Results in Increased SCID Repopulating Cell (SRC) Frequency Having identified the optimal conditions for Notch-mediated generation of UCB repopulating cells, 5 independent experiments were carried out to test this closed system for generation of stem/progenitor cells. Human CD34$^+$ cord blood cells were cultured for 17 days with Delta1$^{ext\text{-}IgG}$ immobilized to the surface of the tissue culture vessel together with CH-296 fibronectin fragments in the presence of cytokines (IL-3 at 10 ng/ml, IL-6 and TPO at 100 ng/ml, SCF and Flt3 ligand at 300 ng/ml) and low density lipoproteins (LDL at 20 ng/ml) in serum free medium. The number of repopulating cells generated was determined using quantitative limit dilution assays in which groups of 8 to 15 mice received $1.5\times10^5$, $3\times10^4$, or $6\times10^3$ non-cultured cells or the cultured progeny of $3\times10^4$, $6\times10^3$ or $1.2\times10^3$ cells. Of note, mice that received non-cultured cells also received $2\times10^5$ irradiated CD34$^-$ cells as accessory supporting cells to facilitate engraftment. Such accessory cells have not been required for cultured cells as their function is provided by differentiated myeloid cells in the culture.

Figure 2A:
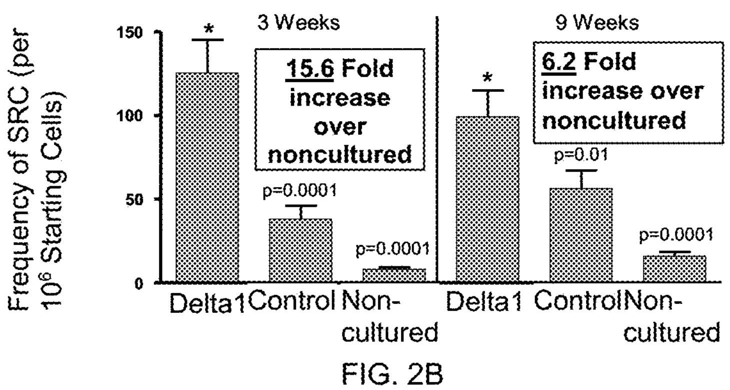

The frequency of repopulating cells in the starting cell population, determined using Poisson analysis with L-Calc™ software, demonstrated a 15.8 fold increase in SRC frequency in Delta1$^{ext\text{-}IgG}$-cultured cells compared to non-cultured cells at 3 weeks (p=0.0001) post infusion of cells and a 6.3 fold increase in SRC frequency at 9 weeks (p=0.0001) (FIG. 2*a*), thus indicating a significant increase in repopulating ability after culture with Delta1$^{ext\text{-}IgG}$.

Figure 2B:
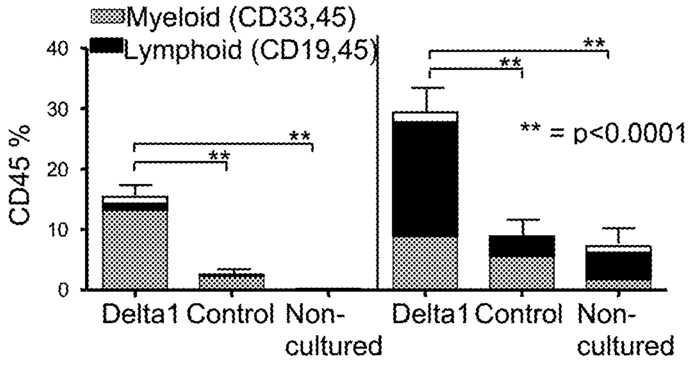

In addition, the fold expansion of the human CD34$^+$ cells and the in vivo level of human engraftment including lineage assessment (lymphoid versus myeloid) of the human cells present was determined. In these 5 experiments, there was a mean fold expansion of CD34$^+$ cells of 230±53 (mean±sem) for the Delta1$^{ext\text{-}IgG}$ cultured cells versus 65±31 (mean±sem) for the control cultured cells (p=0.03) (data not shown) and demonstrated significantly higher engraftment of human CD45$^+$ cells, as well as CD33$^+$ myeloid and CD19$^+$ B cells from the Delta1$^{ext\text{-}IgG}$-cultured cells (FIG. 2*b*). Although cells cultured with Delta1$^{ext\text{-}IgG}$ led to increased overall hematopoietic reconstitution at 9 versus 3 weeks, this was due primarily to an increase in engrafted lymphoid cells, presumably due to expansion of mature cells, whereas myeloid engraftment decreased suggesting at least a portion of engrafting cells were short term in nature.

Figure 3:
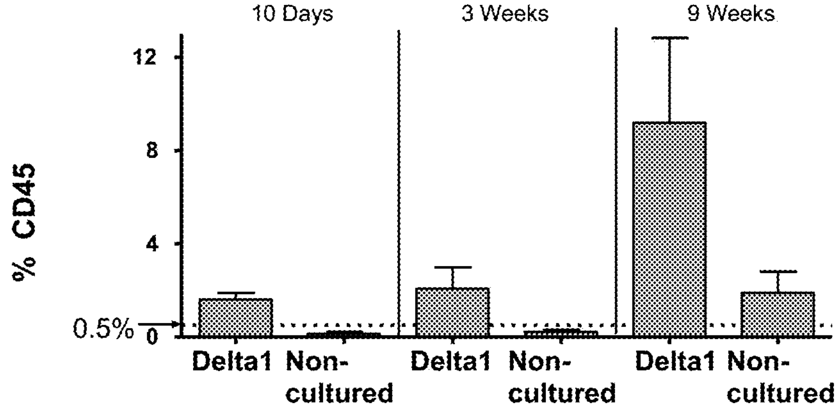

7.3 Early Engrafting Potential of Delta1$^{ext\text{-}IgG}$-Cultured UCB Progenitors In three independent experiments, in which the engraftment of Delta1$^{ext\text{-}IgG}$-cultured human umbilical cord blood stem and progenitor cells produced as described in Section 7.2, supra, was compared to engraftment of non-Delta1$^{ext\text{-}IgG}$-cultured stem and progenitor cells, there was no measurable contribution to engraftment 10 days post transplant in mice receiving non-cultured cord blood cells, whereas the mice that received Delta1$^{ext\text{-}IgG}$-cultured cells all engrafted at a level of >0.5% human engraftment consisting of >95% myeloid cells as measured by co-expression of the human antigens, CD33/CD45 (FIG. 3). Taken together, the above data suggests that culture of cord blood progenitors with Delta1$^{ext\text{-}IgG}$ dramatically enhances the in vitro generation and frequency of NOD/SCID repopulating cells resulting in improvement in the kinetics and level of human engraftment in a NOD/SCID mouse model.

Figure 4A:
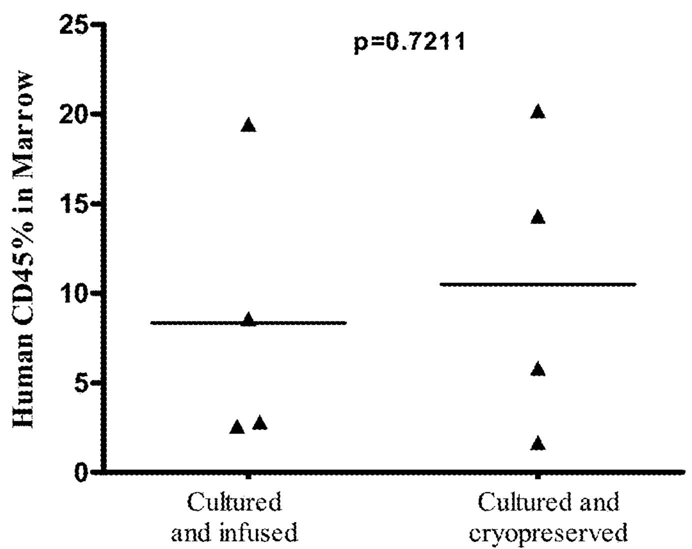
Figure 4B:
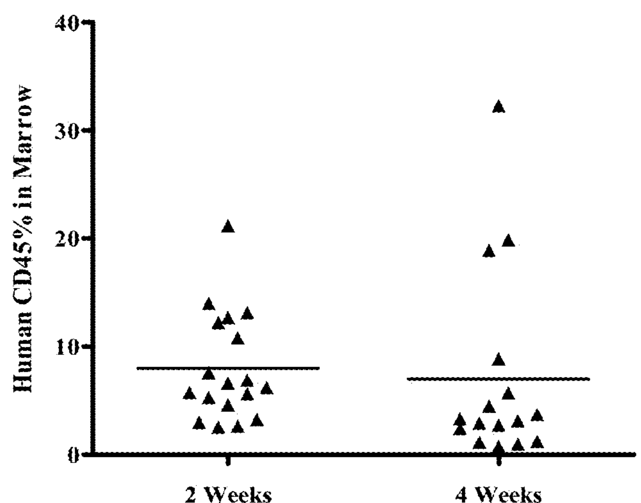
Figure 4C:
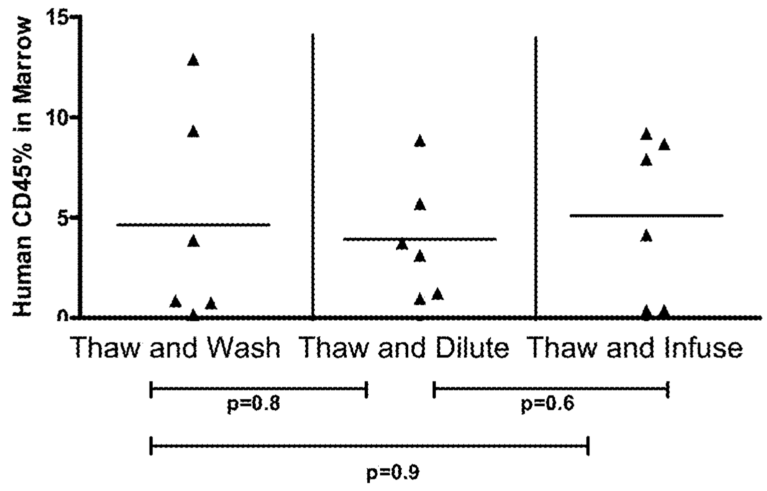

7.4 In Vivo Repopulating Ability is Retained Following Cryopreservation of the Expanded Cell Product Using an immunodeficient mouse model, the ability of ex vivo expanded cryopreserved progenitor cells to engraft was evaluated. The cells were expanded according to the method set forth in Section 7.2, supra. Initial experiments compared in vivo repopulating ability of human expanded cells that were directly infused into immunodeficient mice upon harvest versus those that were harvested post expansion and cryopreserved for future use. There were no significant differences observed in the in vivo repopulating ability of cells that were cultured, cryopreserved (in standard media used for hematopoietic cell cryopreservation containing DMSO), and then thawed prior to transplant when compared to expanded progenitor cells that were harvested at the end of culture and freshly infused (FIG. 4*a*). Additional experiments have confirmed that repopulating ability of the expanded cell product is retained following cryopreservation. As shown in FIG. 4*b*, all mice that received human expanded cryopreserved cells engrafted (defined >0.5% human CD45 in the marrow) with an average overall human engraftment of 8% at 2 weeks post infusion and 7% at 4 weeks post infusion. Lastly, various thawing methodologies were compared (thaw and wash, thaw and dilute with dextran/HSA and thaw and directly infuse) and have also not seen a significant difference in the three methods evaluated (FIG. 4*c*).

Figure 5:
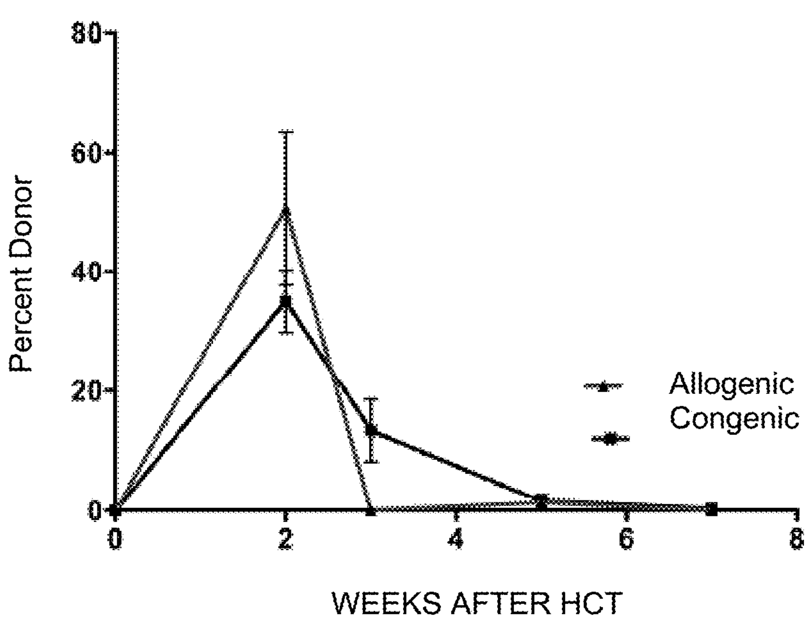

7.5 Murine Hematopoietic Progenitor Cells Cultured with Delta1$^{ext\text{-}IgG}$ Provide Short-Term Engraftment in H-2 Mismatched Recipients and Facilitates Autologous Recovery Following Radiation Exposure The studies described below with a murine model show that expanded numbers of progenitor cells derived from murine hematopoietic progenitors (LSK cells) are capable of providing short term engraftment when transplanted in an H-2 mismatched recipient. LSK cells from C57BL/6.J Ly5.1 (CD45.1) mice were cultured as previously described for four weeks on Delta1$^{ext\text{-}IgG}$ (Dallas et al., 2007, Blood 109:3579-3587). For the congenic transplant, lethally irradiated C57BL/6 (H-2b, CD45.1) mice received 106 Delta1$^{ext\text{-}IgG}$-cultured Ly5.2 (H-2b, CD45.2) primary LSK cells along with 105 C57BL/6 (H-2b, CD45.1) syngeneic whole bone marrow. For the allogeneic transplant, lethally irradiated BALB.c (H-2d, CD45.1) recipients received 106 Ly5.2 (H-2b, CD45.2) Delta1$^{ext-IgG}$-cultured LSK cells along with 105 BALB.c (H-2d, CD45.1) syngeneic whole bone marrow. Peripheral blood from mice were analyzed by FACS analysis at various times after transplantation to evaluate for donor chimerism (FIG. 5). The data show that the Delta cultured cells are able to provide short-term donor engraftment in transplant with major H-2 mismatch.

Figure 6:
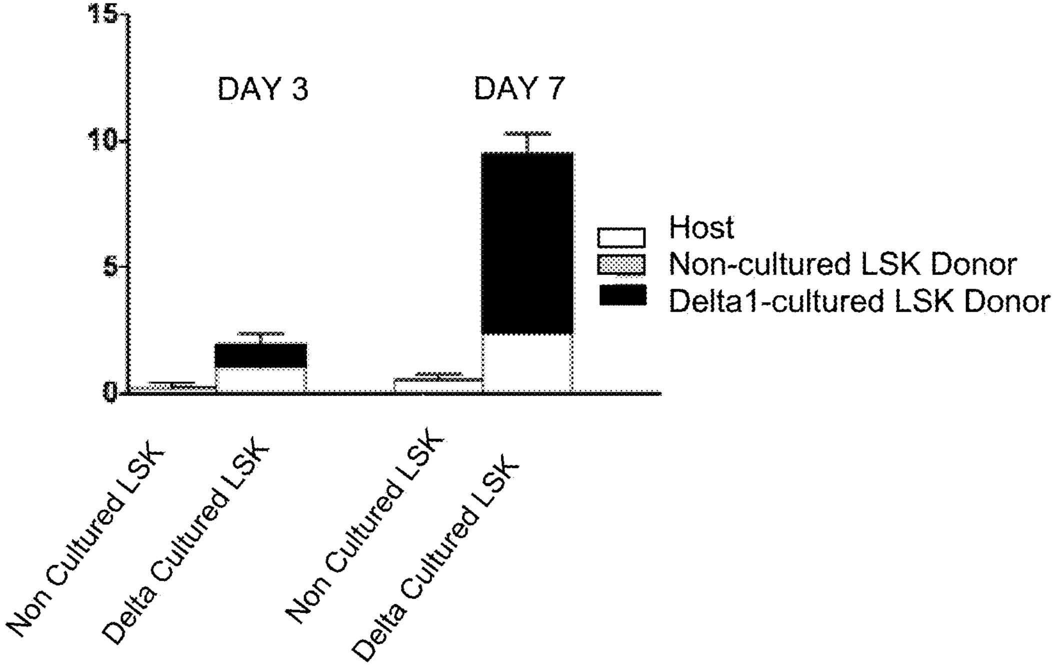

Furthermore, the data indicate that Delta1$^{ext-IgG}$-cultured cells have enhanced hematopoietic engraftment early after irradiation compared to LSK bone marrow cells (which are depleted of T cells potentially able to cause graft-versus-host disease) in a competitive repopulation assay. This data demonstrates higher levels of early bone marrow repopulation following infusion of cells cultured with Delta1$^{ext-IgG}$ compared to non-cultured precursors. The marrow of mice receiving allogeneic cells following culture with Delta1$^{ext-IgG}$ contained a significantly greater number of the allogeneic donor cells than mice that received non-cultured allogeneic donor LSK cells. Furthermore, assessment of engraftment derived from syngeneic cells, provided to ensure survival of the recipient mice, demonstrated facilitation of engraftment of the syngeneic cells when co-transplanted with Delta1$^{ext-IgG}$-cultured allogeneic cells. The number of cells derived from the host was higher in recipients of the Delta1$^{ext-IgG}$-cultured cells compared to non-cultured allogeneic cells (FIG. 6). Thus, this data indicates that engraftment by cultured cells can occur in mismatched settings, and moreover the Delta1$^{ext-IgG}$-cultured cells can facilitate engraftment of syngeneic cells, further suggesting their potential for facilitating recovery of autologous residual stem cells remaining after radiation.

Figure 9A:
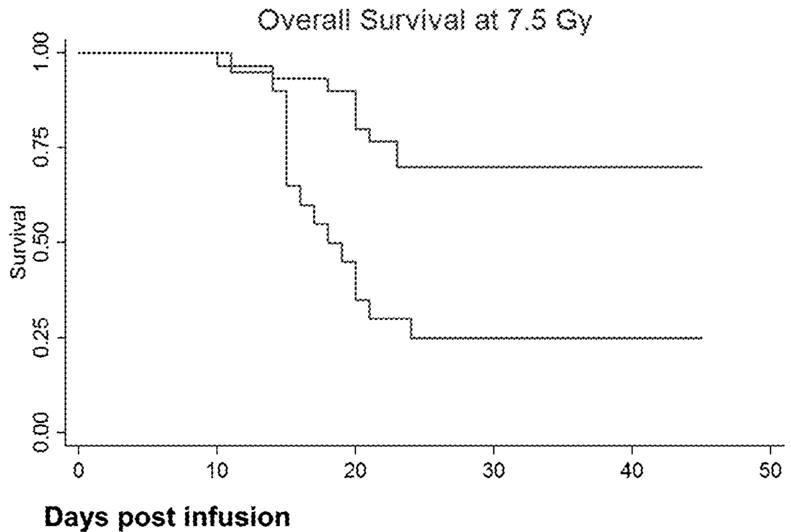
Figure 9B:
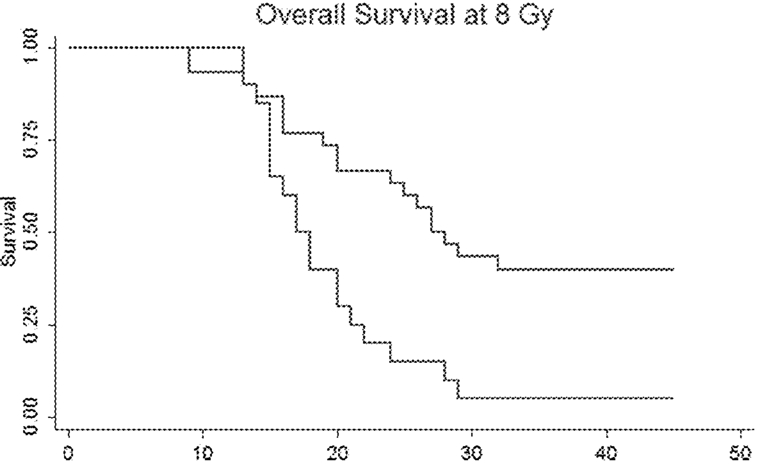
Figure 10:
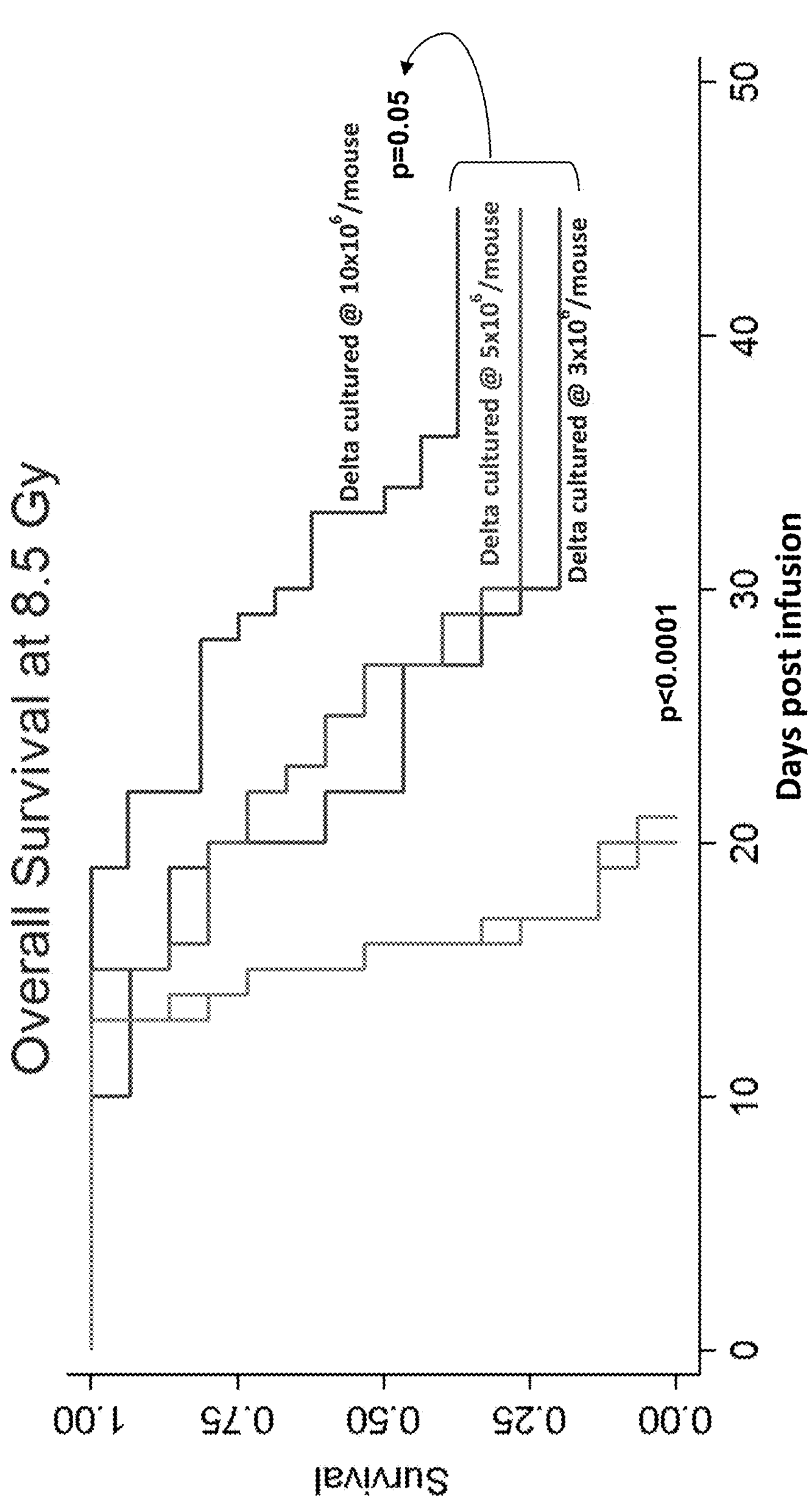
Figure 11A:
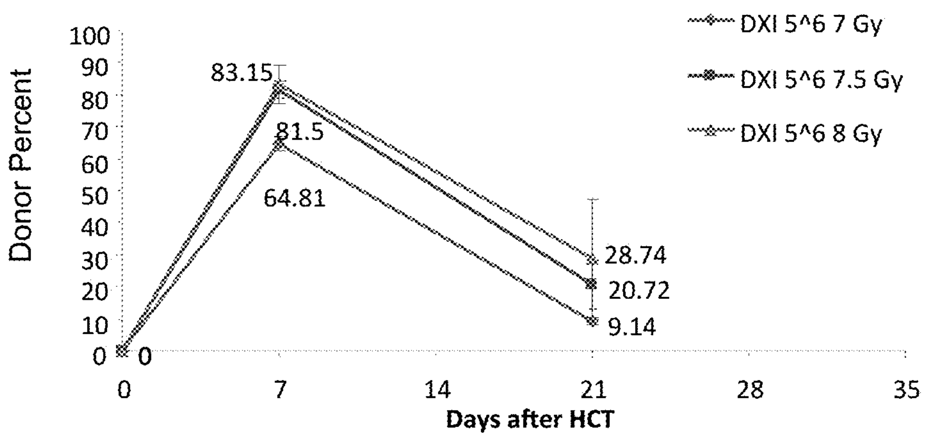
Figure 11B:
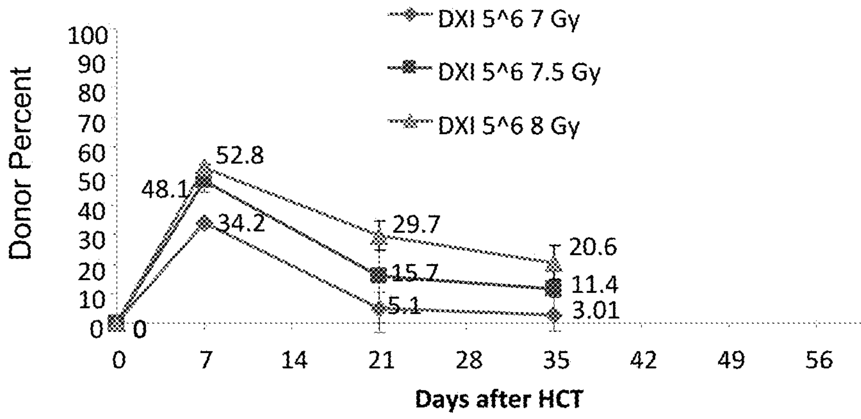

In separate experiments, murine Ly5a Lin-Sca-1 c-kit+ cells (H-2b, CD45.1) ("LSK") cells obtained from the bone marrow of C57 black mice by flow cytometric sorting (103) were expanded by culturing the cells with growth medium and immobilized Delta1$^{ext-IgG}$ (expanded LSK cells). Control (unexpanded) LSK cells were cultured with IgG. The growth medium (Iscoves modified Dulbecco medium) was supplemented with 20% FBS and 4 growth factors (4GF): murine stem cell factor, human Flt-3 ligand, and human IL-6, each at 100 ng/mL, and human IL-11 at 10 ng/mL (PeproTech, Rocky Hill, NJ). Cell density was maintained at approximately $2.5\times10^5$ cells/cm$^2$ by transferring the cultures to larger vessels every 3 to 5 days during the first 2 weeks (see Dallas et al., 2007, Blood 109:3579-3587). After 14 days of culture, the cells were harvested and transplanted into irradiated Balb-c (H-2d, CD45.2) mice. FIG. 7 is a schematic drawing of this experimental protocol. FIGS. 8*a*-8*b* depict the level of engraftment of the expanded and non-expanded LSK cells in either bone marrow (FIG. 8*a*) or peripheral blood (FIG. 8*b*) of lethally irradiated Balb-c mice as a result of carrying out the protocol set forth in FIG. 7, measured as donor percent (percentage of donor cells in bone marrow or peripheral blood as determined by immunophenotyping and FACS analysis). The results confirmed that effective engraftment was achieved when expanded stem and progenitor cells were infused in a mismatched setting after a single dose of radiation. In a similar experiment, $5\times10^6$ cryopreserved LSK cells, expanded as described above, were infused into mice exposed to 7.5 Gy or 8 Gy of radiation. FIGS. 9*a*-9*b* show that mice infused with the expanded LSK cells (indicated as "Delta") had a greater survival rate as compared to a control group infused with saline. Similarly, the overall survival of mice lethally irradiated at 8.5 Gy was increased after infusion of either $3\times10^6$, $5\times10^6$, or $10\times10^6$ Delta1$^{ext-IgG}$-cultured (expanded) LSK cells as compared to $1\times10^6$ or $3\times10^6$ IgG-cultured (non-expanded) LSK cells (FIG. 10). In another experiment, following the protocol set forth in FIG. 7, donor engraftment of mismatched expanded LSK cells (DXI) was enhanced with increasing dose of radiation as measured by the percentage of donor cells (donor percent) in bone marrow and peripheral blood, as determined by immunophenotyping and FACS analysis (FIGS. 11*a*-11*b*).

7.6 Preliminary Results of a Phase I Clinical CBT Trial

Figure 12:
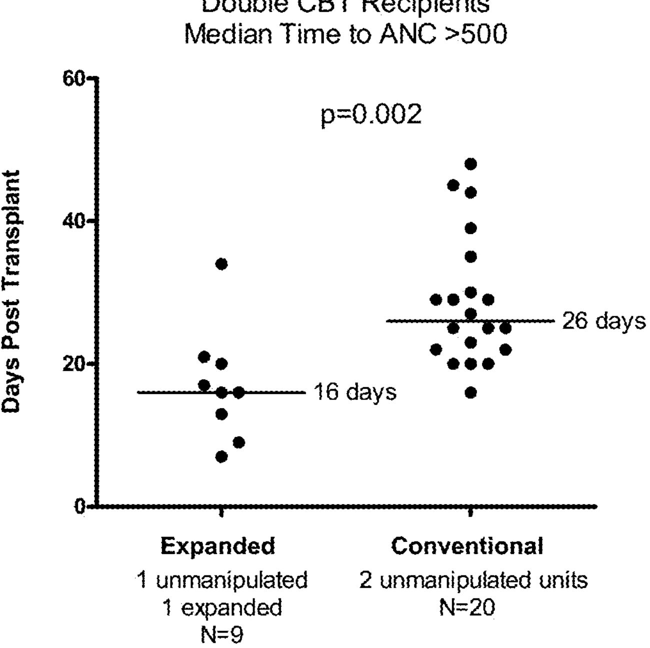

Direct clinical translation of the above has resulted in an ongoing Phase I cord blood transplantation trial (FHCRC Protocol 2044) using ex vivo expanded cord blood progenitor cells following myeloablative conditioning. Results from the current Phase I trial have not only demonstrated safety of this protocol, but more importantly have demonstrated rapid myeloid engraftment derived from ex vivo expanded hematopoietic progenitors and consequently, a significant reduction in median time to an absolute neutrophil count of 500/μl to just 14 days. This is a statistically significant ($p=0.002$) improvement in time to engraftment when compared to a cohort of patients ($N=20$) with the same treatment regimen at our institution but with two non-manipulated cord blood units who engrafted at a median of 26 days (FIG. 12). The two cohorts did not differ significantly in age, weight, diagnosis or infused cell doses as provided by the non-manipulated units. It has been suggested that an ANC threshold of >100/μl is strongly associated with a survival benefit post allogeneic stem cell transplant (Offner et al., 1996, Blood 88:4058). Among enrolled patients median time to achieve an ANC >100/μl was 9 days versus 19 days in the conventional setting (as above) ($p=0.006$, data not shown).

In the 11 patients analyzed to date, there has been no failure to ex vivo expand the absolute numbers of CD34$^+$ cells available for infusion. The average fold expansion of CD34$^+$ cells was 163 (±43 SEM, range 41-471) and 590 (±124 SEM, range 146-1496) for the total cell numbers, correlating with a significantly higher infused CD34 cell dose (CD34$^+$ cells/kg recipient body weight) derived from the expanded cord blood graft averaging $6\times10^6$ CD34/kg (range 0.93 to $13\times10^6$) versus $0.24\times10^6$ CD34/kg (range 0.06 to $0.54\times10^6$) from the non-manipulated cord blood graft. It is important to note that the unit subjected to ex vivo expansion is CD34-selected and therefore T cell depleted prior to culture initiation. Additional details of the final harvested product, including viability and additional immunophenotyping, can be found in Table II below. As demonstrated in Table II, no CD3$^+$/CD4$^+$ or CD3$^+$/CD8$^+$ cells were identified. No mature T cells are generated during culture. Also, as discussed below, even in this setting where the expanded cells were at least 4/6 HLA-matched to the recipient, there was no contribution to CD3 engraftment from the expanded unit. CD4$^+$/CD3$^-$/CD8$^-$ cells were observed in culture and consistent with monocytes.

TABLE II

Selected Immunophenotyping of Expanded Cell Product at Harvest

| | Percent (range) | Cells/kg (range) |
|---|---|---|
| CD34 | 14.5 (6.2-26) | $6.1\times10^6$ (0.9-13.6) |
| CD7 | 8.1 (5.9-12) | $3.9\times10^6$ (0.3-9.1) |
| CD14 | 11.3 (1.8-23) | $5.6\times10^6$ (0.1-14.6) |
| CD15 | 20.5 (6-36) | $9.0\times10^6$ (1.1-23) |
| CD34$^+$/56$^+$ | 2.9 (1.4-5.8) | $1.7\times10^6$ (0.08-5.3) |
| CD3$^-$/CD16$^+$/56$^+$ | 5.4 (2.2-13.6) | $2.7\times10^6$ (0.1-12.4) |

TABLE II-continued

Selected Immunophenotyping of Expanded Cell Product at Harvest

| | Percent (range) | Cells/kg (range) |
|---|---|---|
| CD20 | 0.1 (0-0.2) | $3.6 \times 10^4$ (0-14) |
| CD3 | 0.2 (0-0.6) | $4.8 \times 10^4$ (0-13) |
| $CD4^{lo}/CD3^{neg}/CD8^{neg}$ | 40.6 (16-67) | $1.7 \times 10^7$ (0.2-6.1) |
| CD8 | 0.1 (0-0.5) | $3.4 \times 10^4$ (0-17) |

Contribution to donor engraftment as derived from the expanded or non-manipulated grafts was determined weekly in the first month beginning at day 7 post-transplant on peripheral blood sorted cell fractions. In eight of the nine engrafted patients there were sufficient numbers of peripheral blood sorted myeloid cells for evaluation and in each of these patients revealed a predominance of donor cell engraftment derived from the expanded cell graft in both the CD33 and CD14 cell fractions. Contribution to early myeloid recovery at day 7 was derived almost entirely from the expanded cell graft, but generally did not persist beyond day 14 to 21 post-transplant. Despite this, time to engraftment was decreased significantly, indicating of a potential facilitating effect exerted by the ex vivo expanded cells on the non-manipulated unit. In all but one patient, as expected, the non-manipulated donor graft has emerged as the source of sustained donor engraftment.

Longer-term in vivo persistence of the expanded cell graft was observed in two patients. In one patient, analysis at day 240 post transplant revealed a portion (10-15%) of the donor CD14, CD56 and CD19 cells were derived from the expanded graft but was no longer present by one year. In the second patient at day 180 post transplant, contribution to engraftment from the expanded cell population at day 180 post transplant in CD33, CD14, CD56 and CD19 cells ranged from 25 to 66% of total donor engraftment. However, the expanded graft did not contribute to $CD3^+$ cell engraftment.

8. EXAMPLE: CLINICAL ENRICHMENT AND EXPANSION

Figure 13:
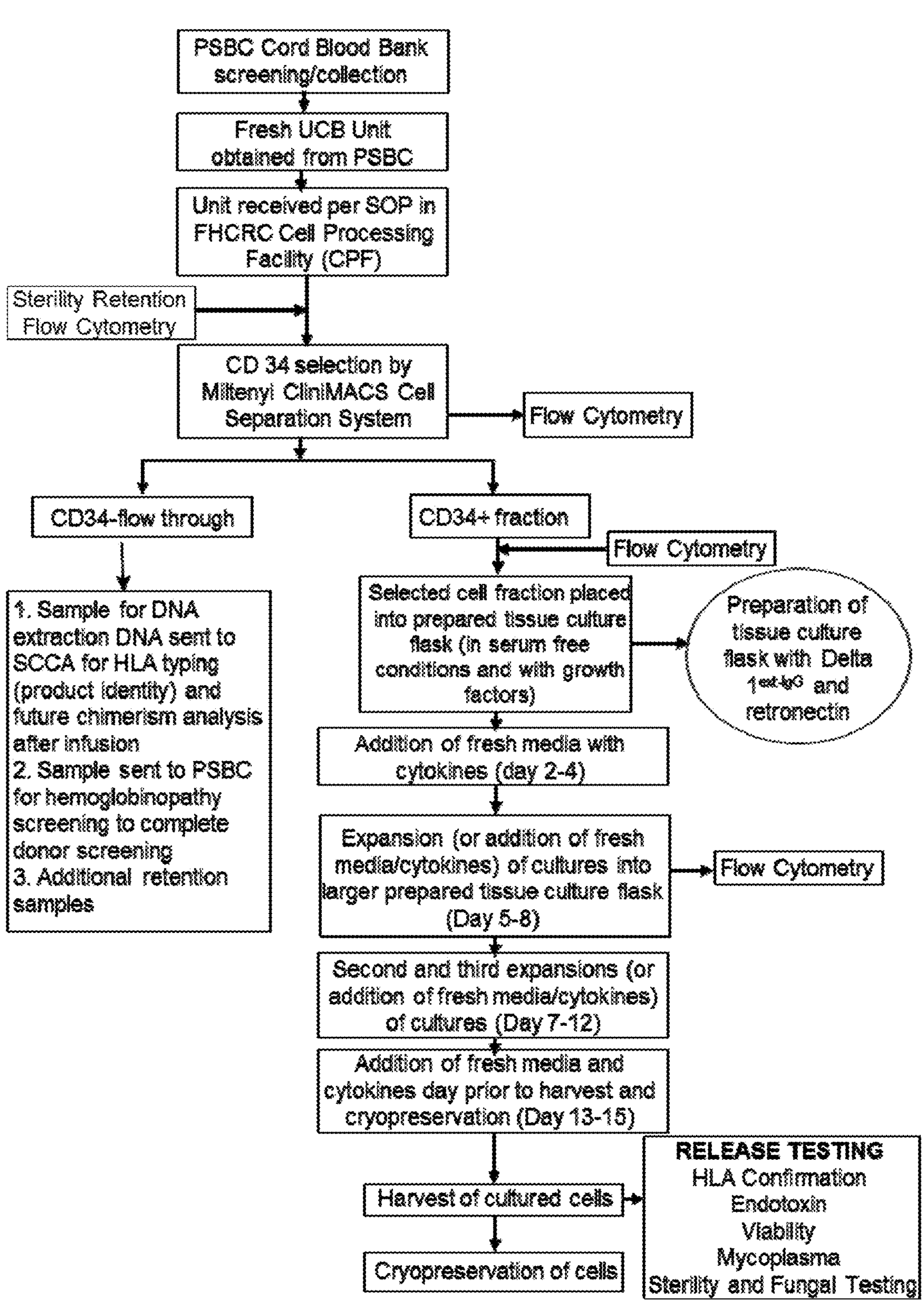
FIG. 13 is a flow chart demonstrating an exemplary procedure for enriching a population of $CD34^+$ cells, and expanding the enriched population.

The following section describes the production and storage of expanded human cord blood stem cell samples, as depicted as a flow chart in FIG. 13.

The umbilical cord blood/placental blood unit(s) were collected from a single human at birth. The collected blood was then mixed with an anti-coagulant to prevent clotting. The blood was stored under quarantine at 4° C. in a monitored refrigerator. The received unit(s) were assessed, and which unit(s) will be processed for expansion was determined. The following information was collected on the units: date received, age in hours of the unit, gestational age of the donor in weeks, sex of the donor, and volume of the unit. Further, total nucleated cell count and total $CD34^+$ cell count of each unit was determined and percent $CD34^+$ cells was calculated. If the unit had less than 3.5 million $CD34^+$ cells, the unit was discarded. When a unit was selected for expansion, it was removed from quarantine and assigned a unique Lot Number identifier, which it retains throughout the manufacturing process.

Prior to planned initiation of expansion cultures, tissue culture vessels were first coated overnight at 4° C. or a minimum of 2 hours at 37° C. with $Delta1^{ext\text{-}IgG}$ at 2.5 μg/ml and RetroNectin® (a recombinant human fibronectin fragment) (Clontech Laboratories, Inc., Madison, WI) at 5 μg/ml in phosphate buffered saline (PBS). The flasks were then washed with PBS and then blocked with PBS-2% Human Serum Albumin (HSA). The fresh cord blood unit was processed to select for $CD34^+$ cells using the CliniMACS® Plus Cell Separation System. Prior to CD34 selection, an aliquot of the fresh cord blood unit was checked for total cell count and CD34 content. Both $CD34^+$ and $CD34^-$ cell fractions were recovered after processing. After enrichment, the percentage of $CD34^+$ cells in the sample increased by 88- to 223-fold relative to the percentage of $CD34^+$ cells in the sample prior to enrichment. DNA was extracted from a sample of the $CD34^-$ cell fraction for initial HLA typing. The enriched $CD34^+$ cell fraction was resuspended in final culture media, which consists of STEMSPAN™ Serum Free Expansion Medium (StemCell Technologies, Vancouver, British Columbia) supplemented with rhIL-3 (10 ng/ml), rhIL-6 (50 ng/ml), rhTPO (50 ng/ml), rhFlt-3L (50 ng/ml), rhSCF (50 ng/ml).

The $CD34^+$ enriched cells were added to the specifically labeled and prepared tissue culture vessels at a concentration of ≤$1.8\times10^4$ total nucleated cells/cm2 of vessel surface area, and then placed into individually monitored and alarmed incubators dedicated solely to that lot of product. After 2-4 days of culture, 50% of the original volume of fresh culture media (as above) was added to the vessels. The cell culture vessels were removed from the incubator periodically (every 1-3 days), and examined by inverted microscope for cell growth and signs of contamination. On day 5-8, the vessel was gently agitated to mix the cells, and a 1 ml sample was removed for in process testing. The sample of cells was counted and phenotyped for expression of CD34, CD7, CD14, CD15 and CD56. Throughout the culture period, cells were transferred to additional flasks as needed when cell density increases to ≥$8\times10^5$ cells/ml. On the day prior to harvesting the cells for cryopreservation, fresh media was added.

On day 14-16, the expanded cell population was harvested for cryopreservation. The vessels were agitated and the entire contents transferred to sterile 500 ml centrifuge tubes. The harvested cells were centrifuged and then washed one time by centrifugation in PBS and resuspended in a cryoprotectant solution containing HSA, Normosol-R (Hospira, ake Forrest, IL) and Dimethylsulfoxide (DMSO). Samples for completion of release testing were taken. The Expanded CB Stem cell population product was frozen in a controlled-rate freezer and transferred to storage in a vapor-phase liquid nitrogen (LN2) freezer.

At the end of the culture period, the resulting cell population was heterogeneous, consisting of $CD34^+$ progenitor cells and more mature myeloid and lymphoid precursors, as evidenced by flow cytometric analysis for the presence of CD34, CD7, CD14, CD15 and CD56 antigens. Typical flow cytometry characterization of the expanded cells at the end of the expansion period is presented in Table III below.

TABLE III

Expanded Cell Phenotype (N = 9, *N = 5)

| | Mean Percent (range) |
|---|---|
| CD34 | 12.8 (4.9-25) |
| CD7 | 9.7 (4.3-21) |
| CD14 | 7.7 (3.5-22) |
| CD15 | 42 (23-66) |
| $CD34^+/56^+$ | 1.8 (0.7-3.1) |
| $CD3^-/CD16^+/56^+$ | 3.5 (0-9.5) |
| CD20* | 0.4 (0-1.2) |

TABLE III-continued

| Expanded Cell Phenotype (N = 9, *N = 5) | |
|---|---|
| | Mean Percent (range) |
| $CD3^{+}4^{+}$* | 0.7 (0.04-1.4) |
| $CD3^{+}8^{+}$* | 0 |
| TNC Fold Expansion | 1586 (617-3337) |
| CD34 Fold Expansion | 204 (100-387) |

There was a significant increase of $CD34^{+}$ and total cell numbers during the culture period, ranging from 100 to 387 fold expansion of $CD34^{+}$ cells and 617 to 3337 fold expansion of total cell numbers (N=9 individual cord blood units, processed per the final clinical expansion procedures as described above). There was essentially a complete lack of T cells as measured by immunophenotyping. Functionally, these cells are capable of multi-lineage human hematopoietic engraftment in a NOD/SCID mouse model as described above.

Data from ten full-scale ex vivo expansions are presented in Table IV below. The average fold expansion for total cell numbers was 1723±230 (mean±sem) and for $CD34^{+}$ cells was 179±30 (mean±sem).

TABLE IV

Pre- and Post-expansion absolute cell numbers and fold expansion

| | TNC (total number cells) | | | CD34 | | | Number banked (cryopreserved) Cells | | | | |
|---|---|---|---|---|---|---|---|---|---|---|---|
| Run | Starting Number | Ending Number | Fold Expansion | Starting Number | Ending Number | Fold Expansion | TNC | CD34# | # Bags | TNC/Bag | CD34/Bag |
| 1 | $1.9 \times 10^{6}$ | $2.01 \times 10^{9}$ | 1068 | $1.66 \times 10^{6}$ | $2.13 \times 10^{8}$ | 129 | n/a | n/a | n/a | n/a | n/a |
| 2 | $1.76 \times 10^{6}$ | $1.20 \times 10^{9}$ | 690 | $1.41 \times 10^{6}$ | $3.04 \times 10^{8}$ | 216 | n/a | n/a | n/a | n/a | n/a |
| 3 | $2.60 \times 10^{6}$ | $5.47 \times 10^{9}$ | 2104 | $2.29 \times 10^{6}$ | $2.69 \times 10^{8}$ | 117 | $4.20 \times 10^{9}$ | $2.06 \times 10^{8}$ | 2 | $2.10 \times 10^{9}$ | $1.03 \times 10^{8}$ |
| 4 | $2.40 \times 10^{6}$ | $4.67 \times 10^{9}$ | 1944 | $2.04 \times 10^{6}$ | $6.07 \times 10^{8}$ | 298 | $2.90 \times 10^{9}$ | $3.77 \times 10^{8}$ | 1 | $2.90 \times 10^{9}$ | $3.77 \times 10^{8}$ |
| 5 | $2.17 \times 10^{6}$ | $3.22 \times 10^{9}$ | 1484 | $1.76 \times 10^{6}$ | $2.71 \times 10^{8}$ | 154 | $2.12 \times 10^{9}$ | $1.78 \times 10^{8}$ | 1 | $2.12 \times 10^{9}$ | $1.78 \times 10^{8}$ |
| 6 | $1.90 \times 10^{6}$ | $2.59 \times 10^{9}$ | 1364 | $1.70 \times 10^{6}$ | $1.70 \times 10^{8}$ | 100 | $2.00 \times 10^{9}$ | $1.32 \times 10^{8}$ | 1 | $2.00 \times 10^{9}$ | $1.32 \times 10^{8}$ |
| 7 | $4.80 \times 10^{6}$ | $1.60 \times 10^{10}$ | 337 | $4.32 \times 10^{6}$ | $1.69 \times 10^{9}$ | 387 | $1.29 \times 10^{10}$ | $1.35 \times 10^{9}$ | 4 | $3.23 \times 10^{9}$ | $3.38 \times 10^{8}$ |
| 8 | $4.86 \times 10^{6}$ | $9.94 \times 10^{9}$ | 2045 | $4.23 \times 10^{6}$ | $7.28 \times 10^{8}$ | 172 | $1.02 \times 10^{10}$ | $7.47 \times 10^{8}$ | 3 | $3.40 \times 10^{9}$ | $2.49 \times 10^{8}$ |
| 9 | $1.70 \times 10^{6}$ | $2.55 \times 10^{9}$ | 1499 | $1.39 \times 10^{6}$ | $1.46 \times 10^{8}$ | 105 | $2.25 \times 10^{9}$ | $1.29 \times 10^{8}$ | 1 | $2.25 \times 10^{9}$ | $1.29 \times 10^{8}$ |
| 10 | $2.06 \times 10^{6}$ | $3.48 \times 10^{9}$ | 1692 | $1.77 \times 10^{6}$ | $1.92 \times 10^{8}$ | 108 | $2.75 \times 10^{9}$ | $1.51 \times 10^{8}$ | 1 | $2.75 \times 10^{9}$ | $1.51 \times 10^{8}$ |
| average | $2.62 \times 10^{6}$ | $5.11 \times 10^{9}$ | 1723 | $2.26 \times 10^{6}$ | $4.59 \times 10^{8}$ | 179 | $4.92 \times 10^{9}$ | $4.09 \times 10^{8}$ | | $2.59 \times 10^{9}$ | $2.07 \times 10^{8}$ |

n/a: not available

Table V sets forth the starting, ending and fold expansion numbers for total nucleated cells and $CD34^{+}$ cells post-expansion for 19 full scale ex vivo expansions.

TABLE V

| | CD34 | | | CD34 Purity | | TNC | | |
|---|---|---|---|---|---|---|---|---|
| Unit ID Product # | Starting # | Ending # | Fold Expansion | Starting % | Ending % | Starting # | Ending # | Fold Expansion |
| S001 | $2.29 \times 10^{6}$ | $2.69 \times 10^{8}$ | 117 | 88 | 4.9 | $2.60 \times 10^{6}$ | $5.47 \times 10^{9}$ | 2104 |
| S002 | $2.04 \times 10^{6}$ | $6.07 \times 10^{8}$ | 298 | 85 | 13 | $2.40 \times 10^{6}$ | $4.67 \times 10^{9}$ | 1944 |
| S003 | $1.76 \times 10^{6}$ | $2.71 \times 10^{8}$ | 154 | 81 | 8.4 | $2.17 \times 10^{6}$ | $3.22 \times 10^{9}$ | 1484 |
| S004 | $1.70 \times 10^{6}$ | $1.70 \times 10^{8}$ | 100 | 91 | 6.6 | $1.90 \times 10^{6}$ | $2.59 \times 10^{9}$ | 1364 |
| S005 | $4.32 \times 10^{6}$ | $1.69 \times 10^{9}$ | 387 | 90 | 10.4 | $4.80 \times 10^{6}$ | $1.60 \times 10^{10}$ | 3337 |
| S006 | $4.23 \times 10^{6}$ | $7.28 \times 10^{8}$ | 172 | 87 | 7.3 | $4.86 \times 10^{6}$ | $9.94 \times 10^{9}$ | 2045 |
| S007 | $1.39 \times 10^{6}$ | $1.46 \times 10^{8}$ | 105 | 82 | 5.7 | $1.70 \times 10^{6}$ | $2.55 \times 10^{9}$ | 1499 |
| S008 | $1.77 \times 10^{6}$ | $1.92 \times 10^{8}$ | 108 | 86 | 5.5 | $2.06 \times 10^{6}$ | $3.48 \times 10^{9}$ | 1692 |
| S009 | $2.70 \times 10^{6}$ | $4.74 \times 10^{8}$ | 176 | 88 | 8.8 | $3.07 \times 10^{6}$ | $5.42 \times 10^{9}$ | 1765 |
| S010 | $2.02 \times 10^{6}$ | $7.92 \times 10^{8}$ | 392 | 75 | 11.6 | $2.69 \times 10^{6}$ | $6.84 \times 10^{9}$ | 2543 |
| S011 | $1.64 \times 10^{6}$ | $4.25 \times 10^{8}$ | 259 | 82 | 15.2 | $2.00 \times 10^{6}$ | $2.79 \times 10^{9}$ | 1395 |
| S012 | $1.64 \times 10^{6}$ | $4.25 \times 10^{8}$ | 259 | 82 | 15.2 | $2.82 \times 10^{6}$ | $2.12 \times 10^{9}$ | 752 |
| S013 | $1.97 \times 10^{6}$ | $2.25 \times 10^{8}$ | 114 | 70 | 10.6 | $2.96 \times 10^{6}$ | $6.25 \times 10^{9}$ | 2111 |
| S014 | $2.28 \times 10^{6}$ | $6.49 \times 10^{8}$ | 285 | 77 | 10.4 | $2.60 \times 10^{6}$ | $2.15 \times 10^{9}$ | 827 |
| S015 | $1.74 \times 10^{6}$ | $1.42 \times 10^{8}$ | 82 | 67 | 6.63 | $2.50 \times 10^{6}$ | $2.97 \times 10^{9}$ | 1187 |
| S016 | $1.88 \times 10^{6}$ | $2.80 \times 10^{8}$ | 149 | 75 | 9.4 | $4.46 \times 10^{6}$ | $7.65 \times 10^{9}$ | 1715 |
| S017 | $3.75 \times 10^{6}$ | $1.04 \times 10^{9}$ | 276 | 84 | 13.6 | $6.90 \times 10^{6}$ | $4.07 \times 10^{9}$ | 590 |
| S018 | $6.28 \times 10^{6}$ | $2.91 \times 10^{8}$ | 46 | 91 | 7.14 | $2.34 \times 10^{6}$ | $2.18 \times 10^{9}$ | 932 |
| S019 | $1.78 \times 10^{6}$ | $2.29 \times 10^{8}$ | 129 | 76% | 10.52 | $2.16 \times 10^{6}$ | $2.00 \times 10^{9}$ | 926 |

These 19 expanded human cord blood stem cells were cryopreserved in one or more bags. Table VI sets forth total nucleated cell (TNC) and $CD34^+$ cell counts for each of the expanded human cord blood stem cell sample and cell viability prior to cryopreservation, and TNC and $CD34^+$ cell counts in each frozen bag.

TABLE VI

| Unit ID | Banked Cells | | | | | Final Viability |
|---|---|---|---|---|---|---|
| Product # | TNC | CD34 # | # Bags | TNC/Bag | CD34#/Bag | Trypan Blue |
| S001 | $4.20 \times 10^9$ | $2.06 \times 10^8$ | 2 | $2.10 \times 10^9$ | $1.03 \times 10^8$ | 67% |
| S002 | $2.90 \times 10^9$ | $3.77 \times 10^8$ | 1 | $2.90 \times 10^9$ | $3.77 \times 10^8$ | 62% |
| S003 | $2.12 \times 10^9$ | $1.78 \times 10^8$ | 1 | $2.12 \times 10^9$ | $1.78 \times 10^8$ | 69% |
| S004 | $2.00 \times 10^9$ | $1.32 \times 10^8$ | 1 | $2.00 \times 10^9$ | $1.32 \times 10^8$ | 55% |
| S005 | $1.29 \times 10^{10}$ | $1.35 \times 10^9$ | 4 | $3.23 \times 10^9$ | $3.38 \times 10^8$ | 67% |
| S006 | $1.02 \times 10^{10}$ | $7.47 \times 10^8$ | 3 | $3.40 \times 10^9$ | $2.49 \times 10^8$ | 57% |
| S007 | $2.25 \times 10^9$ | $1.29 \times 10^8$ | 1 | $2.25 \times 10^9$ | $1.29 \times 10^8$ | 70% |
| S008 | $2.75 \times 10^9$ | $1.51 \times 10^8$ | 1 | $2.75 \times 10^9$ | $1.51 \times 10^8$ | 79% |
| S009 | $6.30 \times 10^9$ | $5.51 \times 10^8$ | 2 | $3.15 \times 10^9$ | $2.76 \times 10^8$ | 59% |
| S010 | $4.93 \times 10^9$ | $5.70 \times 10^8$ | 2 | $2.47 \times 10^9$ | $2.85 \times 10^8$ | 66% |
| S011 | $1.82 \times 10^9$ | $2.77 \times 10^8$ | 1 | $1.82 \times 10^9$ | $2.77 \times 10^8$ | 57% |
| S012 | $1.70 \times 10^9$ | $1.81 \times 10^8$ | 1 | $1.70 \times 10^9$ | $1.81 \times 10^8$ | 59% |
| S013 | $5.14 \times 10^9$ | $5.34 \times 10^8$ | 2 | $2.57 \times 10^9$ | $2.67 \times 10^8$ | 68% |
| S014 | $1.50 \times 10^9$ | $9.91 \times 10^7$ | 1 | $1.50 \times 10^9$ | $9.91 \times 10^7$ | 68% |
| S015 | $1.94 \times 10^9$ | $1.83 \times 10^8$ | 1 | $1.94 \times 10^9$ | $1.83 \times 10^8$ | 62% |
| S016 | $4.08 \times 10^9$ | $5.53 \times 10^8$ | 2 | $2.04 \times 10^9$ | $2.76 \times 10^8$ | 54% |
| S017 | $3.90 \times 10^9$ | $2.78 \times 10^8$ | 1 | $3.90 \times 10^9$ | $2.78 \times 10^8$ | 65% |
| S018 | $1.23 \times 10^9$ | $1.29 \times 10^8$ | 1 | $1.23 \times 10^9$ | $1.29 \times 10^8$ | 68% |
| S019 | $2.19 \times 10^9$ | $2.23 \times 10^8$ | 1 | $2.19 \times 10^9$ | $2.23 \times 10^8$ | |

Further, an additional 12 samples of enriched $CD34^+$ cells were expanded with Delta1$^{ext\text{-}IgG}$, and showed an average 141-fold expansion (SEM 17) of $CD34^+$ cells, prior to cryopreservation.

9. EXAMPLE: TREATMENT OF PATIENTS WITH AML

9.1: Design

The below discussion describes the design of a clinical trial aimed at providing rapid restoration of hematopoietic function to patients suffering from acute myelogenous leukemia (AML) who have been treated with intensive induction chemotherapy by administering expanded human cord blood stem cells. This study will enroll in three cohorts at 10-15 patients per cohort, each with separate inclusion criteria based on disease status. Cohort A will enroll first for a total of 10 patients. If safety criteria are met, enrollment will occur in cohort B for a total of 15 patients; if safety criteria are again met, enrollment will occur in cohort C for a total of 15 patients.

Cohort A: Diagnosis of acute myeloid leukemia by WHO criteria, either relapsed or refractory. Acute promyelocytic leukemia [Acute promyelocytic leukemia with t(15;17)(q22; q12) and variants] will be eligible only after failure of a regimen containing arsenic trioxide. Patients in this cohort must have had an initial remission duration of <1 year and cannot have received any prior salvage chemotherapy.

Cohort B: Untreated AML patients with cytogenetic or molecular abnormalities associated with poor prognosis.

Cohort C: Untreated AML patients with intermediate prognosis.

In addition to disease criteria established above, all patients must meet inclusion criteria listed below:

1. The first three patients enrolled in each cohort must be less than 60 years old. Thereafter, patients aged 18 and 70 are eligible.
2. The first three patients enrolled in each cohort must have an ECOG performance status of 0-1. Thereafter, ECOG performance status of 0-2 is required.
3. The patients must have adequate renal and hepatic functions as indicated by the following laboratory values:
   a. Serum creatinine ≤1.0 mg/dL; if serum creatinine >1.0 mg/dl, then the estimated glomerular filtration rate (GFR) must be >60 mL/min/1.73 m2 as calculated by the Modification of Diet in Renal Disease equation where predicted GFR (ml/min/1.73 m2)=186×(Serum Creatinine)−1.154×(age in years)−0.023×(0.742 if patient is female)×(1.212 if patient is black).
   b. Serum total or direct bilirubin ≤1.5× upper limit of normal (ULN), aspartate transaminase (AST)/alanine transaminase (ALT) ≤2.5×ULN, alkaline phosphatase ≤2.5×ULN
4. Capable of understanding the investigational nature, potential risks and benefits of the study, and able to provide valid informed consent.
5. Female patients of childbearing potential must have a negative serum pregnancy test within 2 weeks prior to enrollment.
6. Male and female patients must be willing to use an effective contraceptive method during the study and for a minimum of 6 months after study treatment.
7. Panel reactive antibody (PRA) negative or with specific antibodies characterized and known to not be donor-directed against cord blood antigens.

The following individuals are excluded from this trial:

1. Allogeneic transplant recipients.
2. Current concomitant chemotherapy, radiation therapy, or immunotherapy other than as specified in the protocol.
3. Have any other severe concurrent disease, or have a history of serious organ dysfunction or disease involving the heart, kidney, liver (including symptomatic hepatitis, veno-occlusive disease), or other organ system dysfunction.
4. Patients with a systemic fungal, bacterial, viral, or other infection not controlled (defined as exhibiting ongoing signs/symptoms related to the infection and without improvement, despite appropriate antibiotics or other treatment).

5. Pregnant or lactating patients.
6. Any significant concurrent disease, illness, or psychiatric disorder that would compromise patient safety or compliance, interfere with consent, study participation, follow up, or interpretation of study results.

The expanded cord blood stem cells to be used for this trial will be selected from a bank of previously expanded cord blood progenitors that have been cryopreserved for future clinical use. Each individual progenitor cell product is derived from a single cord blood unit (donor) that is CD34 selected (and therefore T cell depleted), ex vivo expanded in the presence of Notch ligand and then cryopreserved as described above. The fresh cord blood units are obtained through a collaboration with the Cord Blood (CB) Program at the Puget Sound Blood Center/Northwest Tissue Center (PSBC/NTC). Selection of the expanded cord blood stem cells will be based on the following:

A. Panel Reactive Antibody (PRA) to be performed on all enrolled patients, and product selected based on the specificity of donor directed antibodies when present. PRA negative patients may receive any product that fits cell dose restrictions. HLA matching will not be considered outside of PRA+ patients.
1. For patients eligible for a second dose of expanded cell product: PRAs will be repeated prior to selection of cord blood progenitor cell products.

B. Cell Doses:
1. Infused TNC/kg cell dose will not exceed $1\times10^8$ TNC/kg recipient body weight.
2. No upper limit will be placed on the $CD34^+$ cells/kg infused.
3. All expanded products are evaluated by immunophenotyping for the presence of $CD3^+$ cells prior to freezing. While there has been no convincing evidence of a $CD3^+$ cell population, if a product has evidence of a T cell ($CD3^+$) population, this product will not be used unless the dose of $CD3^+$ cells is $<5\times10^5$ $CD3^+$ cells/kg (recipient weight).

C. Repeat Infusions of Expanded Progenitors: Patients with severe infusional toxicities are not eligible for repeat infusions.

Figure 14:
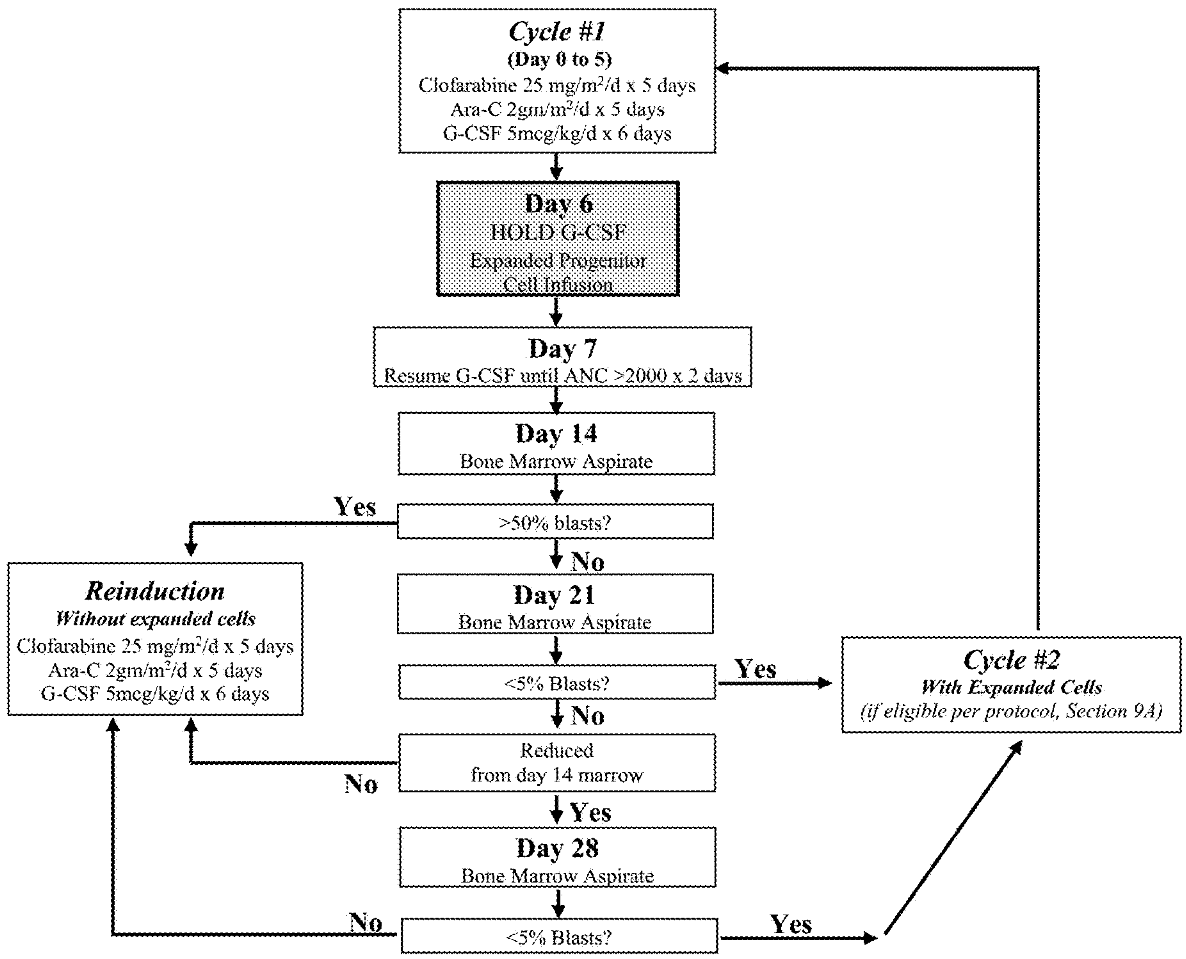
FIG. 14 is a flow chart setting forth a plan for induction therapy for patients with AML.

FIG. 14 depicts the plan for treating enrolled patients suffering from AML.

Patients will receive one cycle of induction chemotherapy followed by infusion of expanded cord blood progenitors, with the possibility of a second cycle with infusion of expanded cell product beginning on day 21 to 28 post chemotherapy, provided the following conditions are met:

1. The patient does not have residual leukemia, defined as <5% marrow blasts by morphology.
2. The patient has not experienced any extramedullary grade 3-4 toxicities.
3. The neutrophil count has recovered to 500/μl (on or off G-CSF).
4. The patient has no uncontrolled infections.
5. The patient has not had a history of severe infusional toxicities with the first expanded product infusion.

Plan for Consolidation Cycles: Only patients who achieve a remission (defined as <5% blasts by morphology) after reinduction (without expanded cells) or cycle 2 (with expanded cells) as per FIG. 14 will be eligible to receive additional consolidation therapy. Eligible patients will receive a maximum of two cycles of consolidation therapy. Whether or not a patient receives consolidation therapy will depend on whether the patient will be undergoing additional therapy such as a stem cell transplant. Consolidation will be offered without the use of expanded cord blood progenitor cells.

D. Induction Therapy (See Also FIG. 14):
1. All patients will receive an initial induction cycle followed by infusion of expanded cord blood progenitors ("Cycle 1" in diagram, FIG. 14. Patients will receive a second infusion of expanded cord blood progenitors with induction cycle 2 only if eligible, as outlined in "Eligibility for repeat expanded cell infusion with induction cycle 2" in FIG. 14. All other patients will undergo reinduction therapy without infusion of expanded cord blood progenitors, as per FIG. 14.
2. The dosing of clofarabine, Ara-C and G-CSF is the same for induction cycles 1 and 2, regardless of whether the patient is eligible for a second infusion of expanded progenitor cells.
3. G-CSF: 5 μg/kg subcutaneously (SQ), rounded up to nearest vial size, beginning 24 hours prior to chemotherapy and continued daily through day 5. Infusion of the expanded cell product will occur on day 6 and G-CSF will be held that day. G-CSF will be resumed on day 7 and continued daily until ANC >2000 for two consecutive days.
4. Clofarabine: A dose of 25 mg/m2 will be administered as a 1 hour intravenous infusion once daily for 5 days.
5. Ara-C: A dose of 2 gm/m2 will be administered as a 2-hour intravenous infusion once daily for 5 days, starting 4 hours after the start of the clofarabine infusion.
6. Infusion of expanded, cryopreserved cord blood stem cells of the invention:
a. Dosage and selection of expanded product: Infused total nuclear cell count(TNC)/kg cell dose will not exceed $1\times10^8$ TNC/kg recipient body weight. CD34 cell dose: No upper limit will be placed on the CD34 cells/kg infused. All expanded products are evaluated by immunophenotyping for the presence of $CD3^+$ cells prior to freezing. While there has been no convincing evidence of a $CD3^+$ cell population, if a product has evidence of a T cell ($CD3^+$) population, this product will not be used unless the dose of $CD3^+$ cells is $<5\times10^5$ CD3 cells/kg (recipient weight).

The infusion rate of the expanded cord blood stem cells of the invention is infuse at a rate of 3-5 ml/min for the first 4 minutes. If tolerated, the rate is increased to "wide open". No medications or fluids should be given piggyback through the catheter that is being used for the expanded cell infusion.

TABLE VII

| Induction Therapy | | |
|---|---|---|
| Day | Cycle 1 and 2 (with expanded cells) | "Reinduction" (without expanded cells) |
| 0 | G-CSF 5 μg/kg SQ | G-CSF 5 μg/kg SQ |
| 1-5 | Clofarabine 25 mg/$m^2$ IV over 1 hour<br>Ara-C 2 gm/$m^2$ IV over 2 hours<br>G-CSF 5 μg/kg SQ | Clofarabine 25 mg/$m^2$ IV over 1 hour<br>Ara-C 2 gm/$m^2$ IV over 2 hours<br>G-CSF 5 μg/kg SQ |
| 6 | Hold GCSF<br>Infusion of expanded cord blood progenitors | Continue GCSF until ANC >2000 for two consecutive days |
| 7 | Resume GCSF and continue until ANC >2000 for two consecutive days | |

E. Consolidation Therapy

1. Patients in remission (defined as <5% marrow blasts by morphology) will be eligible to receive up to two cycles of consolidation, depending on whether the patient will be going on to receive additional therapy such as a stem cell transplant. Patients with refractory disease after cycle 2 with expanded cell infusion or reinduction without expanded cell infusion will be removed from the study.
2. G-CSF: 5 μg/kg subcutaneously (SQ), rounded up to nearest vial size, beginning 24 hours prior to chemotherapy and continued daily until ANC >2000 for two consecutive days.
3. Clofarabine: A dose of 20 mg/m2 will be administered as a 1 hour intravenous infusion once daily for 5 days.
4. Ara-C: 1 gm/m2 as a two hour intravenous infusion once daily for five days, starting four hours after the start of the clofarabine infusion. Patients in remission (defined as <5% marrow blasts by morphology) will be eligible to receive up to two cycles of consolidation, depending on whether the patient will be going on to receive additional therapy such as a stem cell transplant. Patients with refractory disease after cycle 2 with expanded cell infusion or reinduction without expanded cell infusion will be removed from the study.

TABLE VIII

| Consolidation Therapy: | |
|---|---|
| Day 0 | G-CSF 5 μg/kg SQ |
| Day 1-5 | Clofarabine 20 mg/$m^2$ IV over 1 hour<br>Ara-C 1 gm/$m^2$ IV over 2 hours<br>G-CSF 5 μg/kg SQ |
| Day 6 | Continue G-CSF until ANC >2000 for two consecutive days |

Evaluation Guidelines:

A. Pre-Treatment Evaluation

1. Complete physical examination.
2. Medical history: Detailed documentation of disease and treatment history with outcomes.
3. ECOG performance status
4. 12 lead EKG
5. Hematology: CBC with differential and platelet count and peripheral blood smear.
6. Serum chemistries: Electrolytes (sodium, potassium, chloride, and bicarbonate), blood urea nitrogen (BUN), creatinine, glucose, and liver function tests (aspartate aminotransferase (AST) and/or alanine aminotransferase (ALT), alkaline phosphatase (ALP), total bilirubin, lactate dehydrogenase (LDH).
7. Panel Reactive Antibody (PRA).
8. Adverse event assessment from time of first dose of G-CSF.
9. Initial standard of care diagnostic bone marrow reports, including hematopathology, cytogenetics/FISH, and flow cytometry.
10. To subsequently determine post transplant chimerism, heparinized peripheral blood from the patient will be obtained and chimerism analysis by DNA analysis will be performed.

B. Evaluation to be Completed the Morning of Expanded Progenitor Infusion:

1. Physical exam and review of systems done by provider
2. Weight by nursing
3. CBC [CBD] (includes HCT, HGB, WBC, RBC, indices, platelets, DIFF/SMEAR EVAL)
4. [SRFM] and [SHFL] (HSCT Renal function panel with magnesium and HSCT Hepatic function panel with LD; SRFM includes NA, K, CL, CO2, GLU, BUN, CRE, CA, P, ALB, MG and SHFL includes ALT, AST, ALK, BILIT/D, TP, ALB, LD)
5. Complete urinalysis C. Evaluation During Infusion of Ex Vivo Expanded Cord Blood Progenitors 1. RN must be in attendance during infusion.
2. MD or PA must be available on the inpatient unit.
3. If any changes in cardiac status, notify physician and obtain ECG.
4. Obtain and record vital signs including temperature, BP, HR, Respirations, and O2 saturation at the following time points:

TABLE IX

| |
|---|
| Pre-infusion |
| 15 minutes after the start of infusion |
| 30 minutes after the start of infusion |
| 45 minutes after the start of infusion |
| 1 hour after the start of infusion |
| 2 hours after the start of infusion |
| 4 hours after the start of infusion |
| 24 hours after the start of infusion |

5. Dipstick for HGB/protein every voided urine for 24 hours after infusion of expanded cells. Record HGB and Protein.

D. Evaluation 24 Hours Post Infusion of Ex Vivo Expanded Cord Blood Progenitors

1. CBC [CBD] (includes HCT, HGB, WBC, RBC, indices, platelets, DIFF/SMEAR EVAL)
2. [SRFM] and [SHFL] (HSCT Renal function panel with magnesium and HSCT Hepatic function panel with LD; SRFM includes NA, K, CL, CO2, GLU, BUN, CRE, CA, P, ALB, MG and SHFL includes ALT, AST, ALK, BILIT/D, TP, ALB, LD
3. Complete Urinalysis E. Post-Treatment Evaluation 1. Engraftment studies: Contribution to hematopoietic recovery from the expanded cell product will be assessed from sorted peripheral blood (cell sorted for $CD3^+$, $CD33^+$, $CD14^+$, and $CD56^+$ cell fractions) on day 7, 14, 21, 28 and 56 following the infusion of expanded cells (or days 13, 20, 27, 34 and 62 of the chemotherapy cycle). If the patient is 100% host at the day 14 time point, all subsequent analyses will not be performed. However, should there be persistent evidence of engraftment derived from the expanded cell infusion at day 56, donor-host chimerism studies will be performed every 2 to 4 weeks as necessary to follow donor-host kinetics of engraftment. The percentages of donor-host chimerism will be evaluated by polymerase chain reaction (PCR)-based amplification of variable-number tandem repeat (VNTR) sequences unique to donors and hosts and quantified by phosphoimaging analyses.
2. Alloimmunization: Repeat PRA to evaluate for the development of anti-HLA antibodies will be performed upon count recovery or prior to the next cycle of chemotherapy.
3. Hematology: CBC with differential and platelet count and peripheral blood smear daily while in hospital and/or until hematopoietic recovery, then at each outpatient clinic visit during the induction, re-induction, and consolidation cycles.

4. Serum chemistries: Electrolytes (sodium, potassium, chloride, and bicarbonate), BUN, creatinine, glucose, and liver function tests (AST, ALT, ALP, total bilirubin, LDH) twice weekly while in hospital, then weekly during the induction, re-induction, and consolidation cycles.
5. Bone marrow evaluations: Post induction cycles or reinduction: Marrow evaluations will be performed for hematopathology, cytogenetics/FISH, flow cytometry and whole marrow chimerism evaluations on day 8 and 15 (if necessary) following the infusion of expanded cells (or days 14 and 21 (if necessary) of the chemotherapy cycle). Additional marrows will be done as clinically indicated. If there is no count recovery by day 42 post chemotherapy, a bone marrow evaluation will be performed for hematopathology, cytogenetics/FISH, flow cytometry and whole marrow chimerism to rule out aplasia induced by a graft-versus-host phenomenon from the expanded cell population versus aplasia due to persistent disease or chemotherapy induced aplasia. Post consolidation cycles (if received): Marrow evaluations will be performed for hematopathology, cytogenetics/FISH, and flow cytometry evaluations on day 21 and upon hematopoietic recovery (if necessary).
6. Host and Donor Immunologic Interaction Studies
a. Prior to the start of chemotherapy (and after consent obtained): 40 ml of peripheral blood will be collected in green top tubes to generate EBV transformed LCL lines from the patient for research studies evaluating donor/host immunologic reactions.
b. Post infusion of expanded cells on up to five occasions, 30 to 40 ml of peripheral blood may be collected in green top tubes to assay for immune mediated responses occurring between the host and donors. Investigator discretion on the timing of samples is provided to allow investigators to obtain samples once individual hematopoietic recovery has occurred and to avoid obtaining samples if patients have been placed on steroids for treatment of a GVHD (steroids interfere with the studies).
c. Samples should be drawn on Monday through Friday only.
7. Adverse Events: Adverse events will be evaluated and recorded.
8. GVHD: All patients will be monitored for development of potential transfusion related GVHD. If signs or symptoms of acute GVHD occur, patients will be assessed. Treatment of GVHD will be per institutional guidelines, but only if biopsy proven GVHD is present.
9. Follow-up through 6 months:
a. Complete blood count, renal function, and liver function tests obtained for clinical reasons for a period of 6 months, as needed to define toxicity or duration of response.
b. Disease free and overall survival data will be assessed by contacting the referring MD or the patient every three to six months for the first two years, then annually for 3 years.

F. Supportive Care Guidelines
1. Blood Products: All blood products are to be irradiated and leukocyte-reduced. Also, CMV-negative patients will receive blood products as outlined by institutional standard practice guidelines. Transfusions will be administered for symptomatic anemia, or below standard threshold levels appropriate to the clinical setting.
2. Infection Prophylaxis: Prophylactic oral acyclovir and levofloxacin will be used during the period of neutropenia. To the extent possible, use of nephrotoxic (e.g., vancomycin, amphotericin B, etc.) and hepatotoxic (e.g., voriconazole, cyclosporine, etc.) agents is to be avoided during clofarabine administration for all treatment cycles.
3. Treatment of Fever and Neutropenia: Standard diagnostic testing will be performed as per institutional guidelines, and empiric antibiotic coverage will be utilized. Specific antibiotics will be used for positive cultures.
4. Colony Stimulating Factors: G-CSF will be utilized as per protocol during induction and consolidation chemotherapy as outlined above. Erythropoietic stimulating agents will not be utilized during induction or consolidation.
5. Concomitant Therapy: No concomitant cytotoxic therapy or investigational therapy is allowed during the study with the exception of intrathecal therapy for leukemic meningitis. Intrathecal therapy must not be given during or within 24 hours of any 5 day Clofarabine/Cytarabine treatment period.

G. Duration of Therapy: Patients Will Receive One to Four Cycles of Study Treatment. Expanded Cord Blood Progenitors Will be Used with Induction Cycle #1 and Cycle #2 Unless:
1. There is a history of severe infusional toxicity associated with the expanded cell product, in which case the patient will not be eligible to receive additional doses of the expanded cell product.
2. There is evidence of disease progression.
3. General or specific changes in the patient's condition render the patient unacceptable for further treatment per the investigator's judgment.
4. The patient chooses to withdraw from the study.
5. The patient becomes pregnant or fails to use adequate birth control if able to conceive.
6. The patient is not able to comply with the protocol requirement.

9.2: Implementation

Frequent infections are a common complication of induction chemotherapy and salvage regimens used in the treatment of AML, and, in fact, are a leading cause of treatment failure. Use of clofarabine and high dose ara-c, in combination with granulocyte colony stimulating factor (G-CSF) has been studied in a phase I/II trial in the treatment of AML (Becker et al., 2008, Blood 112 ASH Annual Meeting Abstracts) (such a chemotherapy cycle is referred to herein as "GCLAC"). Clofarabine has potent anti-leukemic activity, and clofarabine and high dose ara-c, in combination with G-CSF appears to be at least as effective as the more commonly used combination of idarubicin and ara-C. However, clofarabine is also profoundly immunosuppressive and, in conjunction with ara-C, is highly myelosuppressive, with periods of prolonged neutropenia post-GCLAC of greater than three weeks. The combined immune- and myelosuppressive effects of clofarabine and the delayed hematopoietic recovery results in frequent infections and prevents dose intensive therapy. In a cohort of patients treated at our center, >50% of patients experienced infectious complications post GCLAC, and approximately 13% of patients experienced grade 4 infections (Becker et al., 2008, Blood 112 ASH Annual Meeting Abstracts). Importantly, infusion of expanded human cord blood stem and progenitor cells can help overcome both of these challenges. Additionally, the immunosuppression caused by the clofarabine-based regimen increases the likelihood that the expanded human cord blood stem cell sample may temporarily engraft and provide clinical benefit.

To date, nine adult patients with relapsed (n=7) or primary refractory (n=2) AML have been enrolled according to the criteria set out in Section 9.1, supra. The age range was 40 to 55 years. Patients received their first cycle of chemotherapy: clofarabine 25 mg/m$^2$/day for 5 days, ara-C 2 gm/m$^2$/day for 5 days, G-CSF 5 mcg/kg/day for 6 days ("GCLAC"), followed approximately 24 hours after completion of GCLAC by infusion of an expanded human cord blood stem cell sample without regard to matching the HLA-type of the expanded human cord blood stem cell sample to the HLA-type of the patient. The expanded human cord blood stem cell sample was produced according to the method set forth in Example 8, supra. If response to GCLAC was demonstrated by achievement of morphologic remission (based on bone marrow aspirate), patients were eligible to receive a second cycle of GCLAC and a second expanded human cord blood stem cell sample.

A total of twelve expanded human cord blood stem cell samples were infused into the nine patients. Of the nine patients treated, four patients were refractory to GCLAC therapy, and therefore were non-evaluable for neutrophil recovery. Three of the five patients who achieved remission received a second cycle of GCLAC and a second expanded human cord blood stem cell sample. Two out of the five patients who achieved remission after the first cycle of GCLAC and expanded cord blood stem cell sample, were given a hematopoietic stem cell transplant of a type determined by the treating physician. For these remaining 5 patients (2 male, 3 female), the average time to achieve an absolute neutrophil count (ANC) >500 per μl was 19 days (see FIG. 15), comparing favorably to 21 days in a historical cohort of patients receiving GCLAC only without expanded cells. Importantly, in the nine patients there have been no safety issues with the infusion of the expanded human cord blood stem cell samples, or serious adverse events attributed to the expanded human cord blood stem cell samples to date.

Only 2 of the 9 enrolled patients have experienced clinically significant infections (e.g., bacteremia, fungal infections, pneumonia) compared to 17 out of 28 patients in the comparison cohort. Finally, three out of three patients who received a second cycle of GCLAC with a second expanded human cord blood stem cell sample were found to have transient donor contribution (as measured by peripheral blood cell sorted DNA chimerism studies) to myeloid recovery one week after infusion of the cells, ranging from 85 to 100% donor in the CD33/CD14 cell lineages. In these three patients, the cells were also able to home to the marrow as evidenced by transient myeloid engraftment of donor origin in the marrows of recipients (day 7 after infusion of the cells) ranging from 3 to 15% (FIG. 16).

10. EXAMPLE: TREATMENT OF PATIENTS WITH HODGKIN'S LYMPHOMA, NON-HODGKIN'S LYMPHOMA AND MULTIPLE MYELOMA

The below discussion describes the design of a clinical trial aimed at providing rapid restoration of hematopoietic function to patients suffering from Hodgkin's lymphoma, non-Hodgkin's lymphoma and multiple myeloma who have been treated with intensive chemotherapy and/or radiation therapy in preparation for autologous transplant by administering expanded human cord blood stem cells. This study will enroll patients will the following characteristics:

Patients with Hodgkin's or non-Hodgkin's lymphoma and multiple myeloma are eligible. Histologically confirmed Hodgkin's or non-Hodgkin's lymphoma who have failed at least 1 prior therapy. Histologically confirmed, symptomatic multiple myeloma who have received at least 1 line of conventional chemotherapy. Failure to collect an optimum number of PBSC after at least 1 attempt at mobilization. For purposes of this trial this shall be defined as <3×10$^6$ CD34$^+$ cells/kg, however, the first 3 patients enrolled will have 1 to 2×10$^6$ CD34$^+$ cells/kg. Patients may have more than 1 attempt at mobilization as long as the total dose is <3×10$^6$ CD34$^+$ cells/kg. Patients must have at least 1×10$^6$ CD34$^+$ cells/kg PBSC product available to be eligible for this trial.

The patients will be between the ages of 18 and 70 and will have 0-2 ECOG performance status results. Further, the patients will have adequate renal and hepatic functions as indicated by the following laboratory values: Serum creatinine mg/dL; if serum creatinine ≥2.0 mg/dl, then the estimated glomerular filtration rate (GFR) must be >60 mL/min/1.73 m2 as calculated by the Modification of Diet in Renal Disease equation where predicted GFR (ml/min/1.73 m2)=186×(Serum Creatinine)−1.154×(age in years)−0.023×(0.742 if patient is female)×(1.212 if patient is black). Serum total or direct bilirubin ≤1.5× upper limit of normal (ULN), aspartate transaminase (AST)/alanine transaminase (ALT) ≤2.5×ULN, alkaline phosphatase ≤2.5×ULN. The patients will be capable of understanding the investigational nature, potential risks and benefits of the study, and able to provide valid informed consent. Female patients of childbearing potential must have a negative serum pregnancy test within 2 weeks prior to enrollment. Male and female patients must be willing to use an effective contraceptive method during the study and for a minimum of 6 months after study treatment. Panel reactive antibody (PRA) negative or with specific antibodies characterized for product selection will be performed (to avoid donor-directed antibodies against the potential cord blood product). All eligible patients will have a preliminary donor search conducted prior to the initiation of therapy to identify potential donors (related or unrelated and including suitable cord blood units) in the event of graft failure.

The following types of patients are excluded: Allogeneic transplant recipients, current concomitant chemotherapy, radiation therapy, or immunotherapy other than as specified in the protocol, use of other investigational agents within 30 days or any anticancer therapy within 2 weeks before study entry. Other exclusion factors are any other severe concurrent disease, or have a history of serious organ dysfunction or disease involving the heart, kidney, liver (including symptomatic hepatitis, veno-occlusive disease), or other organ system dysfunction, history of HIV infection, patients with a systemic fungal, bacterial, viral, or other infection not controlled (defined as exhibiting ongoing signs/symptoms related to the infection and without improvement, despite appropriate antibiotics or other treatment), pregnant or lactating patients, patients having any significant concurrent disease, illness, or psychiatric disorder that would compromise patient safety or compliance, interfere with consent, study participation, follow up, or interpretation of study results, having central nervous system involvement with malignancy, and patients having no potential donor available (based on preliminary search) for allogeneic transplant in the event of graft failure.

The expanded cord blood progenitors to be used for this trial will be selected from a bank of previously expanded cord blood progenitors that have been cryopreserved for future clinical use. Each individual progenitor cell product is derived from a single cord blood unit (donor) that is CD34 selected (and therefore T cell depleted), ex vivo expanded in the presence of Notch ligand (as described above in Section 8) and then cryopreserved. The fresh cord blood units are obtained through a collaboration with the Cord Blood (CB) Program at the Puget Sound Blood Center/Northwest Tissue Center (PSBC/NTC).

Selection of the expanded progenitors will be based on the following:

A. Panel Reactive Antibody (PRA) to be performed on all enrolled patients, and product selected based on the specificity of donor directed antibodies when present. PRA negative patients may receive any product that fits cell dose restrictions. HLA matching will not be considered outside of PRA+ patients.

B. Cell Doses:

1. TNC/kg pre-cryopreservation cell dose will not exceed $1.2\times10^9$ TNC/kg recipient body weight, to account for an anticipated approximate 20% cell loss upon thaw with the goal of maintaining cell doses at $\leq1\times10^9$ TNC/kg.
2. CD34 cell dose: No upper limit will be placed on the CD34 cells/kg infused.
3. All expanded products are evaluated by immunophenotyping for the presence of $CD3^+$ cells prior to freezing. While there has been no convincing evidence of a $CD3^+$ cell population, if a product has evidence of a T cell ($CD3^+$) population, this product will not be used unless the dose of $CD3^+$ cells is $<5\times10^5$ $CD3^+$ cells/kg (recipient weight).

The patient will be referred for treatment of lymphoma or multiple myeloma. The patient will be completely evaluated. The protocol will be discussed thoroughly with the patient and family, including requirement for data collection and release of medical records, and all known significant risks to the patient will be described. The procedure and alternative forms of therapy will be presented as objectively as possible and the risks and hazards of the procedure explained to the patient. Informed consent will be obtained using forms approved by the Institutional Review Board of the Fred Hutchinson Cancer Research Center. A summary of the conference should be dictated for the medical record detailing what was covered.

The patients will be treated according to the following plan:

Peripheral Blood Stem Cell Collection: Peripheral blood stem cells (PBSC) will be collected by serial leukaphereses by any know mobilization method). At least $1.0\times10^6$ $CD34^+$ cells/kg must be available for transplant.

B. High dose conditioning regimens:

Multiple Myeloma Patients

Standard conditioning using melphalan 200 mg/m2 will be utilized for all patients.

TABLE X

| | Day | | | | | | |
|---|---|---|---|---|---|---|---|
| Treatment | −5 | −4 | −3 | −2 | −1 | 0 | +1 |
| Allopurinol (300 mg) | | X | X | X | X | | |
| Bactrim (1 DS tab BID) | X | X | X | X | | | |
| Melphalan 200 mg/m$^2$ | | | | X | | | |
| Infusion: autologous PBSC + expanded cord blood | | | | | | X | |
| G-CSF 5 mcg/kg/d until ANC >2000 for two consecutive days | | | | | | | X |

Lymphoma Patients

TBI-based regimen for patients who have not received prior dose limiting TBI (>20 Gy to any critical normal organ (e.g. lung, liver, spinal cord).

TABLE XI

| | Day | | | | | | | | | | | | | |
|---|---|---|---|---|---|---|---|---|---|---|---|---|---|---|
| Treatment | −11 | −10 | −9 | −8 | −7 | −6 | −5 | −4 | −3 | −2 | −1 | 0 | +1 | +2 |
| Palifermin 60 mcg/kg/day | X | X | X | | | | | | | | | X | X | X |
| TBI 1.5 Gy BID (total dose 12 Gy) | | | | X | X | X | X | | | | | | | |
| Etoposide 60 mg/kg IV | | | | | | | | X | | | | | | |
| Rest | | | | | | | | | X | | | | | |
| Cyclophosphamide 100 mg/kg IV | | | | | | | | | | X | | | | |
| Rest | | | | | | | | | | | X | | | |
| Infusion: autologous PBSC + expanded cord blood | | | | | | | | | | | | X | | |
| G-CSF 5 mcg/kg/d until ANC >2000 for two consecutive days | | | | | | | | | | | | | X | X |

Cyclophosphamide Dosage: Cyclophosphamide will be administered at a dose of 100 mg/kg/day IV on day 2 of conditioning. Preparation, administration and monitoring will be according to standard methods. Dosing in patients >100% of IBW will be per standard practice. MESNA will be given for bladder prophylaxis according to standard practice. Continuous bladder irrigation is an alternative for bladder prophylaxis at the attending physician's discretion. Hydration and monitoring for toxicities will be according to standard practice.

Total Body Irradiation: Total body irradiation (TBI), 1.5 Gy BID×4 days (for a total dose of 12 Gy) is delivered via a linear accelerator at a dose rate of 8 Gy/min.

IV Hydration and Antiemetic Therapy: IV hydration should be given at 2 liters/m2/24 hrs. Scheduled doses of antiemetics per standard practice.

BEAM conditioning regimen: Patients ineligible for a TBI based regimen will receive high dose therapy with a BEAM conditioning regimen.

TABLE XII

| | Day | | | | | | | | |
|---|---|---|---|---|---|---|---|---|---|
| Treatment | −7 | −6 | −5 | −4 | −3 | −2 | −1 | 0 | +1 |
| BCNU 300 mg/m2 IV x 1 d | X | | | | | | | | |
| Etoposide 100 mg/m2 IV BID x 4 d | | X | X | X | X | | | | |
| Ara-C 100 mg/m2 IV BID x 4 d | | X | X | X | X | | | | |
| Melphalan 140 mg/m2 x 1 d | | | | | | X | | | |
| Rest | | | | | | | X | | |
| Infusion: Autologous PBSC + expanded cord blood | | | | | | | | X | |
| G-CSF 5 mcg/kg/d until ANC >2000 for two consecutive days | | | | | | | | | X |

BCNU (Carmustine):

Dosage: Carmustine 300 mg/m2 IV×1 will be infused over 3 hours on day −7 of conditioning. Carmustine should not be infused with solutions or tubing containing or previously containing bicarbonate solution.

Chemistry: Carmustine, a nitrosourea derivative, is generally considered to be an alkylating agent. The drug is available as a white lyophilized powder at 4° C. It is slightly soluble in water, freely soluble in alcohol, and highly soluble in lipids.

Administration: Carmustine is available as a sterile powder as 100 mg vials. The drug is reconstituted by dissolving the contents of the 100 mg vial in 3 ml of sterile dehydrated (absolute) alcohol, followed by the addition of 27 ml of sterile water for injection. The resultant solution contains 3.3 ml of carmustine per ml of 10% alcohol. This solution may be further diluted with 0.9% sodium chloride or 5% dextrose injection to a final concentration of 0.2 mg/ml in glass containers. Only glass containers are recommended to be used for administration of this drug. Carmustine is rapidly degraded in aqueous solutions at a pH greater than 6.

After IV administration, carmustine is rapidly cleared from the plasma with no intact drug detectable after 15 minutes. Carmustine is rapidly metabolized, although the mechanism is not fully elucidated. Excretion of the metabolites occurs mainly through the urine and some metabolites are known to be active.

Maintenance hydration: Normal saline plus 20 mEq KCL is to be started at 2 liters/m2/day pre-Carmustine and continued until 24 hours after the last dose of Melphalan.

Pharmacokinetics: Because of their high lipid solubility, carmustine and/or its metabolites readily cross the blood-brain barrier. Substantial CSF concentrations occur almost immediately after administration of carmustine, and CSF concentrations of radiolabeled-BCNU have been variously reported to range from 15-70% of concurrent plasma concentrations. Carmustine metabolites are distributed into milk, but in concentrations less than those in maternal plasma.

Etoposide (VP-16, Vepesid):

Dosage: Etoposide 100 mg/m2 IV BID will be administered in 500-1000 cc normal saline over 2 hours on days −6, −5, −4, and −3 of conditioning for a total dose of 800 mg/m2.

Chemistry and mechanism of action: Etoposide is a semi-synthetic podophyllotoxin. The epipodophyllotoxins exert phase-specific spindle poison activity with metaphase arrest and, in contrast to the vinca alkaloids, have an additional activity of inhibiting cells from entering mitosis. Suppression of tritiated thymidine, uridine, and leucine incorporation in human cells in tissue culture suggests effects against DNA, RNA, and protein synthesis.

Storage and stability: Unopened vials of VP-16 are stable for 24 months at room temperature. Vials diluted as recommended to a concentration of 0.2 or 0.4 mg/mL are stable for 96 and 24 hours, respectively, at room temperature (25° C.) under normal room fluorescent light in both glass and plastic containers. Undiluted VP-16 in plastic syringes has been reported to be stable for up to 5 days.

Availability, reconstitution and administration: Etoposide is commercially available in 100 mg/5 ml, 150 mg/7.5 ml, 500 mg/25 ml or 1000 mg/50 ml sterile multiple dose vials. VP-16 should be diluted prior to use with either 5% Dextrose Injection, USP, or 0.9% Sodium Chloride Injection, USP, to give a final concentration of 0.2 or 0.4 mg/ml. Precipitation may occur at solutions above 0.4 mg/ml concentration. It is recommended that VP-16 solution be administered IV over 2 hours. However, a longer duration of administration may be used when infusing large volumes of fluid. VP-16 should not be infused rapidly. To avoid large volumes, VP-16 can be given undiluted, with special equipment and precautions. If VP-16 is administered undiluted, a 4-way stopcock and tubing made with "chemo resistant" (not containing acrylic or ABS components) plastic must be used. Undiluted VP-16 cannot be infused without concurrent IV solution infusing through the Hickman catheter. Infusion of undiluted VP-16 alone will cause Hickman catheter occlusion.

Supportive Care: Appropriate anti-emetics and sedatives should be given before the infusion begins. Before and 2 hours into the infusion, the patient is to receive 25 mg of diphenhydramine, and 100 mg of hydrocortisone to prevent allergic reactions. Normal saline plus 20 mEq KCL is to be continued at 2 liters/m2/day. If necessary, diuretics may be given. Since in rare cases metabolic acidosis has been observed after high dose VP-16, additional $NaHCO_3$ may be added to hydration, though not infused while VP-16 is infusing.

Cytarabine(Ara-C):

Dosage: Cytarabine 100 mg/m2 IV BID will be infused over 3 hours on days −6, −5, −4 and −3 of conditioning.

Chemistry: Cytarabine is a synthetic pyrimidine nucleoside and pyrimidine antagonist anti-metabolite.

Availability and administration: Cytarabine is available in a reconstituted form in solutions containing 20, 50 and 100 mg of cytarabine per ml. These solutions have been reconstituted from a sterile powder with bacteriostatic water containing 0.945% benzyl alcohol for injection. The manufacturers state that the reconstituted solutions with water for injection may be diluted with 0.9% sodium chloride or 5% dextrose. The diluted solutions containing 0.5 mg of cytarabine per mL are stable for at least 8 days at room temperature.

Pharmacokinetics: Cytarabine is not effective when administered orally.

Continuous IV infusions produce relatively constant plasma concentrations of the drug in 8-24 hours. Cytarabine is rapidly and widely distributed into tissues and fluids, including liver, plasma, and peripheral granulocytes and crosses the blood-brain barrier to a limited extent. The drug apparently crosses the placenta. It is not known if cytarabine is distributed in milk. After rapid IV injection, plasma drug concentrations appear to decline in a biphasic manner with a half-life of about 10 minutes in the initial phase and about 1-3 hours in the terminal phase. Cytarabine is rapidly and extensively metabolized mainly in the liver but also in the kidneys, gastrointestinal mucosa, granulocytes, and to a lesser extent in other tissues by the enzyme cytidine deaminase, producing the inactive metabolite 1-B-d-arabinofuranosyluracil (ara-U). Cytarabine and ara-U are excreted in urine. After rapid IV, IM, SQ, or IT injection or continuous IV infusion of cytarabine, about 70-80% of the dose is excreted in the urine within 24 hours.

Melphalan:

Dosage: Melphalan will be administered at a dose of 140 mg/m2 IV×1 infused over 30 minutes on day −2 of conditioning.

Chemistry: Melphalan (L-phenylalanine mustard) is a typical alkylating agent that can be given intravenously or orally.

Administration: Melphalan is available in 50 mg vials and when reconstituted with 10 ml sterile water results in a concentration of 5 mg/ml. The reconstituted melphalan is diluted in 250 cc normal saline to a concentration not greater than 0.5 mg/ml. Melphalan is administered over 15 minutes, not to exceed 60 minutes.

Pharmacokinetics: Plasma melphalan levels are highly variable after oral dosing, both with respect to the time of the first appearance of melphalan in plasma (range: 0 to 336 minutes) and to the peak plasma concentration (range: 0.166 to 3.741 mg/mL) achieved. These results may be due to incomplete intestinal absorption, a variable "first pass" hepatic metabolism, or to rapid hydrolysis.

C. Cell Infusion:

1. Autologous PBSC will be thawed and infused on the morning of day 0.
2. Expanded cell infusion: Expanded cells will be thawed and infused as per standard guidelines and infused approximately 4 hours after infusion of the autologous stem cell graft.

D. Supportive Care:

G-CSF: 5 mcg/kg subcutaneously (SQ), rounded up to nearest vial size, beginning the day after autologous stem cell infusion and expanded cell product infusion. G-CSF will be continued daily until ANC >2000 for two consecutive days.

Evaluation Guidelines

A. Pre-Transplant Evaluation

1. History, physical exam, Karnofsky score.
2. CBC, serum sodium, potassium, CO2, BUN, creatinine, uric acid, LDH, calcium, bilirubin, alkaline phosphatase, AST, ALT, hepatitis screen, ABO/RH typing, blood crossmatch, CMV, VZV, HSV, HIV, and toxoplasmosis serology.
3. CT/PET (lymphoma).
4. MRI of skeleton, and osseous survey needed for staging (myeloma).
5. Bone marrow aspirations and biopsies; samples for pathology, flow cytometry and cytogenetics including FISH.
6. Serum protein electrophoresis and immunofixation (myeloma).
7. Quantitative serum immunoglobulin levels, beta 2 microglobulin.
8. 24 hour urine collection to determine creatinine clearance and total protein excretion, urine protein electrophoresis, quantitative Bence Jones excretion and immunofixation (myeloma).
9. PFTS, MUGA.
10. Clinical immune reconstitution studies.

B. Evaluation During Conditioning:

1. Daily CBC until ANC >500/μl and platelet count >20,000/μl following the nadir.
2. Electrolyte panel (sodium, potassium, chloride, CO2, calcium, magnesium, phosphorus, albumin, BUN creatinine) 3× per week at a minimum.
3. Liver function tests (ALT, AST, ALK phos, bilirubin, and LDH) 2× per week at a minimum.

C. Evaluation to be Completed the Morning of Autologous PBSC and Expanded Progenitor Infusion:

1. Physical exam and review of systems done by provider
2. Weight by nursing
3. CBC [CBD] (includes HCT, HGB, WBC, RBC, indices, platelets, DIFF/SMEAR EVAL)
4. [SRFM] and [SHFL] (HSCT Renal function panel with magnesium and HSCT Hepatic function panel with LD; SRFM includes NA, K, CL, CO2, GLU, BUN, CRE, CA, P, ALB, MG and SHFL includes ALT, AST, ALK, BILIT/D, TP, ALB, LD)
5. Complete urinalysis D. Evaluation During Infusion of Ex Vivo Expanded Cord Blood Progenitors 1. RN must be in attendance during infusion.
2. MD or PA must be available on the inpatient unit.
3. If any changes in cardiac status, notify physician and obtain ECG.
4. Obtain and record vital signs including temperature, BP, HR, Respirations, and 02 saturation at the following time points:

TABLE XIII

| |
|---|
| Pre-infusion |
| 15 minutes after the start of infusion |
| 30 minutes after the start of infusion |
| 45 minutes after the start of infusion |
| 1 hour after the start of infusion |
| 2 hours after the start of infusion |
| 4 hours after the start of infusion |
| 24 hours after the start of infusion |

5. Dipstick for HGB/protein every voided urine for 24 hours after infusion of expanded cells. Record HGB and Protein.

E. Evaluation 24 Hours Following the Infusion of Expanded Cord Blood Progenitors:

1. CBC [CBD] (includes HCT, HGB, WBC, RBC, indices, platelets, DIFF/SMEAR EVAL)
2. [SRFM] and [SHFL] (HSCT Renal function panel with magnesium and HSCT Hepatic function panel with LD;

SRFM includes NA, K, CL, CO2, GLU, BUN, CRE, CA, P, ALB, MG and SHFL includes ALT, AST, ALK, BILIT/D, TP, ALB, LD.

3. Complete Urinalysis

F. Evaluation from Day 0 to Day 60:

1. Daily CBC until ANC >500/μl and platelet count >20,000/μl following the nadir. Thereafter CBC 3× per week until day +28 and 2× per week until day +60.
2. Electrolyte panel (sodium, potassium, chloride, CO2, calcium, magnesium, phosphorus, albumin, BUN creatinine) 3× per week until day 60.
3. Liver function tests (ALT, AST, ALK phos, bilirubin, and LDH) 2× per week until day 28 then weekly until day 60.
4. Engraftment studies: Contribution to hematopoietic recovery from the expanded cell product will be assessed from sorted peripheral blood (cell sorted for $CD3^+$, $CD33^+$, $CD14^+$, and $CD56^+$ cell fractions) on day 7, 14, 21, 28 and 60 following the infusion. If at any time point the patient is 100% host, all subsequent analyses will not be performed. If there is evidence of engraftment from expanded cell product which persists at day 60, chimerism studies will be continued at 2-4 week intervals until the patient is 100% host. The percentages of donor-host chimerism will be evaluated by polymerase chain reaction (PCR)-based amplification of variable-number tandem repeat (VNTR) sequences unique to donors and hosts and quantified by phosphoimaging analyses.
5. Alloimmunization: Repeat PRA to evaluate for the development of anti-HLA antibodies will be performed upon count recovery.
6. GVHD: All patients will be monitored for development of potential transfusion related GVHD. If signs or symptoms of acute GVHD occur, patients will be assessed. Treatment of GVHD will be per institutional guidelines, but only if biopsy proven GVHD is present.
7. Bone Marrow Evaluations: Marrow evaluations will be performed for hematopathology, cytogenetics/FISH, flow cytometry and whole marrow chimerism evaluations on day 14 and 21 (if necessary). In the event of graft failure, a marrow evaluation will be performed to rule out aplasia due to graft versus host effect. Additional marrows will be done as clinically indicated.
8. Adverse event monitoring until day 60 evaluation.
9. Clinical immune reconstitution studies.

G. Day 60 Re-Staging Evaluation

1. History, physical exam, Karnofsky score.
2. CBC, serum sodium, potassium, CO2, BUN, creatinine, uric acid, LDH, calcium, bilirubin, alkaline phosphatase, AST, ALT, hepatitis screen.
3. CT/PET imaging (lymphoma).
4. Osseous survey use skeletal survey for re-staging, and MRI of skeleton (myeloma).
5. Bone marrow aspiration and biopsy; samples for pathology, flow cytometry and cytogenetics including FISH. If there is persistence of the expanded cord blood cells (as demonstrated on peripheral blood chimerism analysis), this marrow will be sent for whole marrow chimerism as well.
6. Quantitative serum immunoglobulin levels.
7. Serum protein electrophoresis and immunofixation (myeloma).
8. 24 hour urine collection to determine creatinine clearance and total protein excretion, urine protein electrophoresis, quantitative Bence Jones excretion and immunofixation (myeloma).
9. Serum B2 microglobulin.
10. Repeat PRA to evaluate for the development of anti-HLA antibodies.
11. Adverse event monitoring
12. Clinical immune reconstitution studies H. Immune Reconstitution:

Clinical Studies (to be performed as possible):

1. Quantitative immunoglobulin levels (IgG, IgA, IgM) will be assessed at Day 28, 60, 100, 6 months, 1 year and 2 years.
2. Total T lymphocytes and subset enumeration (Lymphocytes panel) will be assessed pre-transplant and at Day 28, 60, 100, 6 months, 1 year and 2 years.

I. Follow-Up

1. Complete blood count, renal function, and liver function tests obtained for clinical reasons for a period of 6 months, as needed to define toxicity or duration of response.
2. Disease free and overall survival data will be assessed by contacting the referring MD or the patient every three to six months for the first two years, then annually for 3 years.

J. Supportive Care Guidelines

1. Blood Products: All blood products are to be irradiated and leukocyte-reduced. Also, CMV-negative patients will receive CMV-safe blood products. Transfusions will be administered for symptomatic anemia, or below standard threshold levels appropriate to the clinical setting.
2. Infection Prophylaxis: Prophylactic oral levofloxacin will be used during the period of neutropenia. Acyclovir and bactrim prophylaxis will be used according to standard practice guidelines.
3. Treatment of Fever and Neutropenia; Standard diagnostic testing will be performed as per institutional guidelines, and empiric antibiotic coverage will be utilized. Specific antibiotics will be used for positive cultures.
4. Colony Stimulating Factors: G-CSF will be utilized as outlined above. Erythropoietic stimulating agents will not be utilized.
5. Concomitant Therapy: No concomitant cytotoxic therapy or investigational therapy is allowed during the study with the exception of prophylactic intrathecal therapy per standard practice guidelines.

11. EXAMPLE: TREATMENT OF AML PATIENTS WITH EXPANDED HUMAN CORD BLOOD STEM CELLS AND CORD BLOOD TRANSPLANT

This protocol involves the administration of one or more umbilical cord blood/placental blood units ("Grafts" or "cord blood transplants") in combination with an expanded cord blood stem cell sample of the invention for the treatment of acute myelogenous leukemia (AML) in human patients. The cord blood transplants were cord and/or placental whole blood, except that red blood cells were removed.

Figure 17:
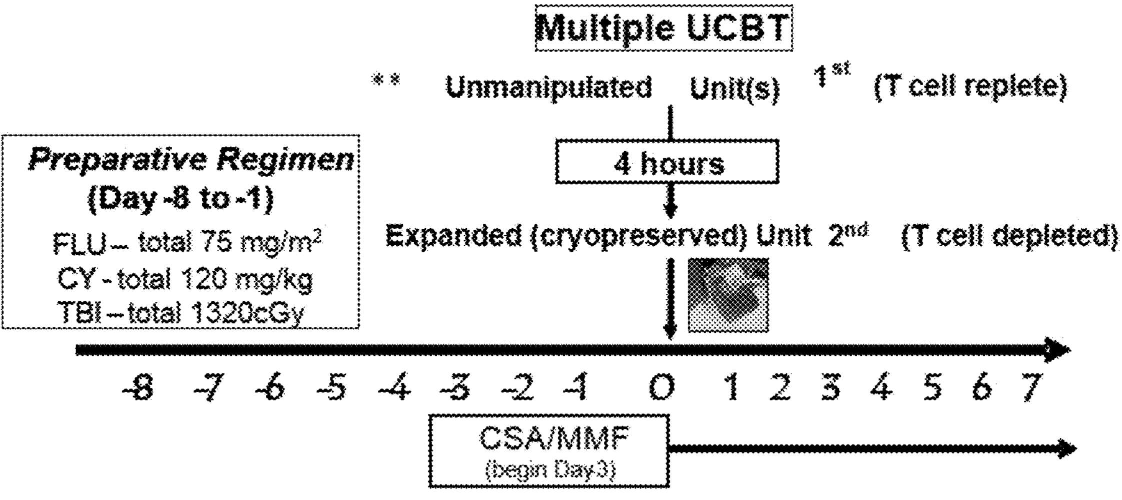
FIG. 17 is a flow chart setting forth a protocol for treating a hematologic malignancy, such as AML, by administering a cord blood transplant and an expanded cord blood stem and progenitor cell sample.

To date, six patients with leukemia at high risk of relapse have been enrolled and received treatment per the treatment protocol set forth in FIG. 17, which is a myeloablative, total body irradiation (TBI)-based cord blood transplant (CBT) protocol for patients with hematologic malignancy ("CSA/MMF" refers to cyclosporin and micophenylatemofetil, a conventional immune-suppressive treatment to prevent graft vs. host disease (GVHD)). The conditioning and post-transplant immune suppression regimens in this study are identical to the ex vivo expansion trial described in Example 9, supra, and are considered standard of care for myeloablative cord blood transplant. The patients received two previously cryopreserved cord blood transplants (depleted of red blood cells) with a minimum of $1.5\times10^7$ total nucleated cells ("TNC")/kg (depending on algorithm of cell dose and HLA typing) and one expanded cord blood stem cell sample produced as described in Example 8, supra.

To date, all patients treated received a double cord blood transplant (cord blood transplants from the cord and/or placental blood of two different individuals) followed by infusion of a previously cryopreserved and thawed, expanded human cord blood stem cell sample without regard to HLA matching, on day 0. No toxicities were observed at the time of infusion and no serious adverse events have been attributed to the expanded human cord blood stem cell sample to date. The first patient was infused on Sep. 22, 2010, and the sixth patient is now 2 months post transplant. The infused TNC and $CD34^+$ cell doses are presented in the table below.

myeloablative double cord blood transplant (conventional dCBT), and (ii) to a cohort of patients who received a myeloablative double cord blood transplant with administration of a partially HLA matched expanded human cord blood stem cell sample that was not cryopreserved (expanded+unmanipulated), as described in Delaney et al., 2010 Nature Med. 16:232-236.

Figure 18:
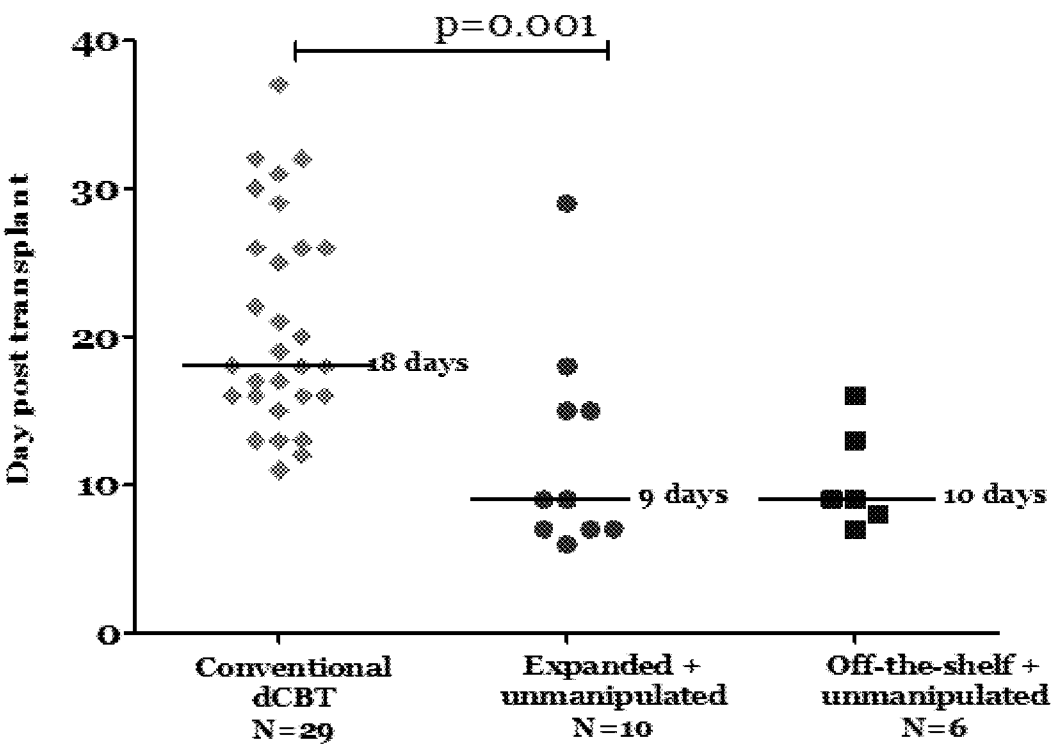
FIG. 18 shows the time required post-transplant to achieve an absolute neutrophil count (ANC) of greater than or equal to 100 per μl.
Figure 19:
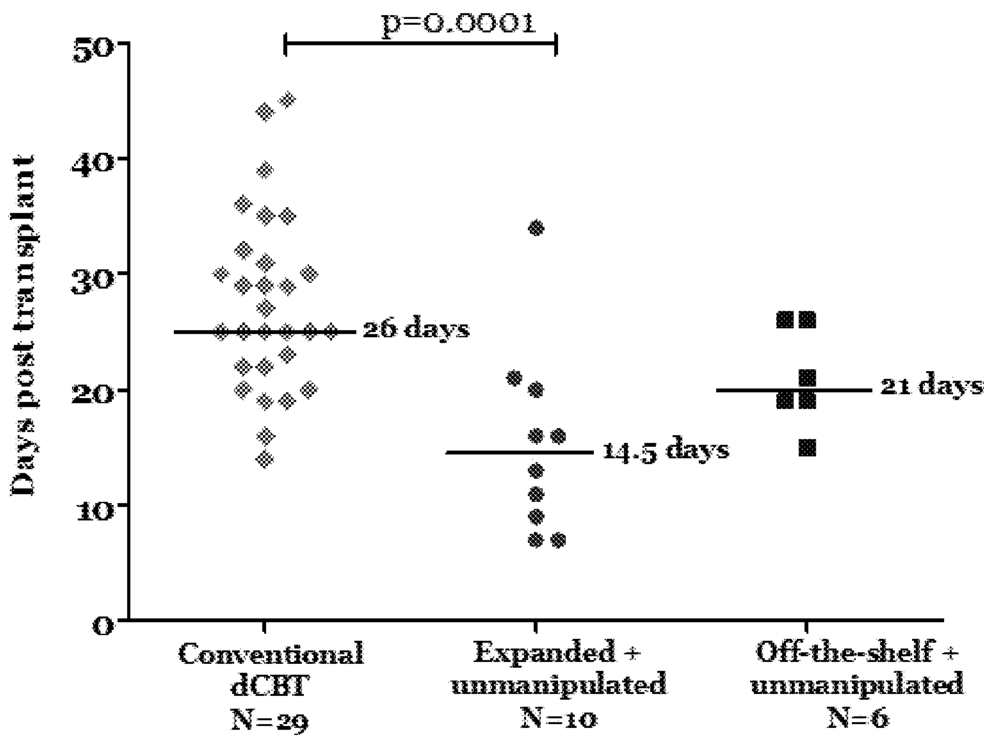
FIG. 19 shows the time required post-transplant to achieve an absolute neutrophil count (ANC) of greater than or equal to 500 per μl.

While the patient numbers were small, an advantage for earlier myeloid recovery is suggested in the patients treated to date with the cryopreserved expanded human cord blood stem cell sample without regard to HLA matching (off-the-shelf+unmanipulated), and in the patients treated with the partially HLA matched expanded human cord blood stem cell sample (expanded+unmanipulated) compared to the conventional double cord blood transplant (conventional dCBT) (see FIG. 18 and FIG. 19). In one of the six patients administered the expanded human cord blood stem cell sample without regard to HLA matching, in vivo persistence of the expanded cord blood stem cells continues to persist when last checked at day 56. Retrospectively, this patient was found to be fortuitously matched at 3/6 HLA antigens to the off-the-shelf product.

TABLE XIV

Demographics, Infused Cell Doses and Engraftment, Patients 1-6

| Pt # | Age | Wt (kg) | Diagnosis | Infused TNC* ($\times10^7$/kg) | Infused TNC** ($\times10^7$/kg) | Infused CD34* ($\times10^6$/kg) | Infused CD34** ($\times10^6$/kg) | 1st Day ANC >100 | 1st Day ANC >500 | Date Platelet >20k |
|---|---|---|---|---|---|---|---|---|---|---|
| 1 | 35 | 67.1 | AML | 8.9 | 2.7 | 0.31 | 4.1 | 8 | 26 | 35 |
| 2 | 5 | 27.4 | ALL | 7.3 | 10.0 | 0.37 | 9.8 | 13 | 15 | 26 |
| 3 | 24 | 76.4 | ALL | 4.0 | 6.9 | 0.12 | 9.2 | 9 | 19 | 37 |
| 4 | 21 | 74 | ALL | 4.8 | 4.7 | 0.16 | 4.9 | 16 | 21 | 35 |
| 5 | 13 | 57 | ALL | 4.2 | 7.2 | 0.15 | 8.8 | 7 | 26 | 45 |
| 6 | 33 | 72 | AML | 5.2 | 6.8 | 0.16 | 11.1 | 9 | 19 | 33 |
| Mean | 21.2 | 61.2 | — | 5.7 | 6.5 | 0.21 | 8 | 10 | 21 | 35 |

*Total of both unmanipulated units.

**Based on pre-freeze total of off-the-shelf expanded unit.

The kinetics of hematopoietic recovery and the relative contribution of the expanded cells and cord blood graft cells to engraftment were determined beginning on day 7 post transplant. All patients treated to date have engrafted. It has been previously demonstrated that an ANC 100 is a critical threshold to reduce the risk of death prior to day 100 post hematopoietic cell transplant (Offner et al., 1996, Blood 88:4058). Furthermore, in our own single center analysis of severe neutropenia following cord blood transplant, both ANC <100 and time to engraftment as a time-dependent covariate, correlates significantly with both day 200 transplant related mortality ("TRM") and overall survival. In this analysis of 88 patients undergoing cord blood transplant, at any given time point, an ANC <100 is associated with a 4.77-fold increase in the risk of overall mortality compared to an ANC >100 (1.74-13.11, $p=0.002$) and an 8.95-fold increase in risk of day 200 TRM (2.59-30.89, $p=0.00095$). This is similar to findings when modeling the time to engraftment (ANC >500), such that engraftment at a specific time point is associated with a 0.23-fold risk of death as compared to lack of engraftment at this time (0.08-0.62, $p=0.004$), and a 0.11-fold risk of day 200 TRM (0.03-0.38, $p=0.0005$). Therefore, the time to achieve an ANC ≥100 and the time to achieve ANC 500 were evaluated in patients who underwent a myeloablative double cord blood transplant with administration of a previously cryopreserved expanded human cord blood stem cell sample without regard to HLA matching (off-the-shelf+unmanipulated), compared (i) to a concurrent cohort of patients who received a conventional Early myeloid recovery at day 7 was derived almost entirely from the previously cryopreserved expanded human cord blood stem cell sample that was administered to all 6 patients without regard to HLA matching, but generally such recovery did not persist beyond day 14 post-transplant (see FIG. 20). This result is in accord with results seen when infusing a freshly harvested (not cryopreserved) and partially HLA matched expanded human cord blood stem cell sample, as described in Delaney et al., 2010 Nature Med. 16; 232-236.

It is envisioned that future patients will receive one, two or more cord blood transplants in addition to the expanded human cord blood stem cell sample.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications, including patents, patent application publications, and scientific literature, are cited herein, the disclosures of which are incorporated by reference in their entireties for all purposes.

The invention claimed is:

1. A method of treating acute myelogenous leukemia (AML) in a human patient, comprising:

administering to the human patient a $CD34^+$ enriched, T cell depleted, Notch agonist expanded human cord blood stem and progenitor (HSPC) cell product, wherein the cell product composition consists of a pool of HLA unmatched HSPC samples from at least two human donors without regard to the HLA type of the donors and without taking into account the HLA type of the human patient and a pharmaceutically acceptable carrier, excipient or buffer; and engrafting transiently cells from the HSPC cell product; thereby treating AML in the human patient.

2. The method of claim 1, wherein the cell product was produced by steps comprising enriching the pooled HSPC sample for $CD34^+$ human cord blood stem and progenitor cells; and expanding the HLA unmatched $CD34^+$ enriched human cord blood stem and progenitor cells with a Notch-agonist.

3. The method of claim 1, wherein the human patient had been previously treated with an intensive chemotherapy regimen or a myeloablative regimen for hematopoietic cell transplantation.

4. The method of claim 1, wherein the cell product comprises at least 75 million viable HLA unmatched $CD34^+$ cells.

5. The method of claim 4, wherein the cell product comprises at least 250 million viable HLA unmatched $CD34^+$ cells.

6. The method of claim 1, wherein the human patient has an immunodeficiency.

7. The method of claim 1, wherein the cell product further comprises a cryoprotective agent.

8. The method of claim 1, wherein the cell product has been cryopreserved and then thawed prior to administration.

9. The method of claim 1, wherein the method further comprises the step of administering to the human patient an HLA typed unmanipulated cord blood sample which is immunologically matched or mismatched to the human patient.

* * * * *